United States Patent
Pierce et al.

(10) Patent No.: US 10,450,599 B2
(45) Date of Patent: Oct. 22, 2019

(54) FRACTIONAL INITIATOR HYBRIDIZATION CHAIN REACTION

(71) Applicant: California Institute of Technology, Pasadena, CA (US)

(72) Inventors: Niles A. Pierce, Pasadena, CA (US); Harry Ming Tak Choi, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 28 days.

(21) Appl. No.: 15/639,100

(22) Filed: Jun. 30, 2017

(65) Prior Publication Data

US 2018/0010166 A1    Jan. 11, 2018

Related U.S. Application Data

(60) Provisional application No. 62/358,462, filed on Jul. 5, 2016.

(51) Int. Cl.
*C12Q 1/68* (2018.01)
*C07H 21/00* (2006.01)
*C12Q 1/682* (2018.01)

(52) U.S. Cl.
CPC .................. *C12Q 1/682* (2013.01)

(58) Field of Classification Search
CPC .................. C12Q 1/68; C07H 21/00
See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,270,163 A | 12/1993 | Gold et al. |
| 5,312,728 A | 5/1994 | Lizardi et al. |
| 5,424,413 A | 6/1995 | Hogan et al. |
| 5,459,127 A | 10/1995 | Feigner et al. |
| 5,563,256 A | 10/1996 | Chakraborty et al. |
| 5,579,793 A | 12/1996 | Gajewski et al. |
| 5,635,352 A | 6/1997 | Urdea et al. |
| 5,643,741 A | 7/1997 | Tsukamoto et al. |
| 5,677,136 A | 10/1997 | Simmons et al. |
| 5,681,697 A | 10/1997 | Urdea et al. |
| 5,691,145 A | 11/1997 | Pitner et al. |
| 5,716,827 A | 2/1998 | Tsukamoto et al. |
| 5,750,397 A | 5/1998 | Tsukamoto et al. |
| 5,928,913 A | 7/1999 | Efstathiou et al. |
| 5,989,823 A | 11/1999 | Jayasena et al. |
| 6,128,587 A | 10/2000 | Sjolander |
| 6,130,047 A | 10/2000 | Nadeau et al. |
| 6,242,246 B1 | 6/2001 | Gold et al. |
| 6,255,469 B1 | 7/2001 | Seeman et al. |
| 6,261,783 B1 | 7/2001 | Jayasena et al. |
| 6,264,825 B1 | 7/2001 | Blackburn et al. |
| 6,361,944 B1 | 3/2002 | Mirkin et al. |
| 6,361,945 B1 | 3/2002 | Becker et al. |
| 6,485,965 B1 | 11/2002 | Klatzmann et al. |
| 6,506,559 B1 | 1/2003 | Fire et al. |
| 6,555,367 B1 | 4/2003 | Spence et al. |
| 6,696,285 B1 | 2/2004 | Mills et al. |
| 6,899,871 B2 | 5/2005 | Kasahara et al. |
| 7,033,834 B2 | 4/2006 | Valerio et al. |
| 7,632,641 B2 | 12/2009 | Dirks et al. |
| 7,709,198 B2 | 5/2010 | Luo et al. |
| 7,727,721 B2 | 6/2010 | Pierce et al. |
| 7,960,357 B2 | 6/2011 | Dirks et al. |
| 8,105,778 B2 | 1/2012 | Dirks et al. |
| 8,124,751 B2 | 2/2012 | Pierce et al. |
| 8,241,854 B2 | 8/2012 | Yin et al. |
| 8,318,921 B2 | 11/2012 | Pierce et al. |
| 8,478,543 B2 | 7/2013 | Pierce et al. |
| 8,497,364 B2 | 7/2013 | Pierce et al. |
| 8,507,204 B2 | 8/2013 | Pierce et al. |
| 8,604,182 B2 | 12/2013 | Luo et al. |
| 8,658,361 B2 | 2/2014 | Luo et al. |
| 8,658,780 B2 | 2/2014 | Pierce et al. |
| 8,877,438 B2 | 11/2014 | Yin |
| 8,951,726 B2 | 2/2015 | Luo et al. |
| 8,962,241 B2 | 2/2015 | Yin et al. |
| 8,962,582 B2 | 2/2015 | Dirks et al. |

(Continued)

FOREIGN PATENT DOCUMENTS

| EP | 0 273 085 A1 | 7/1988 |
|---|---|---|
| EP | 0731848 B1 | 5/2003 |

(Continued)

OTHER PUBLICATIONS

Aagaard et al., "RNAi Therapeutics: Principles, Prospects and Challenges." Advanced Drug Delivery Reviews, vol. 59, pp. 75-86, 2007.
Acloque, H. et al., "In situ hybridization analysis of chick embryos in whole-mount and tissue sections," Methods in Cell Biology, vol. 87, pp. 169-185, 2008.
Allan et al., "A Concise Total Synthesis of (-)-Quinocarcin via Aryne Annulation," Journal of American Chemical Society, vol. 130, pp. 17270-17271, 2008.
Amarzguioui et al., "Rational design and in vitro and in vitro delivery of Dicer substrate siRNA," Nature Protocols, vol. 1, No. 2, pp. 508-617, 2006.
An, C. I. et al., "Artificial control of gene expression in mammalian cells by modulating RNA interference through aptamer-small molecule interaction," RNA, vol. 12, 710-716, 2006.

(Continued)

*Primary Examiner* — Ethan C Whisenant
(74) *Attorney, Agent, or Firm* — Knobbe, Martens, Olson & Bear, LLP

(57) ABSTRACT

The present disclosure relates to methods and compositions involving HCR reactions that involve initiators that are split into two or more parts. Effective HCR is dependent upon two or more of these split initiators being brought into proximity (e.g., via binding events mediated by a target) such that a full initiator is formed that is capable of triggering HCR signal amplification.

9 Claims, 16 Drawing Sheets

(56) References Cited

U.S. PATENT DOCUMENTS

| | | |
|---|---|---|
| 9,217,151 B2 | 12/2015 | Yin et al. |
| 9,834,439 B2 | 12/2017 | Yin et al. |
| 9,856,472 B2 | 1/2018 | Pierce et al. |
| 2001/0014445 A1 | 8/2001 | Urnovitz |
| 2002/0051769 A1 | 5/2002 | Zhang |
| 2002/0172950 A1 | 11/2002 | Kenny et al. |
| 2003/0092162 A1 | 5/2003 | Shankara et al. |
| 2003/0129611 A1 | 7/2003 | Bao et al. |
| 2003/0207295 A1 | 11/2003 | Gunderson et al. |
| 2003/0215821 A1 | 11/2003 | Gunderson et al. |
| 2004/0009510 A1 | 1/2004 | Seiwert et al. |
| 2004/0018491 A1 | 1/2004 | Gunderson et al. |
| 2004/0043386 A1 | 3/2004 | Pray et al. |
| 2004/0126773 A1 | 7/2004 | Beske et al. |
| 2004/0223953 A1 | 11/2004 | Kung et al. |
| 2005/0089864 A1 | 4/2005 | Li et al. |
| 2005/0100893 A1 | 5/2005 | Gunderson et al. |
| 2005/0112614 A1 | 5/2005 | Cook |
| 2005/0233332 A1 | 10/2005 | Collis |
| 2005/0239061 A1 | 10/2005 | Marshall et al. |
| 2005/0260635 A1 | 11/2005 | Dirks et al. |
| 2006/0035375 A1 | 2/2006 | Head et al. |
| 2006/0088864 A1 | 4/2006 | Smolke et al. |
| 2006/0228733 A1 | 10/2006 | Pierce et al. |
| 2006/0234261 A1 | 10/2006 | Pierce et al. |
| 2007/0072215 A1 | 3/2007 | Seelig et al. |
| 2007/0087334 A1 | 4/2007 | Dirks et al. |
| 2007/0117109 A1 | 5/2007 | Rothemund |
| 2008/0038725 A1 | 2/2008 | Luo et al. |
| 2008/0183958 A1 | 7/2008 | Cheriton |
| 2008/0214488 A1 | 9/2008 | Pierce et al. |
| 2009/0011956 A1 | 1/2009 | Yin et al. |
| 2009/0123914 A1 | 5/2009 | Erikson et al. |
| 2009/0197271 A1 | 8/2009 | Kotlikoff et al. |
| 2009/0227774 A1 | 9/2009 | Tuberfield et al. |
| 2009/0247615 A1 | 10/2009 | Pierce et al. |
| 2009/0311799 A1 | 12/2009 | Sotzing et al. |
| 2010/0021901 A1 | 1/2010 | Yin et al. |
| 2010/0021904 A1 | 1/2010 | Pierce et al. |
| 2010/0035233 A1 | 2/2010 | Yin et al. |
| 2010/0047926 A1 | 2/2010 | Dirks et al. |
| 2011/0059064 A1 | 3/2011 | Possani-Potsay et al. |
| 2011/0104676 A1 | 5/2011 | Pierce et al. |
| 2011/0287557 A1 | 11/2011 | Zhang et al. |
| 2011/0288148 A1 | 11/2011 | Pierce et al. |
| 2011/0288832 A1 | 11/2011 | Pierce et al. |
| 2011/0313030 A1 | 12/2011 | Dirks et al. |
| 2012/0021410 A1 | 1/2012 | Yin et al. |
| 2012/0022243 A1 | 1/2012 | Yin et al. |
| 2012/0022244 A1 | 1/2012 | Yin |
| 2012/0190835 A1 | 7/2012 | Pierce et al. |
| 2012/0251583 A1 | 10/2012 | Rothemund |
| 2013/0171621 A1 | 7/2013 | Luo et al. |
| 2014/0107983 A1 | 4/2014 | Wolfe et al. |
| 2015/0004615 A1 | 1/2015 | Pierce et al. |
| 2015/0154347 A1 | 6/2015 | Wolfe et al. |
| 2017/0022499 A1 | 1/2017 | Lu et al. |
| 2018/0066303 A1 | 3/2018 | Pierce et al. |
| 2018/0362944 A1 | 12/2018 | Hanewich-Hollatz et al. |

FOREIGN PATENT DOCUMENTS

| | | |
|---|---|---|
| EP | 1 479 766 A1 | 11/2004 |
| EP | 1 634 890 A1 | 3/2006 |
| EP | 2 055 781 A2 | 5/2009 |
| EP | 1 730 161 B1 | 9/2010 |
| EP | 1 931 806 B1 | 10/2011 |
| EP | 2460893 A1 | 6/2012 |
| EP | 2 155 770131 | 10/2013 |
| EP | 2630260 B1 | 11/2015 |
| EP | 1910572 B1 | 12/2015 |
| EP | 2500439 B2 | 8/2017 |
| EP | 2529030 B1 | 3/2019 |
| WO | WO 92/03464 A1 | 3/1992 |
| WO | WO 94/01550 A1 | 1/1994 |
| WO | WO 99/31276 A1 | 6/1999 |
| WO | WO 01/40516 A2 | 6/2001 |
| WO | WO 2005/098049 A2 | 10/2005 |
| WO | WO 2006/002167 A2 | 1/2006 |
| WO | WO 2006/048025 A1 | 5/2006 |
| WO | WO 2007/008276 A2 | 1/2007 |
| WO | WO 2007/044727 A2 | 4/2007 |
| WO | WO 2007/141809 A1 | 12/2007 |
| WO | WO 2007/148337 A2 | 12/2007 |
| WO | WO 2008/106658 A2 | 9/2008 |
| WO | WO 2008/144562 A1 | 11/2008 |
| WO | WO 2011/126996 A2 | 10/2011 |
| WO | WO 2014/074648 A2 | 5/2014 |
| WO | WO 2015/1180929 | 8/2015 |
| WO | WO 2015/168404 A1 | 11/2015 |
| WO | WO 2016/011089 A1 | 1/2016 |
| WO | WO 2017/223449 A1 | 12/2017 |
| WO | WO 2018/009463 A3 | 1/2018 |
| WO | WO 2018/044939 | 3/2018 |
| WO | WO 2018/231730 A2 | 12/2018 |

OTHER PUBLICATIONS

Andronescu et al., "A New Algorithm for RNA Secondary Structure Design", J. Mol. Biol., vol. 336, pp. 607-624, 2004.

Asbury, C.L., "Kinesin: world's tiniest biped", Current Opinion in Cell Biology, vol. 17, pp. 89-97, 2005.

Barish et al., "An Information-Bearing seed for nucleating algorithmic self assembly." Proceedings of the National Academy of Sciences, vol. 106, pp. 6054, 2009.

Barroso-Chinea, P. et al., "Detection of two different mRNAs in a single section by dual in situ hybridization: A comparison between colorimetric and fluorescent detection," Journal of Neuroscience Methods, vol. 162, Issues 1-2, pp. 119-128, May 15, 2007.

Bates et al., "Multicolor super-resolution imaging with photo-switchable fluorescent probes." Science, vol. 317, pp. 1749-1759, 2007.

Bath et al., "DNA nanomachines", Nature Nanotechnology, vol. 2, pp. 275-284, May 2007.

Behenna et al., "The Enantioselective Tsuji Allylation," Journal of American Chemical Society, vol. 126.46 pp. 15044-15045, 2004.

Beisel, C. L.et al., "Model-guided design of ligand-regulated RNAi for programmable control of gene expression," Mol. Syst. Biol., vol. 4, pp. 224, 2008.

Beisel, C. L. et al., "Design of small molecule-responsive microRNAs based on structural requirements for Drosha processing," Nucleic Acids Res., vol. 39, pp. 2981-2994, 2011.

Bhatia et al., "Icosahedral DNA Nanocapsules by Modular Assembly," Angew. Chem. Int. Ed., vol. 48, pp. 4134-4137, 2009.

Bloomfeld et al., "Nucleic Acids: Structures, Properties, and Functions," University Science Books, Table of Contents Only, 2000.

Bois et al., "Topological constraints in nucleic acid hybridization kinetics", Nucleic Acids Research, vol. 33, No. 13, pp. 4090-4095, 2005.

Bois J.S., "Analysis of interacting nucleic acids in dilute solutions" Ph.D. Thesis. California Institute of Technology. (2007).

Bolt et al., "Differential Reactivities of the mono- and di-epoxide of 1,3-butadiene," Toxicology, vol. 113, pp. 294-296, 1996.

Bonnet et al. Thermodynamic basis of the enhanced specificity of structured DNA probes, Proc. Natl. Acad. Sci. USA vol. 96, pp. 6171-6176, May 1999.

Brummelkamp, T. R. et al., "A system for stable expression of short interfering RNAs in mammalian cells" Science, vol. 296, pp. 550-553, 2002.

Bumcrot et al., "RNAi Therapeutics: A Potential New Class of Pharmaceutical Drugs." Nature Chemical Biology, vol. 2.12, pp. 711-719, Dec. 2006.

Bushnell et al., "ProbeDesigner: for the design of probesets for branched DNA (bDNA) signal amplification assays," Bioinformatics, vol. 15, No. 5, pp. 348-355, 1999.

Butterfoss et al., Computer-Based Design of Novel Protein Structures, Annu. Rev. Biophys. Biomol. Struct., vol. 35, pp. 49-65, 2006.

Caltech News Release, "Caltech Scientists Create New Process to Program", Sep. 6, 2010.

(56) References Cited

OTHER PUBLICATIONS

Caplen, "RNAi as a gene therapy approach", Expert Opin. Biol. Ther., vol. 3, No. 4, pp. 575-586, 2003.
Capodieci, P. et al., "Gene expression profiling in single cells within tissue," Nat Methods, vol. 2, No. 9, pp. 663-665, Sep. 2005.
Castanotto et al., "The Promises and Pitfalls of RNA-Interface-Based Therapeutics." Nature, vol. 457, pp. 426-433, Jan. 22, 2009.
Cerutti et al., "On the Origin and Functions of RNA-Mediated Silencing: From Protists to Man." Current Genetics, vol. 50, pp. 81-99, 2006.
Chan, PM et al., "Method for multiplex cellular detection of mRNAs using quantum dot fluorescent in situ hybridization," Nucleic Acids Research, vol. 33, Issue 18, pp. e161, Jan. 1, 2005.
Check, "RNA to the rescue?", Nature, vol. 425, pp. 10-12, Sep. 4, 2003.
Chen et al., "DNA-Directed Assembly of Single-Wall Carbon Nanotubes." J.Am. Chem. Soc., vol. 129, 2007.
Chen et al., "Invadable self-assembly: Combining robustness with efficiency." In Proceedings of the 15.sup.th annual ACM-SIAM Symposium on Discrete Algorithms (SODA); 2004.
Choi et al., "Programmable in situ amplification for multiplexed imaging of mRNA expression," Nature Biotechnology, vol. 28, No. 11, pp. 1208-1214, 2010.
Choi, H. et al., "Next-generation in situ hybridization chain reaction: Higher gain, lower cost, greater durability," ACS Nano, vol. 8, No. 5, pp. 4284-4294, 2014.
Clay, H. et al., "Multiplex fluorescent in situ hybridization in zebrafish embryos using tyramide signal amplification," Zebrafish, vol. 2, No. 2, pp. 105-111, Aug. 2005.
Coburn et al., "siRNAs: a new wave of RNA-based therapeutics", Journal of Antimicrobial Chemotherapy, vol. 51, pp. 753-756, 2003.
Coleman et al., "Template-Directed Cross-Linking of Oligonucleotides: Site-Specific Covalent Modification of dG-N7 Within Duplex DNA." J. Org. Chem., vol. 60, pp. 6252-6253, 1995.
Coleman, R.S, and Pires, R.M., Covalent cross-linking of duplex DNA using 4-thio-2'-deoxyuridine as a readily modifiable platform for introduction of reactive functionality into oligonucleotides. Nucleic Acids Research, vol. 25: p. 4771-4777, 1997.
Collins et al., "A branched DNA signal amplification assay for quantification of nucleic acid targets below 100 molecules/ml," Nucleic Acids Res, vol. 25, No. 15, pp. 2979-2984, 1997.
Communication pursuant to Article 94(3) EPC dated Nov. 7, 2012 from Application No. 08755764.1, filed May 16, 2008.
Coppelli et al., "Oligonucleotides as Anticancer Agents: From the Benchside to the Clinic and Beyond", Current Pharmaceutical Design, vol. 11, pp. 2825-2840, 2005.
Cox, K.H. et al., "Detection of mRNAs in sea urchin embryos by in situ hybridization using asymmetric RNA probes," Developmental Biology, vol. 101, Issue 2, pp. 485-502, Feb. 1984.
Cullen et al., "Genome-wide Screening for Gene Function Using RNAi in Mammalian Cells." Immunology and Cell Biology, vol. 83, pp. 217-223, 2005.
Czauderna et al., "Structural Variations and Stabilising Modifications of Synthetic siRNAs in Mammalian Cells," Nucleic Acids Research, vol. 31.11, pp. 2705-2716, 2003.
Dabby, et al., "The kinetics of toehold-mediated four-way branch migration." California Institute of Technology Thesis, Chapter 5, pp. 75-105, 2013.
Darnell, D.K. et al., "GEISHA: an in situ hybridization gene expression resource for the chicken embryo," Cytogenetic and Genome Research, vol. 117, No. 1-4, pp. 30-35, Jul. 2007.
Definition for "substantial" from Merriam-Webster Online Dictionary. Downloaded from merriam-webster.com; downloaded on Mar. 5, 2008.
Denkers, N. et al., "FISHing for chick genes: Triple-label whole-mount fluorescence in situ hybridization detects simultaneous and overlapping gene expression in avian embryos," Developmental Dynamics, vol. 229, Issue 3, pp. 651-657, Mar. 2004.

Dias et al., "Antisense Oligonucleotides: Basic Concepts and Mechanisms." Molecular Cancer Therapeutics, vol. 1, pp. 347-355, Mar. 2002.
Dietz et al., "Folding DNA into Twisted and Curved Nanoscale Shapesm," Science, vol. 325, pp. 725-730, 2009.
Dirks et al., Retraction for "Selective cell death mediated by small conditional RNAs" (which appeared in issue 39, Sep. 28, 2010 of Proc Natl Acad Sci USA), Proc Natl Acad Sci USA, vol. 110, No. 1, pp. 384, Jan. 2, 2013.
Dirks et al., "A Partition Function Algorithm for Nucleic Acid Secondary Structure Including Pseudoknots." Journal of Computational Chemistry, vol. 24.13, pp. 1664-1677, 2003.
Dirks et al., "An Algorithm for Computing Nucleic Acid Base-Pairing Probabilities Including Pseudoknots." Journal of Computational Chemistry, vol. 25.10, pp. 1295-1304, 2004.
Dirks et al., "Paradigms for computational nucleic acid design," Nucleic Acids Research, vol. 32, No. 4, pp. 1392-1403, Oxford University Press, 2004.
Dirks et al., "Thermodynamic Analysis of Interacting Nucleic Acid Strands." SIAM Review, vol. 49.1, pp. 65-88, 2007.
Dirks, R.M. et al., "Triggered amplification by hybridization chain reaction," PNAS, vol. 101, No. 43, pp. 15275-15278, Oct. 26, 2004.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.
Du, Qa et al., "A systematic analysis of the silencing effects of an active siRNA at all single-nucleotide mismatched target sites." Nucleic Acids Res, vol. 33, pp. 1671-1677, 2005.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Dunn JJ, et al., "Complete nucleotide-sequence of bacteriophage-T7 DNA and the locations of T7 genetic elements." J Mol Biol, vol. 166, pp. 477-535, 1983.
Eckstein, F., "Phosphrothioate oligodeooxynucleotides: what is their origin and what is unique about them?" Antisense Nucleic Acid Drug Dev., vol. 10, pp. 117-121, 2000.
Eddy, S.R., "Non-coding RNA genes and the modern RNA world." Nature Reviews, vol. 2, pp. 919-929, 2001.
Elbashir et al., "Functional anatomy of siRNAs for mediating efficient RNAi in *Drosophila melanogaster* embryo lysate", The EMBO Journal, vol. 20, No. 23, pp. 6877-6888, 2001.
Elghanian et al.,"Selective colorimetric detection of polynucleotides based on the distance-dependent optical properties of gold nanoparticles," Science, vol. 277, No. 5329, pp. 1078-1081, 1997.
Ellington, A. et al., "In vitro selection of RNA molecules that bind specific ligands," Nature, vol. 346, pp. 818-822, Aug. 30, 1990.
Elmen et al., "Locked Nucleic Acid (LNA) Mediated Improvements in siRNA Stability and Functionality." Nucleic Acids Research, vol. 33.1, pp. 439-447, 2005.
Enquist et al., "The Total Synthesis of (-)-Cyanthiwigin F by Means of Double Catalytic Enantioselective Alkylation," Nature, vol. 453.7199, pp. 1228-1231, Jun. 26, 2008.
Evanko, "Hybridization chain reaction", Nature Methods, vol. 1, No. 3, pp. 186-187, Dec. 2004.
Extended European Search Report dated Apr. 22, 2010 in European Patent Application No. 06836249.0.
Extended European Search Report dated Nov. 7, 2011 in Application No. 08755764.1, filed May 16, 2008.
Feldkamp et al., "Rational Design of DNA Nanoarchitectures", Angew. Chem. Int. Ed., vol. 45, pp. 1856-1876, 2006.
Felgner et al., "Nomenclature for Synthetic Gene Delivery Systems", Human Gene Therapy, vol. 8, pp. 511-512, Mar. 20, 1997.
Femino, A et al., "Visualization of Single Molecules of mRNA in Situ." Methods of Enzymology, vol. 361, pp. 245-304, 2003.

(56) References Cited

OTHER PUBLICATIONS

Femino, A. et al., "Visualization of single RNA transcripts in situ," Science, vol. 280, Issue 5363, pp. 585-590, Apr. 24, 1998.
Ferkol et al., "Gene Transfer into the Airway Epithelium of Animals by Targeting the Polymeric Immunoglobulin Receptor", J. Clin. Invest., vol. 95, pp. 493-502, Feb. 1995.
Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.
Ferreira et al., "The Palladium-Catalyzed Oxidative Kinetic Resolution of Secondary Alcohols with Molecular Oxygen." Journal of American Chemical Society, vol. 123.31, pp. 7725-7726, 2001.
File History for U.S. Appl. No. 12/790,379.
File History for U.S. Appl. No. 13/186,228.
File History of U.S. Appl. No. 13/186,315, filed Jul. 19, 2011.
File History of U.S. Appl. No. 13/186,331, filed Jul. 19, 2011.
File History of U.S. Appl. No. 14/033,081.
File History of U.S. Appl. No. 14/320,479.
File History of U.S. Appl. No. 14/497,070.
Final Office Action dated Aug. 1, 2014 for U.S. Appl. No. 12/454,799.
Final Office Action dated Aug. 29, 2014 for U.S. Appl. No. 12/467,755.
Final Office Action dated Dec. 10, 2012 for U.S. Appl. No. 13/363,022.
Final Office Action dated Feb. 4, 2016 for U.S. Appl. No. 12/467,755.
Final Office Action dated Jan. 22, 2014 for U.S. Appl. No. 13/186,331.
Final Office Action dated Jul. 2, 2014 for U.S. Appl. No. 13/154,989.
Final Office Action dated Jul. 15, 2011 for U.S. Appl. No. 12/040,735.
Final Office Action dated Jul. 25, 2011 for U.S. Appl. No. 12/395,489.
Final Office Action dated Jun. 25, 2014 for U.S. Appl. No. 13/186,315.
Final Office Action dated Jun. 28, 2013 for U.S. Appl. No. 13/186,228.
Final Office Action dated Mar. 7, 2013 for U.S. Appl. No. 13/016,811.
Final Office Action dated May 27, 2010 for U.S. Appl. No. 11/544,306.
Final Office Action dated Nov. 25, 2015 for U.S. Appl. No. 12/454,799.
Final Office Action dated Oct. 15, 2010 for U.S. Appl. No. 12/152,893.
Final Office Action dated Oct. 29, 2014 for U.S. Appl. No. 13/186,228.
Final Office Action dated Sep. 17, 2010 for U.S. Appl. No. 12/467,755.
Final Office Action dated Sep. 20, 2010 for U.S. Appl. No. 12/454,799.
Fire et al., "Potent and specific genetic interference by double-stranded RNA in Caenorhabditis elegans", Nature, vol. 391, pp. 806-811, Feb. 19, 1998.
Flamm et al., "RNA folding at elementary step resolution," RNA, vol. 6, pp. 325-338, 2000.
Friedrich et al., "RNA molecules as anti-cancer agents", Seminars in Cancer Biology, vol. 14, pp. 223-230, 2004.
Friedrich et al., "A Cellular Screening Assay to Test the Ability of PKR to Induce Cell Death in Mammalian Cells," Molecular Therapy, vol. 12, No. 5, pp. 969-975, Nov. 2005.
Fu et al., "DNA Double-Crossover Molecules", Biochemistry, vol. 32, pp. 3211-3220, 1993.
Gall, J. et al., "Formation and detection of RNA-DNA hybrid molecules in cytological preparations," Proc Natl Acad Sci USA, vol. 63, No. 2, pp. 378-383, Jun. 1, 1969.
Garcia et al., "Impact of Protein Kinase PKR in Cell Biology: from Antiviral to Antiproliferative Action." Microbiology and Molecular Biology Reviews, vol. 70, No. 4, pp. 1032-1060, Dec. 2006.
Garg et al., "A Ligand-free Solid-supported System for Sonogashira Couplings: Applications in Nucleoside Chemistry." Chem. Commun., pp. 4551-4553, 2005.
Garg et al., "Development of an Enantiodivergent Strategy for the Total Synthesis of (+)- and (-)-Dragmacidin F from a Single Enantiomer of Quinic Acid." Journal of American Chemical Society, vol. 127, No. 225, pp. 5970-5978, Apr. 2, 2005.
Gasparro et al., Site-specific targeting of psoralen photoadducts with a triple helix-forming oligonuicleotide: characterization of psoralen monoadduct and crosslink formation. Nucleic Acids Research, vol. 22, pp. 2845-2852, 1994.
Gilman et al., "The Biological Actions and Therapeutic Applications of the B-Chloroethyl Amines and Sulfides," Science, vol. 103.2675, pp. 409-415, Apr. 5, 1946.
Goodman et al., "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Ha et al., Regulation of microRNA biogenesis, Nature Reviews Molecular Cell Biology, vol. 15, pp. 509-524. Jul. 16, 2014.
Hansma et al., "DNA Binding to Mica Correlates with Cationic Radius: Assay by Atomic Force Microscopy", Biophysical Journal, vol. 70, pp. 1933-1939, Apr. 1996.
Harland, R.M., "In situ hybridization : an improved whole-mount method for Xenopus embryos," Methods Cell Biol., vol. 36, pp. 685-695, 1991.
Hashimoto et al., "Recent Progress in Diazirine-Based Photoaffinity Labeling," Eur. J. Org. Chem., pp. 2513-2523, 2008.
Haugland RP. The Handbook: A Guide to Fluorescent Probes and Labeling Technologies. 10th Ed. Molecular Probes/Invitrogen; 2005.
He et al., "Hierarchical self-assembly of DNA into symmetric supramolecular polyhedral," Nature, vol. 452, pp. 198-202, 2008.
Hearst et al., "Psoralen Photochemistry." Ann.Rev. Biophys. Bioeng., vol. 10, pp. 69-86, 1981.
Heidel, J.D., "Targeted, systematic non-viral delivery of small interfering RNA in vivo", Doctoral thesis, California Institute of Technology, pp. 1-128, 2005.
Hell, S.W., "Far-field optical nanoscopy.", Science, vol. 316, pp. 1153-1158, 2007.
Herath et al., "Synthesis of Acrimarins from 1,3,5-Trioxygenated-9-acridone Derivatives." Journal of Heterocyclic Chem., vol. 41, pp. 23-28, 2004.
Higuchi et al., "Selective regulation of mutant K-res mRNA expression by photo-cross-linking antisense oligonucleotide," Nucleic Acids Symposium Series, vol. 51, No. 1, pp. 443-444, 2007.
Hochrein et al., "Conditional Dicer Substrate Formation via Shape and Sequence Transduction with Small Conditional RNAs," J. Am. Chem. Soc., vol. 135, pp. 17322-17330, 2013.
Hofacker et al., "Fast folding and comparison of RNAa secondary structures," Monatshefte fur Chemie, vol. 125, pp. 167-188, 1994.
Hokaiwado et al., "RNAi-based drug discovery and its application to therapeutics", IDrugs, vol. 11, No. 4, pp. 274-278, 2008.
Hughes et al., "Double Labeling wit Fluorescence In Situ Hybridization in *Drosophila* Whole-Mount Embryos," BioTechniques, vol. 24, No. 4, pp. 530-532, 1998.
Huizenga et al., "A DNA Aptamer That Binds Adenosine and ATP." Biochemistry 34, pp. 656-665, 1995.
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." Cancer Research, vol. 65, No. 19, pp. 8984-8992, Oct. 1, 2005.
Huss, D. et al., "Combinatorial analysis of mRNA expression patterns in mouse embryos using hybridization chain reaction," Cold Spring Harbor Protocols, 11 pages, 2015.
Iqbal, J. et al., "The hybridization chain reaction in the development of ultrasensitive nucleic acid assays," TrAC Trends in Analytical Chemistry, vol. 64, pp. 86-99, Jan. 2015.
International Search Report and Written Opinion from PCT/US2005/009471, dated Mar. 8, 2006.
International Search Report and Written Opinion from PCT/US2008/055559, dated Sep. 3, 2008.
International Search Report and Written Opinion of the International Searching Authority for PCT/US11/31127, dated Oct. 31, 2011.
Iqbal et al., "A review of molecular recognition technologies for detection of biological threat agents", Biosensors & Bioelectronics, vol. 15, pp. 549-578, 2000.
Jagus et al., "PKR, apoptosis and cancer", The International Journal of Biochemistry & Cell Biology, vol. 31, pp. 123-138, 1999.
Jayasena, "Aptamers: An Emerging Class of Molecules That Rival Antiodies in Diagnostics", Clinical Chemistry, vol. 45, No. 9, pp. 1628-1650, 1999.
Jhaveri et al., "In vitro selection of signaling aptamers", Nature Biotechnology, vol. 18, pp. 1293-1297, Dec. 2000.

(56) References Cited

OTHER PUBLICATIONS

Jinek M. et al., "A three-dimensional view of the molecular machinery of RNA interference," Nature, vol. 457, pp. 405-412, 2009.
Johnston et al., "Psoralen-DNA Photoreaction: Controlled Production of Mono- and Diadducts with Nanosecond Ultraviolet Laser Pulses," Science, New Series, vol. 197, No. 4306, pp. 906-908, Aug. 26, 1977.
Jonoska et al., "DNA cages with icosahedral symmetry bionanotechnology," Algorithmic Bioprocesses, 2008.
Judge et al., "Design of Noninflammatory Synthetic siRNA Mediating Potent Gene Silencing in Vivo." Molecular Therapy, vol. 13.3, pp. 494-505., Mar. 2006.
Judge et al., "Overcoming the Innate Immune Response to Small Interfering RNA", Human Gene Therapy, vol. 19, pp. 111-124, Feb. 2008.
Julian et al., "Biomimetic Approaches to Gas Phase Peptide Chemistry: Combining Selective Binding Motifs with Reactive Carbene Precursors to Form Molecular Mousetraps." International Journal of Mass Spectrometry, vol. 228, pp. 851-864, 2003.
Julian et al., "Molecular Mousetraps: Gas-Phase Studies of the Covalent Coupling of Noncovalent Complexes Initiated by Reactive Carbenes Formed by Controlled Activation of Diazo Precursors." Agnew. Chem.Int. Ed., vol. 42.9, pp. 1012-1015, 2003.
Jung, C. et al., "Diagnostic applications of nucleic acid circuits," Accounts of Chemical Research, vol. 47, No. 6, pp. 1825-1835, 2014.
Kadnikov et al., "Synthesis of Coumarins via Palladium-Catalyzed Carbonylative Annulation of Internal Alkynes by o-Iodophenols." Organic Letters, vol. 2.23, pp. 3643-3646, 2000.
Ke et al. "Scaffolded DNA Origami of a DNA Tetrahedron Molecular Container," Nanoletters, vol. 9, No. 6, pp. 2445-2447, 2009.
Kerstens, H.M. et al., "A novel in situ hybridization signal amplification method based on the deposition of biotinylated tyramine," The Journal of Histochemistry and Cytochemistry, vol. 43, No. 4, pp. 347-352, 1995.
Killops, K.L., Campos, L.M., Hawker, C.J., "Robust, Efficient, and Orthogonal Synthesis of Dendrimers via Thiol-ene "Click" Chemistry," Journal of the American Chemical Society, vol. 130, pp. 5062-5064, 2008.
Kim J. et al., "Construction of an in vitro bistable circuit from synthetic transcriptional switches." Mol Syst Biol, vol. 2, pp. 68, 2006.
Kim et al., "Strategies for Silencing Human Disease Using RNA Interference." Nature Review Genetics, vol. 8, pp. 173-184, Mar. 2007.
Kim et al., "Synthetic dsRNA Dicer substrates enhance RNAi potency and efficacy", Nature Biotechnology, vol. 23, No. 2, pp. 222-226, Feb. 2005.
Kislauskis, E.H. et al., "Isoform-specific 3'-untranslated sequences sort alpha-cardiac and beta-cytoplasmic actin messenger RNAs to different cytoplasmic compartments," The Journal of Cell Biology, vol. 123, No. 1, pp. 165-172, Oct. 1993.
Knorre et al., "Photoaffinity Labeling as an Approach to Study Supramolecular Nucleoprotein Complexes." FEBS Letters, vol. 433, pp. 9-14, 1998.
Kobertz et al., "An Efficient Synthesis of a Furan-Side Furocoumarin Thymidine Monoadduct." J. Org. Chem., vol. 62.8, pp. 2630-2632, 1997.
Kobertz et al., "Solid-Phase Synthesis of Oligonucleotides Containing a Site-Specific Psoralen Derivative." Journal of American Chemical Society, vol. 119, pp. 5960-5961, 1997.
Kobertz et al., "Total Synthesis of a Cis-Syn 2-Carbomethoxypsoralen Furan-Side Thymidine Monoadduct." Journal of American Chemical Society, vol. 118, pp. 7101-7107, 1996.
Kosman, D. et al., "Multiplex detection of RNA expression in *Drosophila* embryos," Science, vol. 305, Issue 5685, pp. 846, Aug. 6, 2004.
Kumar, D. et al., "Combinatorially inducible RNA interference triggered by chemically modified oligonucleotides," J Am Chem Soc, vol. 133, pp. 2783-2788, 2011.
Kumar, D. et al., "Conditional RNA interference mediated by allosteric ribozyme," J Am Chem Soc, vol. 131, pp. 13906-13907, 2009.
Kurreck, J. Angew. "RNA interference: from basic research to therapeutic applications" Chem., Int. Ed., vol. 48, pp. 1378-1398, 2009.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." Nucleosides, Nucleotides, and Nucleic Acids, vol. 25, pp. 9-15, 2006.
Ladiges et al., "Tissue specific expression of PKR protein kinase in aging B6D2F1 mice," Mechanisms of Ageing and Development, vol. 114, pp. 123-132, 2000.
Larsson, C. et al., "In situ detection and genotyping of individual mRNA molecules," Nature Methods, vol. 7, pp. 395-397, May 1, 2010.
Larsson, C. et al., "In situ genotyping individual DNA molecules by target-primed rolling-circle amplification of padlock probes," Nature Methods, vol. 1, No. 3, pp. 227-232, Dec. 2004.
Lawley et al., "DNA Adducts from Chemotherapeutic Agents." Mutation Research—Fundamental and Molecular mechanisms of Mutagenesis, vol. 355, pp. 13-40, 1996.
Lawrence et al., "Highly Localized Tracks of Specific Transcripts within Interphase Nuclei Visualized by In Situ Hybridization," Cell, vol. 57, pp. 493-502, 1989.
Layzer et al., "In Vivo Activity of Nuclease-Resistant siRNAs," RNA, vol. 10, pp. 766-771, 2004.
Le et al., "DNA-Templated Self-Assembly of Metallic Nanocomponent Arrays on a Surface", Nano Lett., vol. 4, No. 12, pp. 2343-2347, 2004.
Lee et al., "A self-replicating peptide", Nature, vol. 382, pp. 525-528, Aug. 8, 1996.
Lee et al., "Aptamer database" Nucleic Acids Research, vol. 32, pp. D95-100, 2004.
Lee, S. K. et al., "Conditional RNAi: towards a silent gene therapy," Adv. Drug Delivery Rev, vol. 61, pp. 650-664, 2009.
Lehmann, R. et al., "In situ hybridization to RNA," Methods in Cell Biology, vol. 44, pp. 575-598, 1994.
Levsky, J. et al., "Single-cell gene expression profiling," Science, vol. 297, Issue 5582, pp. 836-840, Aug. 2, 2002.
Levy et al., "Exponential growth by cross-catalytic cleavage of deoxyribozymogens", PNAS, vol. 100, No. 11, pp. 6416-6421, May 27, 2003.
Li et al., "Single-chain antibodies against DNA aptamers for use as adapter molecules on DNA tile arrays in nanoscale materials organization." Organic and Biomolecular Chemistry 2006, pp. 3420-3426. 2006.
Li et al., "The structure of FtsZ filaments in vivo suggests a force-generating role in cell division." EMBO J.,vol. 26, pp. 4694-4708. 2007.
Li et al., A new class of homogenous nucleic acid probes based on specific displacement hybridization, Nucleic Acids Research, vol. 30, No. 2e5, pp. 1-9, 2002.
Lima W.F. et al., "Binding and cleavage specificities of human Argonaute2," J Biol Chem, vol. 284, pp. 26017-26028, 2009.
Lin et al., "DNA Tile Based Self-Assembly: Building Complex Nanoarchitectures", ChemPhysChem, vol. 7, pp. 1641-1647, 2006.
Linuma et al., "Polyhedra Self-Assembled from DNA Tripods and Characterized with 3D DNA-PAINT," Science, vol. 344, No. 6179, pp. 65-69, 2014.
Liu et al., "A colorimetric lead biosensor using DNAzyme-directed assembly of gold nanoparticles," J. Am. Chem. Soc., vol. 125, No. 22, pp. 6642-6643, 2003.
Liu et al., "Approaching the Limit: Can One DNA Oligonucleotide Assemble into Large Nanostructures?", Angew. Chem. Int. Ed., vol. 45, pp. 1942-1945, 2006.
Liu et al., "DNA nanotubes self-assembled from triple-crossover tiles as templates for conductive nanowires", PNAS, vol. 101, No. 3, pp. 717-722, Jan. 20, 2004.

(56) References Cited

OTHER PUBLICATIONS

Macechko et al., "Comparison of Immunologic Amplification vs Enzymatic Deposition of Fluorochrome-conjugated Tyramide as Detection Systems for FISH," J Histochem Cytochem, vol. 45, No. 3, pp. 359-363, 1997.
Mahato et al., "Modulation of gene expression by antisense and antigene oligodeoxynucleotides and small interfering RNA", Expert Opin. Drug Deliv., vol. 2, No. 1, pp. 3-28, 2005.
Manche et al., "Interactions between Double-Stranded RNA Regulators and the Protein Kinase DAI", Molecular and Cellular Biology, vol. 12, No. 11, pp. 5238-5248, Nov. 1992.
Manoharan et al., "RNA Interference and Chemically Modified Small Interfering RNAs." Current Opinion in Chemical Biology, vol. 8, pp. 570-579, 2004.
Masu, H. et al., "An activatable siRNA probe: trigger-RNA-dependent activation of RNAi function," Chem., Int. Ed., vol. 48, pp. 9481-9483, 2009.
Mathieu et al., "Six-Helix Bundles Designed from DNA", Nano Lett., vol. 5, No. 4, pp. 661-665, 2005.
Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.
Mathews, David H. et al., "22 predicting rna secondary structure," Cold Spring Harbor Monograph Archive, vol. 43, pp. 631-657, 2006.
McIntyre, G. J. et al., "The effects of stem length and core placement on shRNA activity" BMC Mol. Biol., vol. 12, pp. 34, 2011.
McLennan, R. et al., "Neural crest migration is driven by a few trailblazer cells with a unique molecular signature narrowly confined to the invasive front," Development, vol. 142, pp. 2014-2025, 2015.
Meinhardt et al., "Wavelength-dependent Penetration Depths of Ultraviolet Radiation in Human Skin." Journal of Biomedical Optics, vol. 13.4, pp. 044030-1-044030-5, Jul./Aug. 2008.
Mitchell et al., "Self-Assembly of Chiral DNA Nanotubes", J. Am. Chem. Soc., vol. 126, pp. 16342-16343, 2004.
Mittelstadt et al., "Interaction of human tRNA-dihydrouridine synthase-2 with interferon-induced protein kinase PKR," Nucleic Acids Research, vol. 36, No. 3, pp. 998-1008, 2008.
Mohr et al., "Catalytic Enantioselective Decarboxylative Protonation." Journal of American Chemical Society, vol. 128.35, pp. 11348-11349, 2006.
Mohr et al., "Natural Products as Inspiration for the Development of Asymmetric Catalysis." Nature, vol. 455, pp. 323-332, Sep. 18, 2008.
Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292, American Chemical Society, 2002.
National Science Foundation, "These Cells Will Self-Destruct in Five . . . Four . . . ", Press Release 10-160, p. 1-3, 2010.
Nieto, M. et al., "In situ hybridization analysis of chick embryos in whole mount and tissue sections," Methods in Cell Biology, vol. 51, pp. 219-235, 1996.
Nikolakakis, K. et al., "Use of hybridization chain reaction-fluorescent in situ hybridization to track gene expression by both partners during initiation of symbiosis," Applied and Environmental Microbiology, vol. 81, No. 41, pp. 4728-4735, Jul. 2015.
Noll et al., "Formation and Repair of Interstrand Cross-Links in DNA." Chemical Reviews, vol. 106.2, pp. 277-301, 2006.
Noll et al., "Preparation of Interstrand Cross-Linked DNA Oligonucleotide Duplexes." Frontiers in Bioscience, vol. 9, pp. 421-437, Jan. 1, 2004.
Notice of Allowance dated Apr. 4, 2013 for U.S. Appl. No. 13/363,022.
Notice of Allowance dated Apr. 5, 2017 for U.S. Appl. No. 13/186,228.
Notice of Allowance dated Feb. 20, 2013 for U.S. Appl. No. 12/395,489.
Notice of Allowance dated Jan. 15, 2013 for U.S. Appl. No. 13/363,022.
Notice of Allowance dated Jul. 1, 2014 for U.S. Appl. No. 13/183,331.
Notice of Allowance dated Jun. 26, 2015 for U.S. Appl. No. 12/152,893.
Notice of Allowance dated May 24, 2013 for U.S. Appl. No. 13/016,811.
Notice of Allowance dated Nov. 8, 2016 for U.S. Appl. No. 13/186,228.
Notice of Allowance dated Oct. 8, 2014 for U.S. Appl. No. 13/186,315.
Notice of Allowance dated Oct. 9, 2014 for U.S. Appl. No. 13/154,989.
Notice of Allowance dated Oct. 23, 2013 for U.S. Appl. No. 13/016,811.
Nutiu et al., "Structure-switching signaling aptamers," J. Am. Chem. Soc., vol. 125, pp. 4771-4778, American Chemical Society, 2003.
Office Action dated Apr. 1, 2010 in U.S. Appl. No. 12/467,755.
Office Action dated Apr. 16, 2010 in U.S. Appl. No. 12/454,799.
Office Action dated Apr. 2, 2014 for U.S. Appl. No. 12/467,755.
Office Action dated Aug. 2, 2013 for U.S. Appl. No. 13/186,315.
Office Action dated Aug. 27, 2015 in U.S. Appl. No. 12/467,755.
Office Action dated Aug. 8, 2013 for U.S. Appl. No. 13/186,331.
Office Action dated Dec. 16, 2010 for U.S. Appl. No. 12/395,489.
Office Action dated Feb. 4, 2010 in U.S. Appl. No. 12/152,893.
Office Action dated Feb. 22, 2017 for U.S. Appl. No. 14/497,070.
Office Action dated Feb. 27, 2014 for U.S. Appl. No. 12/454,799.
Office Action dated Jan. 5, 2017 for U.S. Appl. No. 14/033,081.
Office Action dated Jan. 13, 2015 for U.S. Appl. No. 12/467,755.
Office Action dated Jan. 24, 2013 in U.S. Appl. No. 13/186,228, filed Jul. 19, 2011.
Office Action dated Jan. 27, 2014 for U.S. Appl. No. 13/186,315.
Office Action dated Jan. 30, 2014 for U.S. Appl. No. 13/154,989.
Office Action dated Jul. 2, 2015 for U.S. Appl. No. 13/186,228.
Office Action Dated Jul. 8, 2016 for U.S. Appl. No. 13/186,228.
Office Action dated Jun. 22, 2012 for U.S. Appl. No. 13/363,022.
Office Action dated Mar. 10, 2011 in U.S. Appl. No. 12/454,743, filed May 22, 2009.
Office Action dated Mar. 17, 2011 for U.S. Appl. No. 12/611,875.
Office Action dated May 5, 2015 for U.S. Appl. No. 12/454,799.
Office Action dated May 8, 2015 for U.S. Appl. No. 12/467,755.
Office Action dated May 22, 2014 for U.S. Appl. No. 13/186,228.
Office Action dated Nov. 9, 2010 for U.S. Appl. No. 12/040,735.
Office Action dated Oct. 14, 2014 for U.S. Appl. No, 12/152,893.
Office Action dated Oct. 14, 2011 in U.S. Appl. No. 12/454,743, filed May 22, 2009.
Office Action dated Oct. 30, 2014 for U.S. Appl. No. 13/896,235.
Office Action dated Sep. 20, 2012 for U.S. Appl. No. 13/016,811.
Opalinska et al., "Nucleic-Acid Therapeutics; Basic Principles and Recent Applications", Nature Reviews Drug Discovery, vol. 1, pp. 503-514, 2002.
Ouporov, Igor V., and Leontis, Necocles B., "Refinement of the Solution Structure of a Branched DNA Three-Way Junction," Biophysical Journal, vol. 68, pp. 266-274. Jan. 1995.
Park et al, "Programmable DNA Self-Assemblies for Nanoscale Organization of Ligands and Proteins." Nano Letters, vol. 5, pp. 729-733, 2005.
Park et al., "Rapid Identification of Candida dubliniensis Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Patel et al., Cancer Biology & Therapy, vol. 14, No. 8, pp. 693-696; Aug. 2013.
Paul et al., "A self-replicating ligase ribozyme", PNAS, vol. 99, No. 20, pp. 12733-12740, Oct. 1, 2002.
Peng et al., Facile SNP detection using bifunctional, cross-linking oligonucleotide probes, Nucleic Acids Research, vol. 36, No. 5e31, pp. 1-7, 2008.
Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.

(56) References Cited

OTHER PUBLICATIONS

Pernthaler, A. et al., "Fluorescence in situ hybridization and catalyzed reporter deposition for the identification of marine bacteria," Applied and Environmental Microbiology, vol. 68, No. 6, pp. 3094-3101, Jun. 2002.

Pieles, U. and Englisch, U., "Psoralen covalently linked to oligodeoxyribonucleotides: synthesis, sequence specific recognition of DNA and photo-cross-linking to purimidine residues of DNA," Nucleic Acids Research, vol. 17, pp. 285-299, 1989.

Piette, D. et al., "An optimized procedure for whole-mount in situ hybridization on mouse embryos and embryoid bodies," Nature Protocols, vol. 3, No. 7, pp. 1194-1201, 2008.

Piston et al., "Fluorescent protein FRET: the good, the bad and the ugly", Trends Biochem Sci., vol. 32, No. 9, pp. 407-414, Sep. 2007.

Player, A. et al., "Single-copy gene detection using branched DNA (bDNA) in situ hybridization," The Journal of Histochemistry and Cytochemistry, vol. 49, No. 5, pp. 603-611, 2001.

Pouton et al., "Key issues in non-viral gene delivery", Advanced Drug Delivery Reviews, vol. 46, pp. 187-203, 2001.

Provost, P. et al., "Ribonuclease activity and RNA binding of recombinant human Dicer," EMBO J., vol. 21, pp. 5864-5874, 2002.

Qi et al., "Surface Transfer Doping of Diamond (100) by Tetrafluorotetracyanoquinodimethane", J. Am. Chem. Soc., vol. 129, pp. 8084-8085, 2007.

Qian et al., "Recent Developments in Signal Amplification Methods for In Situ Hybridization," Diagnostic Molecular Pathology, vol. 12, No. 1, pp. 1-13, 2003.

Qian, X., L. Jin, and R.V. Lloyd, "In situ hybridization: basic approaches and recent development," The Journal of Histotechnology, vol. 27, No. 1, pp. 53-67, 2004.

Rachofsky et al., "Probing structure and dynamics of DNA with 2-aminopurine: Effects of local environment on fluorescence," Biochemistry, vol. 40, pp. 946-956, 2001.

Raj, A. et al., "Imaging individual mRNA molecules using multiple singly labeled probes," Nature Methods, vol. 5, No. 10, pp. 877-879, 2008.

Read et al., "Barriers to Gene Delivery Using Synthetic Vectors", Advances in Genetics, vol. 53, pp. 19-46, 2005.

Reif et al., "Compact Error-Resilient Computational DNA tiling Assemblies." In Proc. 10.sup.th International Meeting on DNA Computing; 2004.

Reif et al., "Complexity of Graph Self-Assembly in Accretive Systems and Self-Destructible Systems." In Proc. 11.sup.th International Meeting on DNA Computing; 2005.

Reynolds et al., "Rational siRNA Design for RNA Interference." Nature Biotechnology, vol. 22.3, pp. 326-330, Mar. 2004.

Rosen, B. et al., "Whole-mount in situ hybridization in the mouse embryo: gene expression in three dimensions," Trends in Genetics, vol. 9, Issue 5, pp. 162-167, May 1993.

Rosenthal, A. et al., "Localizing transcripts to single cells suggests an important role of uncultured deltaproteobacteria in the termite gut hydrogen economy," PNAS, vol. 110, No. 40, pp. 16163-16168, Oct. 1, 2013.

Rothemund et al., "Algorithmic Self-Assembly of DNA Sierpinski Triangles." PLoS Biology, vol. 2, pp. 2041-2053, 2004.

Rothemund et al., "Design and Characterization of Programmable DNA Nanotubes", J. Am. Chem. Soc., vol. 126, pp. 16344-16352, 2004.

Rothemund et al., "The Program-size complexity of self-assembled squares (extended abstract)." In Proceedings of the thirty-second annual ACM symposium on Theory of computing; ACM Press: 2000.

Rothemund, P.W.K., "Folding DNA to creat nanoscale shapes and patterns", Nature, vol. 440, pp. 297-302, 2006.

Sahu et al., "A Self-Assembly Model of Time-Dependent Glue Strength." In Proc. 11.sup.th International meeting on DNA Computing; 2005.

Sambrook, J. et al., "Molecular cloning: a laboratory manual," Cold Springs Harbor Press, 1989.

Santalucia, J. "A unified view of polymer, dumbbell, and oligonucleotide DNA nearest-neighbor thermodynamics," Proc Natl Acad Sci, vol. 95, pp. 1460-1465, 1998.

Saunders et al., "Introduction of DNA into Bacteria." Methods in Microbiology, vol. 29, pp. 3-49, 1999.

Scharer et al., "DNA Interstrand Crosslinks: Natural and Drug-Induced DNA Adducts that Induce Unique Cellular Responses." ChemBioChem, vol. 6, pp. 27-32, 2005.

Scherer et al., "Approaches for the sequence-specific knockdown of mRNA", Nature Biotechnology, vol. 21, No. 12, pp. 1457-1465, 2003.

Schipani, Vanessa, "A targeted cancer therapy?" The Scientist, Sep. 7, 2010 blog post, http://www.the-scientist.com/blog/display/57674/.

Schulman et al., "Synthesis of crystals with a programmable kinetic barrier to nucleation", PNAS, vol. 104, No. 39, pp. 15236-15241, Sep. 25, 2007.

Schulte-Merker et al., "no tail (ntl) is the zebrafish homologue of the mouse T (Brachyury) gene." Development, vol. 120, pp. 1009-1015, 1994.

Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.

Schweitzer et al., "Combining nucleic acid amplification and detection," Curr Opin Biotechnol, vol. 12, pp. 21-27, 2001.

Seelig et al., "Catalyzed Relaxation of a Metastable DNA Fuel", Journal American Chemical Society, vol. 128, No. 37, pp. 12211-12220, 2006.

Seeman et al., Nucleic Acid Nanostructures: Bottom Up Control of Geometry on the Nanoscale, Reports on Progress in Physics, vol. 68, pp. 237, 2005.

Seeman, "De Novo Design of Sequences for Nucleic Acid Structural Engineering", Journal of Biomolecular Structure & Dynamics, vol. 8, No. 3, pp. 573-581, 1990.

Seeman, "Nucleic acid junctions and lattices," J. Theor. Biol., vol. 99, pp. 237-247, Academic Press Inc. (London) Ltd., 1982.

Seeman, N. C., "DNA in a material world" Nature, vol. 421, No. 23, pp. 427-431, Jan. 23, 2003.

Seeman, N. C., "Nucleic Acid Nanostructures and Topology" Angew. Chem. Int. Ed., vol. 37, pp. 3220-3238, 1998.

Sekulic et al., "A Direct Linkage between the Phosphoinositide 3-Kinase-AKT Signaling Pathway and the Mammalian Target of Rapamycin in Mitogen-stimulated and Transformed Cells," Cancer Research, vol. 60, pp. 3504-3513, 2000.

Serra, M.J. et al., "Predicting thermodynamic properties of RNA," Methods Enzymol., vol. 259, pp. 242-261, 1995.

Shah et al., "The Fries Isomerization of Acetyl and Benzoyl of Umbelliferones." J. Org. Chem. vol. 19, pp. 1681-1685, 1954.

Shah, S. et al., "Single-molecule RNA detection at depth via hybridization chain reaction and tissue hydrogel embedding and clearing," Development, 41 pages, Jun. 2016.

Shaner et al., "A guide to choosing fluorescent proteins", Nature Methods, vol. 2, No. 12, pp. 905-909, Dec. 2005.

Sharma et al., "Control of Self-Assembly of DNA Tubules through Integration of Gold Nanoparticles" Science, pp. 112-116, 2009.

Sharma et al., "DNA-Tile-Directed Self-Assembly of Quantum Dots into Two-Dimensional Nanopatterns", Angew. Chem. Int. Ed., vol. 47, pp. 5157-5159, 2008.

Shih et al., "A 1.7-kilobase single-stranded DNA that folds into a nanoscale octahedron", Nature, vol. 427, pp. 618-621, Feb. 12, 2004.

Shir et al., "Inhibition of glioma growth by tumor-specific activation of double-stranded RNA-dependent protein kinase PKR", Nature Biotechnology, vol. 20, pp. 895-900, Sep. 2002.

Shlyakhtenko et al., "Structure and Dynamics of Three-Way DNA Junctions: Atomic Force Microscopy Studies." Nucleic Acids Research., vol. 28, No. 19, pp. 3472-3477, 2000.

Silverman et al., "Oligonucleotide Probes for RNA-Targeted Fluorescence In Situ Hybridization." Advances in Clinical Chemistry, vol. 43, pp. 79-115, 2007.

(56) References Cited

OTHER PUBLICATIONS

Silverman et al., "Quenched Autoligation Probes Allow Discrimination of Live Bacterial Species by Single Nucleotide Differences in rRNA." Nucleic Acids Research, vol. 33.15, pp. 4978-4986, 2005.
Singleton, P. et al., "Dictionary of Microbiology and Molecular Biology," 2nd Edition, J. Wiley & Sons, 1994.
Siolas et al., "Synthetic shRNAs as Potent RNAi Triggers." Nature Biotechnology, vol. 23.2, pp. 227-231, Feb. 2005.
Situma et al., "Immobilized molecular beacons: A new strategy using UV-activated poly(methyl methacrylate) surfaces to provide large fluorescence sensitivities for reporting on molecular association events." Analytical Biochemistry, vol. 363, pp. 35-45, 2007.
Sokol et al., "Real time detection of DNA.circle-solid.RNA hybridization in living cells", Proc. Natl. Acad. Sci. USA, vol. 95, pp. 11538-11543, Sep. 1998.
Stratagene Catalog. gene characterization kits. Stratagene Catalog, pp. 39, 1988.
Stemmer et al, "Single Step Assembly of a Gene and Entire Plasmid from Large Numbers of Oligodeoxyribonnucleotides," Gene, vol. 164, pp. 49-53, 1995.
Storhoff et al., "One-pot colorimetric differentiation of polynucleotides with single base imperfections using gold nanoparticles," J. Am. Chem. Soc., vol. 120, pp. 1959-1964, 1998.
Stuheimer et al. "Global Structure of Three-Way DNA Junctions with and without Additional Unpaired Bases: A Fluorescence Resonance Energy Transfer Analysis". Biochemistry, vol. 35, pp. 13530-13538, 1997.
Sun et al., "Side Chain Chemistry Mediates Backbone Fragmentation in Hydrogen Deficient Peptide Radicals, " Journal of Proteome Research, vol. 8, pp. 958-966, 2009.
Supplementary European Search Report from PCT/US2005/009471, dated May 6, 2008.
Supplemental Notice of Allowance dated Sep. 17, 2015 for U.S. Appl. No. 12/152,893.
Takei et al., "A Small Interfering RNA Targeting Vascular Endothelial Growth Factor as Cancer Therapeutics." Cancer Research, vol. 64, pp. 3365-3370, May 15, 2004.
Tani et al., "Synthesis and Structural Analysis of 2-Quinuclidonium Tetrafluoroborate." Nature, vol. 441, pp. 731-734, Jun. 8, 2006.
Tautz, D. et al., "A non-radioactive in situ hybridization method for the localization of specific RNAs in *Drosophila* embryos reveals translational control of the segmentation gene hunchback," Chromosoma, vol. 98, Issue 2, pp. 81-85, Aug. 1989.
The Naked Scientists: Science Radio & Science Podcasts, "RNA-away cancer cells", Sep. 12, 2010, http://www.thenakedscientists.com/HTML/content/news/news/2051/.
Thisse, B., "Spatial and temporal expression of the zebrafish genome by large-scale in situ hybridization screening," Methods in Cell Biology, vol. 77, pp. 505-519, 2004.
Thisse, C. et al., "High-resolution in situ hybridization to whole-mount zebrafish embryos," Nature Protocols, vol. 3, No. 1, pp. 59-69, Jan. 2008.
Thomas et al., "Photoaffinity Cross-Linking and RNA Structure Analysis." Methods in Enzymology, vol. 318, pp. 136-147, 2000.
Thompson et al, "Recent advances in fluorescence correlation spectroscopy." Curr. Opin.Struct. Biol., 12, 2002.
Tijsterman et al., "Dicers at RISC: The Mechanism of RNAi", Cell, vol. 117, pp. 1-3, 2004.
Tuerk, C. et al., "Systematic evolution of ligands by exponential enrichment: RNA ligands to bacteriophage T4 DNA polymerase," Science, vol. 249, No. 4968, pp. 505-510, Aug. 3, 1990.
Tuleuova, N. et al., "Modulating endogenous gene expression of mammalian cells via RNA-small molecule interaction," Biochem. Biophys. Res. Commun., vol. 376, pp. 169-173, 2008.
Turberfield et al,, "DNA fuel for free-running nanomachines, "Physical Review Letters, vol. 90, No. 11, pp. 118102-1-118102-4, Mar. 21, 2003.
Turk et al., "Zippered polygon meshes from range images." In SIGGRAPH, pp. 311-318, 1994.

Tyagi et al., "Multicolor Molecular Beacons for Allele Discrimination," Nature Biotechnology, vol. 16, pp. 49-53, Jan. 1998.
Tyagi, S. et al., "Molecular Beacons: Probes that Fluoresce upon Hybridization," Nature Biotechnology, vol. 14, pp. 303-308, Mar. 1996.
U.S. Appl. No. 14/497,070, filed Sep. 25, 2014, Wolfe et al.
U.S. File History printed Jun. 16, 2009 for U.S. Appl. No. 11/087,937, filed Mar. 22, 2005, entitled "Hybridization Chain Reaction."
U.S. File History printed Jun. 16, 2009 for U.S. Appl. No. 11/371,346, filed Mar. 7, 2006, entitled "Hybridization Chain Reaction Amplification for In Situ Imaging.".
U.S. File History printed Jun. 16, 2009 for U.S. Appl. No. 11/371,347, filed Mar. 7, 2006, entitled "Colorimetric Readout of Hybridization Chain Reaction."
U.S. File History printed Jun. 16, 2009 for U.S. Appl. No. 11/544,306, filed Oct. 6, 2006, entitled "PKR Activation Via Hybridization Chain Reaction."
U.S. File History printed Jun. 16, 2009 for U.S. Appl. No. 12/040,735, filed Feb. 29, 2008, entitled "Triggered RNAi."
U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways."
U.S. File History printed Jun. 4, 2010 for U.S. Appl. No. 12/395,489, filed Feb. 27, 2009, entitled "Triggered RNAi."
U.S. File History printed Jun. 4, 2010 for U.S. Appl. No. 12/454,743, filed May 22, 2009, entitled "Triggered RNAi."
U.S. File History printed Jun. 4, 2010 for U.S. Appl. No. 12/454,799, filed May 22, 2009, entitled "Compositions and Methods for Detecting Analytes."
U.S. File History printed Jun. 4, 2010 for U.S. Appl. No. 12/467,755, filed May 18, 2009, entitled "Shielded Cross-Linking Probes."
U.S. File History printed Jun. 4, 2010 for U.S. Appl. No. 12/611,875, filed Nov. 3, 2009, entitled "Hybridization Chain Reaction."
Van De Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, vol. 46, No. 11, pp. 1249-1259, 1998.
Venkataraman et al. "Selective Cell Death Mediated by Small Conditional RNAs", Proc Natl Acad Sci USA, early edition, approved Jul. 21, 2010, p. 1-6.
Venkataraman et al. Abstract of "Selective Cell Death Mediated by Small Conditional RNAs", Proc Natl Acad Sci USA, early edition, http://www.pnas.org/content/early/2010/09/01/1006377107.abstract.
Venkataraman et al., "An Autonomous Polymerization Motor Powered by DNA Hybridization." Nature Nanotechnology, vol. 2, pp. 490-494, Aug. 2007.
Vermeulen et al., "The contributions of dsRNA structure to Dicer specificity and efficiency", RNA, vol. 11, pp. 674-682, 2005.
Vieregg et al., "Selective Nucleic Acid Capture with Shielded Covalent Probes", J. Am. Chem. Soc., vol. 135, pp. 9691-9699, 2013.
Vieregg et al., "Selective Nucleic Acid Capture with Shielded Covalent Probes—Supplemental Materials", J. Am. Chem. Soc., vol. 135, pp. S1-S52, 2013.
Vodovozova et al., "Photoaffinity Labeling and its Application in Structural Biology." Biochemistry (Moscow), vol. 72.1, pp. 1-20, 2007.
Volker et al., "Conformational energetics of stable and metastable states formed by DNA triple repeat oligonucleotides: implications for triplet expansion diseases," PNAS, vol. 99, No. 23, pp. 14700-14705, Nov. 12, 2002.
Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" Trends in Biotechnology, vol. 21.1, pp. 2-4, Jan. 2003.
Wagner et al., "Transferrin-Polycation Conjugates as Carriers for DNA Uptake into Cells", Proceedings of the National Academy of Sciences of the United States of America, vol. 87, pp. 3410-3414, May 1990.

(56) References Cited

OTHER PUBLICATIONS

Wallner, G. et al., "Optimizing fluorescent in situ hybridization with rRNA-targeted oligonucleotide probes for flow cytometric identification of microorganisms," Cytometry, vol. 14, Issue 2, pp. 136-143, 1993.
Wang, F. et al., "RNAscope: A novel in situ RNA analysis platform for formalin-fixed, paraffin-embedded tissues," The Journal of Molecular Diagnostics, vol. 14, No. 1, pp. 22-29, Jan. 2012.
Wang, F., "From Cascaded Catalytic Nucleic Acids to Enzyme-DNA Nanostructures: Controlling Reactivity, Sensing, Logic Operations, and Assembly of Complex Structures," Chemical Reviews, vol. 114, No. 5, pp. 2881-2941, 2014.
Wassarman et al., "Psoralen Crosslinking of Small RNAs in vitro." Molecular Biology Reports, vol. 17, pp. 143-151, 1993.
Weiszmann, R. et al., "Determination of gene expression patterns using high-throughput RNA in situ hybridization to whole-mount *Drosophila* embryos," Nature Protoc., vol. 4, No. 5, pp. 605-618, 2009.
White et al., "The Catalytic Asymmetric Total Synthesis of Elatol." Journal of American Chemical Society, vol. 130.3, pp. 810-811, 2008.
Wiedorn, K.H. et al., "Comparison of in-situ hybridization, direct and indirect in-situ PCR as well as tyramide signal amplification for the detection of HPV," Histochemistry and Cell Biology, vol. 111, Issue 2, pp. 89-95, Jan. 1999.
Wijen et al., "The in vivo Genetic Activity Profile of the Monofunctional Nitrogen Mustard 2-Chloroethylamine Differs Drastically from its Bifunctional Counterpart Mechlorethamine." Carcinogenesis, vol. 21.10, pp. 1859-1867, 2000.
Wilkie et al., "Transcribed genes are localized according to chromosomal position within polarized *Drosophila* embryonic nuclei," Current Biology, vol. 9, pp. 1263-1266, 1999.
Williams, B.R.G., "PKR; a sentinel kinase for cellular stress", Oncogene, vol. 18, pp. 6112-6120, 1999.
Willis, M.C., et al., "Photocross-linking of 5-Iodouracil-Substituted RNA and DNA to Proteins," Science, vol. 262, pp. 1255-1257, 1993.
Winfree et al., "Design and self-assembly of two-dimensional DNA crystals", Nature, vol. 394, pp. 539-544, Aug. 6, 1998.
Winfree, E., "Algorithmic Self-Assembly of DNA, Ph.D. thesis", Thesis, California Institute of Technology, 1998.
Winfree, E., "On the computational power of DNA annealing and ligation." Computation and Neural Systems, California Institute of Technology, May 25, 1995.
Wiznerowicz, M. et al., "Tuning silence: conditional systems for RNA interference," Nat. Methods, vol. 3, pp. 682-688, 2006.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Xie, Z. et al., "Logic integration of mRNA signals by an RNAi-based molecular computer" Nucleic Acids Res., vol. 38, pp. 2692-2701, 2010.
Yamaguchi, T. et al., "In situ DNA-hybridization chain reaction (HCR): a facilitated in situ HCR system for the detection of environmental microorganisms," Environmental Microbiology, vol. 17, Issue 7, pp. 2532-2541, Jul. 2015.
Yan et al., "DNA Templated Self-Assembly of Protein Arrays and Highly Conductive Nanowires", Science, vol. 301, pp. 1882-1884, Sep. 26, 2003.
Yin et al, "Programming DNA Tube Circumferences." Science, vol. 321, pp. 824-826, 2008.
Yin et al., "A Unidirectional DNA Walker that Moves Autonomously along a Track." Angewandte Chemie International Edition, vol. 43, pp. 4906-4911, 2004.
Yin et al., "Designs of Autonomous Unidirectional Walking DNA Devices." In Proc. 10.sup.th International Meeting on DNA computing; 2004.
Yin et al., "Programming biomolecular self-assembly pathways", Nature, vol. 451, pp. 318-323, Jan. 17, 2008.
Yin et al., "Theoretical and practical advances in genome halving." A.K. Bioinformatics, vol. 21, pp. 869-879, 2005.
Yoshimura et al., "Interstrand Photocrosslinking of DNA via p-carbamoylvinyl Phenol Nucleoside." Bioorganic & Medicinal Chemistry Letters, vol. 15, pp. 1299-1301, 2005.
Yurke et al., "A DNA-fuelled molecular machine made of DNA" Nature, vol. 406, pp. 605-608, Aug. 10, 2000.
Zadeh, "Algorithms for nucleic acid sequence design," Doctoral Thesis [online] orally defended Dec. 8, 2009 (Dec. 8, 2009), published May 25, 2010 (May 25, 2010), [Retrieved on Jun. 7, 2011], pp. 1-85, Retrieved from the Internet: <URL: http://resolver.caltech.edu/CaltechTHESIS:05112010-205335518>.
Zadeh, "Algorithms for nucleic acid sequence design," Doctoral Thesis, defenced Dec. 8, 2009; Abstract only [online]; downloaded from URL: http://thesis.library.caltech.edu/5801/ on Jul. 6, 2011.
Zadeh et al., "Nucleic acid sequence design via efficient ensemble defect optimization," J. Comput. Chem., vol. 32, pp. 439-452, 2011.
Zadeh et al., "Software News and Updates NUPACK: Analysis and Design of Nucleic Acid Systems", Journal of Computational Chemistry, vol. 32, No. 1, pp. 170-173, 2011.
Zhang et al., "Conformational flexibility facilitates self-assembly of complex DNA nanostructures," PNAS, vol. 105, No. 31, pp. 10665-10669, 2008.
Zhang et al., "Gene expression profiles in normal and cancer dells." Science, vol. 276, pp. 1268-1272, 1997.
Zhang et al., Targeted Gene Silencing by Small Interfering RNA-Based Knock-Down Technology, Current Pharmaceutical Biotechnology, vol. 5, pp. 1-7, 2004.
Zhang, D. Y. et al., "Dynamic DNA nanotechnology using strand-displacement reactions," Nat. Chem., vol. 3, pp. 103-113, 2011.
Zhang, H.Q. et al., "DNA-mediated homogeneous binding assays for nucleic acids and proteins," Chemical Reviews, vol. 113, No. 4, pp. 2812-2841, 2013.
Zheng et al., "Activtion of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zhou, H. et al., "Two-color, rolling-circle amplification on antibody microarrays for sensitive, multiplexed serum-protein measurements," Genome Biology, vol. 5, Issue 4, Article R28, pp. R28.1-R28.12, 2004.
Zuker et al., "Optimal computer folding of large RNA sequence using thermodynamics and auxiliary information," Nucleic Acids Research, vol. 9, No. 1, pp. 133-147, 1981.
Abudayyeh,.O et al. C2c2 is a single-component programmable RNA-guided RNA-targeting CRISPR effector, Science, (2016).
Barrangou, R, et al., 2007. 'CRISPR Provides Acquired Resistance Against Viruses in Prokaryotes', Science, 315, pp. 1709-1712, (2007).
Bouchard, H, et al., Antibody-drug conjugates: A new wave of cancer drugs. Bioorganic & Medicinal Chemistry Letters, vol. 24, No. 23, pp. 5357-5367, (2014).
Chen, B et al. 'Dynamic Imaging of Genomic Loci in Living Human Cells by an Optimized CRISPR/Cas System', Cell, 155: 1479-91, (2013.
Chen, Y et al. Profiling of Multiple Glycans on Whole Living Cell Suraces, Analytical Chemistry, vol. 85, No. 22, pp. 11153-11158, (2013).
Cong, L. et al. 'Multiplex Genome Engineering Using CRISPR/Cas Systems', Science, 339: 819-23, (2013).
De Matos, et al., Heparanase expression in lung carcinoid tumors by immunohistochemistry. Ejc Supplements , vol. 3, No. 2, pp. 342 (2005).
Dicarlo, J et al.. 'RNA-guided gene drives can efficiently bias inheritance in wild yeast', bioRxiv, (2015).
Gilbert, L. et al. 'CRISPR-Mediated Modular RNA-Guided Regulation of Transcription in Eukaryotes', Cell, 154: 442-51, (2013).

(56) References Cited

OTHER PUBLICATIONS

Horvath, P et al.. 'CRISPR/Cas, the Immune System of Bacteria and Archaea', Science, 327: 167-70, (2010).
Jinek,M et al.. 'A Programmable Dual-RNA-Guided DNA Endonuclease in Adaptive Bacterial Immunity', Science, 337: 816-21, (2012).
Lin, F. et al., Standardization of Diagnostic Immunohistochemistry Literature Review and Geisinger Experience, Archives of Pathology & Laboratory Medicine, vol. 138.
Mali, P et al . . . 'RNA-Guided Human Genome Engineering via Cas9', Science, 339: 823-26., (2013).
Qi, L. et al.. 'Repurposing CRISPR as an RNA-Guided Platform for Sequence-Specific Control of Gene Expression', Cell, 152: 1173-83. (2013).
Sander, J. et al., 'CRISPR-Cas systems for editing, regulating and targeting genomes', Nat Biotech, 32: 347-55., (2014).
Shlyakhtenko et al., "Structure of Three-Way DNA Junctions 1. Non-Planar DNA Geometry" Journal of Biomolecular Structure and Dynamics, vol. 11: pp. 1175-1189, Nov. 6, 1994.
Stack, E., et al. Multiplexed immunohistochemistry, imaging, and quantitation: A review, with an assessment of Tyramide signal amplification, multispectral imaging and multiplex analysis, . Methods, vol. 70, No. 1, (2014).
Trail, P., Antibody drug conjugates as cancer therapeutics, Antibodies, vol. 2, No. 1 pp. 113-129, (2013).
Zhang, H. et al., DNA-Mediated Homogeneous Binding Assays for Nucleic Acids and Proteins, Chemical Reviews vol. 113, No. 4, pp. 2812-2841, (2013).
International Search Report and Written Opinion dated Nov. 6, 2017 in International Application No. PCT/US2017/49198.
International Search Report and Written Opinion dated Feb. 5, 2018 in International Application No. PCT/US2017/040485.
Notice of Allowance dated Feb. 5, 2013 for U.S. Appl. No. 13/079,747.
Final Office Action dated Feb. 7, 2017 for U.S. Appl. No. 14/320,479.
Office Action dated Oct. 12, 2016 for U.S. Appl. No. 14/320,479.
Response to Office Action filed on Jan. 12, 2017 in U.S. Appl. No. 14/320,479.
Office Action dated Jan. 4, 2016 in U.S. Appl. No. 13/186,228.
Restriction Requirement dated Feb. 23, 2006 in U.S. Appl. No. 11/087,937.
Office Action dated Apr. 27, 2006 in U.S. Appl. No. 11/087,937.
Office Action dated Mar. 1, 2007 in U.S. Appl. No. 11/087,937.
Office Action dated Aug. 23, 2007 in U.S. Appl. No. 11/087,937.
Office Action dated Mar. 25, 2008 in U.S. Appl. No. 11/087,937.
Office Action dated Sep. 26, 2008 in U.S. Appl. No. 11/087,937.
Office Action dated Apr. 30, 2008 in U.S. Appl. No. 11/371,347.
Office Action dated Dec. 3, 2008 in U.S. Appl. No. 11/371,347.
Office Action dated Mar. 26, 2008 in U.S. Appl. No. 11/371,346.
Office Action dated Oct. 16, 2008 in U.S. Appl. No. 11/371,346.
Office Action dated Mar. 20, 2009 in U.S. Appl. No. 11/371,346.
Office Action dated Sep. 29, 2009 in U.S. Appl. No. 11/371,346.
Office Action dated Sep. 21, 2011 in U.S. Appl. No. 12/790,379.
Office Action dated Feb. 8, 2008 in U.S. Appl. No. 11/544,306.
Office Action dated Oct. 15, 2008 in U.S. Appl. No. 11/544,306.
Office Action dated Mar. 19, 2009 in U.S. Appl. No. 11/544,306.
Office Action dated Sep. 2, 2009 in U.S. Appl. No. 11/544,306.
Office Action dated Dec. 24, 2009 in U.S. Appl. No. 11/544,306.
Office Action dated Jul. 2, 2012 in U.S. Appl. No. 13/079,747.
Notice of Allowance dated Apr. 25, 2017 in U.S. Appl. No. 14/320,479.
Notice to File Corrected Application Papers dated May 22, 2017 in U.S. Appl. No. 14/320,479.
Notice Regarding IDS dated May 25, 2017 in U.S. Appl. No. 14/320,479.
Interview Summary dated Jun. 21, 2017 in U.S. Appl. No. 14/320,479.
Interview Summary dated Mar. 29, 2017 in U.S. Appl. No. 14/033,081.
Notice of Allowance dated Jul. 31, 2017 for U.S. Appl. No. 13/186,228.
Notice of Allowance dated Aug. 24, 2017 in U.S. Appl. No. 14/320,479.
Antano et al., In Situ Hybridization Using the BDNA, Techniques in Quantification and Localization of Gene Expression, pp. 81-93, 2000.
Collins et al., A branched DNA signal amplification assay for quantification of nucleic acid targets below 100 molecules/ml, Nucleic Acids Research, vol. 25, No. 15, pp. 2979-2984, 1997.
Hodinka et al., The clinical utility of viral quantitation using molecular methods, Clinical and Diagnostic Virology, vol. 10, No. 1, pp. 25-47, 1998.
Kenny et al., Detection of Viral Infection and Gene Expression in Clinical Tissue Specimens Using Branched DNA (BDNA) In Situ Hybridization, vol. 50, No. 9, pp. 1219-1227, 2002.
Kern et al., An Enhanced-Sensitivity Branched-DNA Assay for Quantification of Human Immunodeficiency Virus Type 1 RNA in Plasma, Journal of Clinical Microbiology, vol. 34, No. 12, pp. 3196-3202, 1996.
Leisinger, B. Viral Load Testing for HIV Beyond the CD4 Count, Laboratory Medicine, vol. 30, No. 2, pp. 102-109, 1999.
Nolte, et al., Branched DNA Signal Amplification for Direct Quantitation of Nucleic Acid Sequences in Clinical Specimens, Advances in Clinical Chemistry, vol. 33, pp. 201-235, 1998.
Nolte et al., Clinical Comparison of an Enhanced-Sensitivity Branched-DNA Assay and Reverse Transcription-PCR for Quantitation of Human Immunodeficiency Virus Type 1 RNA in Plasma, Journal of Clinical Microbiology, vol. 36, No. 3, pp. 716-720, 1998.
Ross et al., Quantitation of hepatitis C virus RNA by third generation branched DNA-based signal amplification assay, Journal of Virological Methods, vol. 101, No. 1-2, pp. 159-168, 2002.
Trimoulet et al., Evaluation of the VERSANT HCV RNA 3.0 Assay for Quantification of Hepatitis C Virus RNA in Serum, Journal of Clinical Microbiology, vol. 40, No. 6, pp. 2031-2036, 2002.
Tsongalis et al., Branched DNA Technology in Molecular Diagnostics, American Journal of Clinical Pathology, vol. 126, No. 3, 448-453, 2006.
Bayer Versant® HIV-1 RNA 3.0 Assay (bDNA) FDA coversheet (approval date 2002).
Bayer Versant® HIV-1 RNA 3.0 Assay (bDNA) FDA Summary of Safety and Effectiveness (approval date 2002).
Bayer Versant® HCV RNA 3.0 Assay (bDNA) product manual (date 2003).
Wang et al., Signal Amplification Techniques: BDNA, Hybrid Capture, Advanced Techniques in Diagnostic Microbiology, pp. 228-242, 2006.
Office Action dated Nov. 9, 2018 in U.S. Appl. No. 15/689,786.
International Preliminary Report on Patentability dated Jan. 17, 2019 in International Application No. PCT/US2017/040485.
International Preliminary Report on Patentability dated Mar. 15, 2019 in International Application No. PCT/US2017/49198.
International Search Report and Written Opinion dated Apr. 18, 2019 I n Internatioanl Applicatio No. PCT/US2018/036969.
Office Action dated Mar. 19, 2019 in U.S. Appl. No. 15/689,786.
File History of U.S. Appl. No. 15/689,786.
File History of U.S. Appl. No. 16/005,445.

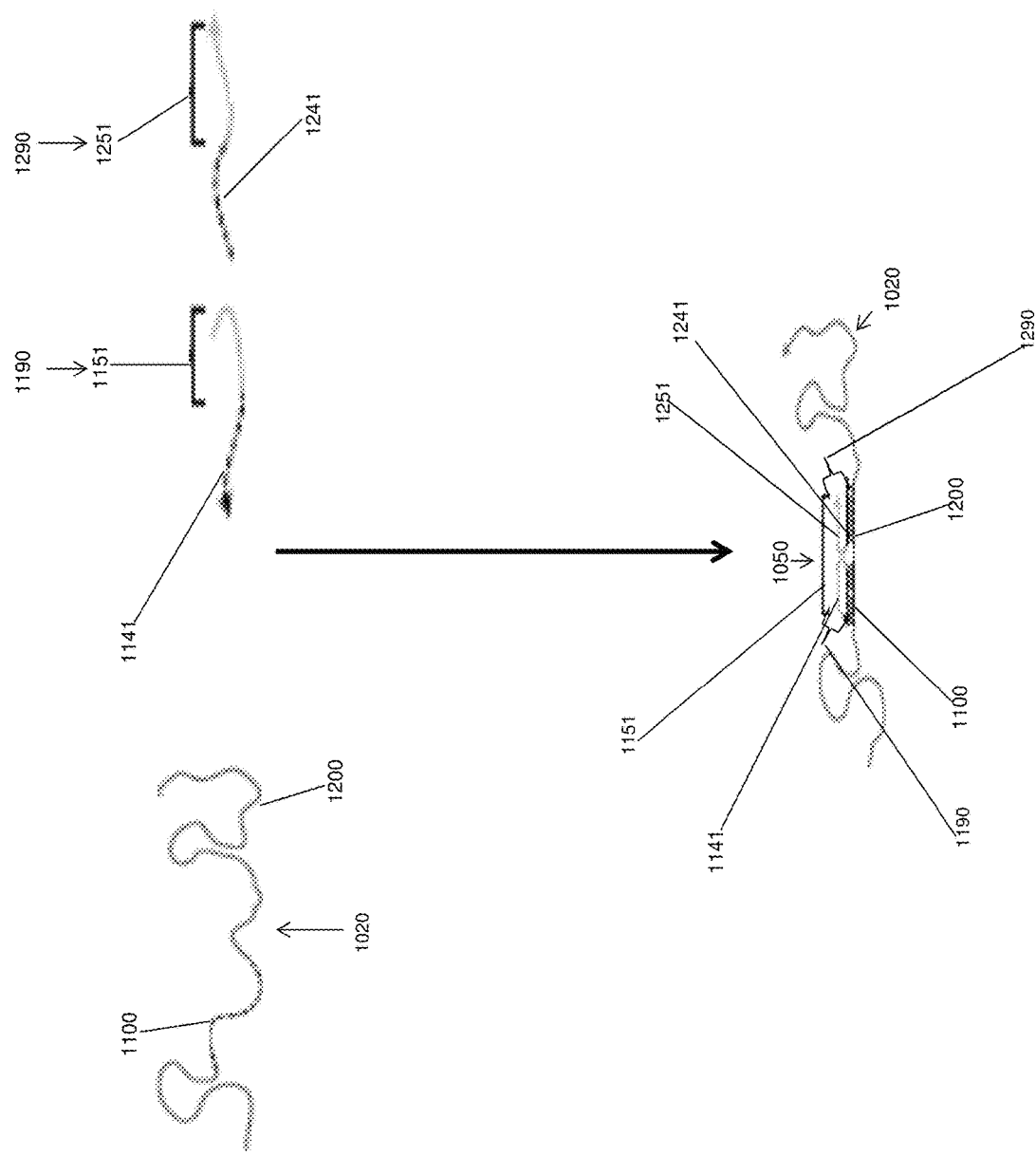

FRACTIONAL INITIATOR HYBRIDIZATION CHAIN REACTION

REFERENCE TO RELATED APPLICATIONS

This application claims priority to U.S. Provisional Patent Application No. 62/358,462, filed Jul. 5, 2016, the disclosure of which is hereby incorporated by reference in its entirety herein.

STATEMENT REGARDING FEDERALLY SPONSORED R&D

This invention was made with government support under Grant No. EB006192 awarded by the National Institutes of Health and Grant No. CCF1317694 awarded by the National Science Foundation and from DARPA under grant HR0011-17-2-0008. The government has certain rights in the invention.

BACKGROUND

Field

The present invention relates generally to compositions and methods relating to the use of hybridization chain reaction.

Description of the Related Art

Hybridization Chain Reaction (HCR) is a method for the triggered self-assembly of nucleic acid molecules starting from metastable hairpin monomers or other more complicated nucleic acid structures. In a simple version of this process, metastable hairpin monomers undergo a chain reaction of hybridization events to form a nicked double-stranded polymer when triggered by a nucleic acid initiator strand. The hairpin monomers store the energy to drive the polymerization process in their single-stranded loops and toeholds.

SUMMARY

In some embodiments, a composition is provided that comprises: a first hairpin monomer; a second hairpin monomer; a first fractional initiator probe comprising a first fractional initiator; and a second fractional initiator probe comprising a second fractional initiator.

In some embodiments, a composition is provided, comprising:
a first hairpin monomer, comprising:
  i. a first input domain, comprising a first toehold and a first stem section,
  ii. a first output domain, comprising a first hairpin loop and a complement to the first stem section, and
  iii. a first reporter molecule;
a second hairpin monomer, comprising:
  iv. a second input domain, comprising a second toehold and a second stem section,
  v. a second output domain, comprising a second hairpin loop and a complement to the second stem section,
  vi. a second reporter molecule;
a first fractional initiator probe comprising a first fractional initiator; and
a second fractional initiator probe comprising a second fractional initiator.

In some embodiments a composition is provided, wherein the first stem section can have a same sequence as the second stem section. In some embodiments a composition is provided, wherein the complement to the first stem section can have a same sequence as the complement to the second stem section. In some embodiments a composition is provided, wherein the first stem section can have a same sequence as the second stem section.

In some embodiments a composition is provided wherein the first toehold is complementary to the second hairpin loop. In some embodiments a composition is provided wherein the second toehold is complementary to the first hairpin loop.

In some embodiments a composition is provided that further comprises a target molecule comprising a first target section and a second target section.

In some embodiments a composition is provided wherein the first fractional initiator probe further comprises a first target binding section and the second fractional initiator probe further comprises a second target binding section, wherein the first target binding section is configured to bind to the first target section and the second target binding section is configured to bind to the second target section.

In some embodiments a method is provided that comprises:
  a. providing:
    i. a first fractional initiator probe
    ii. a second fractional initiator probe
    iii. a first hairpin monomer
    iv. a second hairpin monomer, and
    v. a target molecule;
  b. incubating to allow for binding; and
  c. detecting a signal.

In some embodiments a method is provided wherein the target molecule comprises a nucleotide.

In some embodiments a method is provided wherein the first fractional initiator probe and the second fractional initiator probe are combined with the target molecule.

In some embodiments a method is provided, wherein unbound first fractional initiator probe and unbound second fractional initiator probe are removed from a sample containing the target molecule by a first wash.

In some embodiments a method is provided, wherein following the first wash, colocalized first and second initiator probes on the target molecule are bound by the first hairpin monomer, which is then bound by the second hairpin monomer, resulting in HCR amplification.

In some embodiments a method is provided wherein unbound hairpin monomer is washed from the sample containing the target molecule.

In some embodiments a method is provided wherein an alternating cascade of the first hairpin monomer binding and the second hairpin monomer binding provides a polymerization event.

In some embodiments a method of performing HCR is provided, the method comprising: adding a first fractional initiator and a second fractional initiator to a sample, wherein together the first and the second fractional initiators provide a full HCR initiator; and adding a set of HCR hairpin monomers to the sample so as to allow HCR to occur in the presence of the full HCR initiator.

In some embodiments a method is provided, wherein the first fractional initiator is part of a first fractional initiator probe and wherein the second fractional initiator is part of a second fractional initiator probe.

In some embodiments a method is provided, wherein the method is part of an in situ process to image DNA, RNA, protein, or small molecule targets, including DNA in situ hybridization (ISH), RNA in situ hybridization (ISH), protein immunohistochemistry (IHC).

In some embodiments a method is provided, wherein the method comprises a 2-stage approach with a wash after each stage, and wherein the target is immobilized, and wherein the sample is fixed.

In some embodiments a method is provided wherein a first stage is a detection stage that comprises binding probes to a target and washing away unbound probe, and wherein a second stage is an amplification stage, wherein HCR amplification occurs, followed by washing away unpolymerized hairpin monomers.

In some embodiments a method is provided wherein the method is applied in vitro and wherein the target is immobilized on a bead or microarray.

In some embodiments a method is provided wherein the method is in vitro or in vivo and wherein the target is not immobilized.

In some embodiments a method is provided wherein the method comprises a single stage protocol with no washes.

In some embodiments a method is provided wherein the target is at least one of DNA, RNA, protein, or small molecule target molecules or complexes in vitro, in situ, or in vivo.

In some embodiments a method is provided wherein the first fractional initiator (1151) is part of a first fractional initiator probe (1190) that further comprises a first target binding section (1141).

In some embodiments a method is provided wherein the second fractional initiator (1251) is part of a second fractional initiator probe (1290) that further comprises a second target-binding section (1241).

In some embodiments a method is provided, wherein the first target binding section is configured to bind adjacent to the second target binding section when the first fractional initiator probe and the second fractional initiator probe are both bound specifically to the target.

In some embodiments a method is provided comprising:
(a) providing:
  I. a first fractional initiator probe comprising a first fractional initiator
  II. a second fractional initiator probe comprising a second fractional initiator
  III. a first hairpin monomer, comprising:
    a. a first input domain, comprising a first toehold and a first stem section,
    b. a first output domain, comprising a first hairpin loop and a complement to the first stem section, and
    c. a first reporter molecule;
  IV. a second hairpin monomer, comprising:
    a. a second input domain, comprising a second toehold and a second stem section,
    b. a second output domain, comprising a second hairpin loop and a complement to the second stem section, and
    c. a second reporter molecule:
  V. a target molecule; and
(b) incubating the provided first fractional initiator probe and the second fractional initiator probe with a target.

In some embodiments a method is provided, wherein incubating binds the first fractional initiator probe to the target molecule and binds the second fractional initiator probe to the target molecule.

In some embodiments a method is provided wherein a wash is performed to remove unbound first and second fractional initiator probes from a sample that contains the target.

In some embodiments a method is provided, wherein individual fractional initiator probes that remain within the sample after the wash and are not specifically bound to the target do not trigger HCR.

In some embodiments a method is provided, wherein the sample is washed to remove at least 50 to 99% of probes that are not bound specifically to the target.

In some embodiments a method is provided comprising: a) binding the first hairpin monomer to both of the first fractional initiator and the second fractional initiator; b) binding the second hairpin monomer to the first hairpin monomer; and c) detecting a signal.

In some embodiments a method is provided comprising binding an additional first hairpin monomer to the second hairpin monomer.

In some embodiments a method is provided comprising binding an additional second hairpin monomer to the additional first hairpin monomer.

In some embodiments a method is provided, wherein there are at least 10 additional first hairpin monomers.

In some embodiments a method is provided, where there are at least 10 additional second hairpin monomers.

In some embodiments a method is provided, wherein there are at least 100 additional first hairpin monomers.

In some embodiments a method is provided, where there are at least 100 additional second hairpin monomers.

In some embodiments a method is provided, wherein the target molecule further comprises a first target section and a second target section, wherein the first fractional initiator probe further comprises a first target binding section and the second fractional initiator probe further comprises a second target binding section, wherein the first target section is configured to bind to the first target binding section and the second target section is configured to bind to the second target binding section.

In some embodiments a method is provided, wherein the reporter molecule is a fluorescent molecule.

In some embodiments a method is provided wherein the reporter molecule comprises a quenched or FRET arrangement, wherein a fluorescent molecule on a hairpin monomer is dequenched when a polymer configuration is achieved by the first and second hairpin monomers.

In some embodiments a method is provided wherein the first and second hairpin monomers form a FRET pair when combined as a polymer.

In some embodiments a method is provided wherein the FRET pair is formed due to a change in quenching or FRET that occurs when the hairpin monomers open and polymerize.

In some embodiments a method is provided wherein the reporter molecule is a non-fluorescent reporter molecule.

In some embodiments a method is provided wherein the reporter molecule is a rare earth element.

In some embodiments a method is provided further comprising at least one additional fractional initiator probe.

In some embodiments a method is provided wherein the target molecule is any nucleic acid molecule.

In some embodiments a method is provided wherein the target molecule is a protein.

In some embodiments a method is provided wherein the target molecule is selected from the group consisting of at least one of: mRNA, miRNA, lncRNA, rRNA, non-coding RNA, and genomic DNA.

In some embodiments a method is provided wherein the target molecule is comprised of an amino acid sequence.

In some embodiments a method is provided wherein the target molecule is comprised of a complex of molecules.

In some embodiments a method is provided wherein the first fractional initiator probe comprises a synthetic polymer and the second fractional initiator probe comprises a synthetic polymer.

In some embodiments a method is provided wherein the first fractional initiator probe comprises an amino acid sequence and the second fractional initiator probe comprises an amino acid sequence.

In some embodiments a method is provided wherein the first and second fractional initiator can base-pair with the first hairpin monomer.

In some embodiments a method is provided wherein the first fractional initiator probe comprises at least one molecule selected from the group consisting of DNA, RNA, 2'Ome-RNA, LNA, synthetic nucleic acid analog, amino acid, synthetic amino acid analog, and PNA and the second fractional initiator probe comprises at least one molecule selected from the group consisting of DNA, RNA, 2'Ome-RNA, LNA, synthetic nucleic acid analog, amino acid, synthetic amino acid analog, and PNA.

In some embodiments a method or composition is provided wherein binding denotes hybridization.

In some embodiments a method or composition is provided wherein binding denotes a selective protein-protein interaction.

In some embodiments a method or composition is provided wherein binding denotes a selective nucleic acid-protein interaction.

In some embodiments a method is provided wherein the HCR monomers comprise a label-binding site.

In some embodiments the method further includes: washing the sample to remove unpolymerized HCR hairpin monomers; adding a label probe that comprises a complement to the label binding site and a reporter molecule; washing unbound label probe; and detecting a presence or absence of the reporter molecule.

In some embodiments a composition is provided wherein the first hairpin monomer further comprises a label-binding site that is configured to hybridize to a complement to the label binding site, wherein the complement to the label binding site further comprises a reporter molecule. In some embodiments, both hairpin monomers can comprise a label-binding site. In some embodiments, just one of the hairpin monomers comprises a label-binding site.

DETAILED DESCRIPTION

Figure 1:
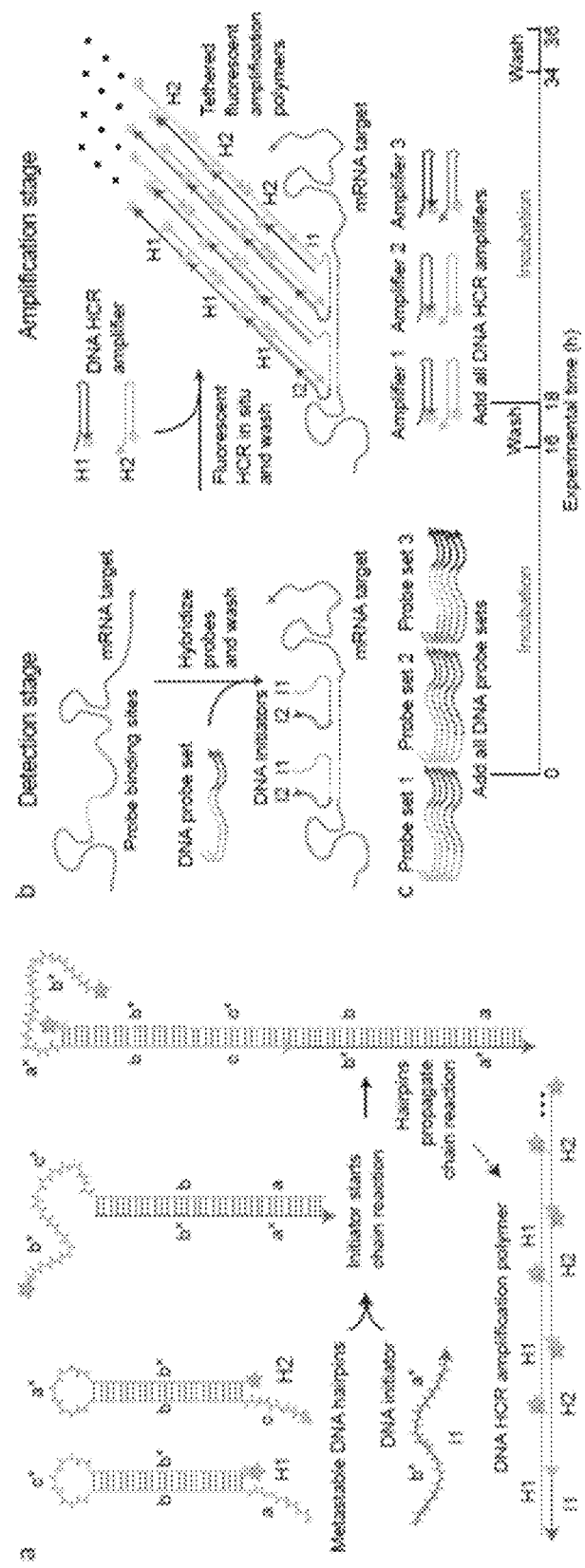
FIG. 1 depicts some embodiments of in situ amplification via hybridization chain reaction (HCR).

Hybridization Chain Reaction (HCR) is a method for the triggered hybridization of nucleic acid molecules starting from metastable hairpin monomers or other metastable nucleic acid structures. See, for example, Dirks, R. and Pierce, N. Proc. Natl. Acad. Sci. USA 101(43): 15275-15278 (2004), and U.S. patent application Ser. No. 11/087,937, filed Mar. 22, 2005, U.S. Pat. No. 8,105,778, Jan. 31, 2012, and U.S. Pat. No. 8,507,204, Aug. 13, 2013, each of which is incorporated herein by reference in its entirety. HCR does not require any enzymes and can operate isothermally.

HCR can involve two or more metastable hairpin monomers. The hairpin monomers each have at last one single-stranded toehold, a single-stranded loop, and a double-stranded stem. The energy to drive the self-assembly cascade is stored in the single-stranded loop and toehold segments of the hairpins.

Each monomer is caught in a kinetic trap, preventing the system from rapidly equilibrating. That is, pairs of monomers are unable to hybridize with each other in the absence of an initiator. Introduction of an initiator strand causes the monomers to undergo a chain reaction of hybridization events to form a nicked double-stranded polymer. HCR can be used, for example, to detect the presence of an analyte of interest in a sample by detecting the analyte with a probe that carries an HCR initiator, which in turn triggers HCR signal amplification. HCR signal amplification makes it possible to increase the signal-to-background ratio for molecular detection and imaging applications by boosting the signal above the background arising from the sample.

Some embodiments provided herein provide for even greater signal-to-background ratio using fractional initiator probes that divide the HCR initiator between two or more probes. If these individual probes bind non-specifically in the sample they do not trigger HCR. However, if they bind specifically to their cognate target, the fractional initiators are colocalized to form a full initiator, enabling the triggering of HCR signal amplification. In some embodiments, separating the initiator into parts (two or more), which only effectively co-localize in the presence of a target, provides for automatic background suppression during the detection step. When combined with the automatic background suppression provided by HCR during amplification, the new process provides for automatic background suppression throughout the protocol (for example, if a reagent, either an individual probe or an individual hairpin monomer binds in the sample, it will not lead to generation of amplified background).

Prior techniques did not introduce fractional-initiators (or probes thereof) as a mechanism for achieving automatic background suppression during the detection step. As a result, with prior techniques, if a probe carrying a full HCR initiator bound non-specifically in the sample, it might nonetheless trigger HCR, generating amplified background that would decrease the signal-to-background ratio of the measurement.

Definitions and Embodiments

"Nucleic Acids" as used herein includes oligomers of some form of DNA and/or RNA. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules. The phrase includes artificial constructs as well as derivatives etc. The phrase includes, for example, any one or more of DNA, RNA, 2'Ome-RNA, LNA, synthetic nucleic acid analog, and PNA.

The term "sticky end" refers to a nucleic acid sequence that is available to hybridize with a complementary nucleic acid sequence. The secondary structure of the "sticky end" is such that the sticky end is available to hybridize with a complementary nucleic acid under the appropriate reaction conditions without undergoing a conformational change. Typically the sticky end is a single stranded nucleic acid.

"Monomers" are individual nucleic acid oligomers. Typically, at least two monomers are used in hybridization chain reactions, although three, four, five, six or more monomers may be used. Typically each monomer comprises at least one region that is complementary to at least one other monomer being used for the HCR reaction.

The composition can include a first hairpin monomer (1510), comprising: a) a first input domain (1852), comprising a first toehold (1851) and a first stem section, b) a first output domain (1854), comprising a first hairpin loop (1853) and a complement to the first stem section, and c) a first reporter molecule (1850). The composition can further include a second hairpin monomer (1610), comprising: a) a second input domain (1952), comprising a second toehold (1951) and a second stem section, b) a second output domain (1954), comprising a second hairpin loop (1953) and a complement to the second stem section, and c) a second reporter molecule (1950).

In some embodiments, the monomers are "metastable." That is, in the absence of an initiator they are kinetically disfavored from associating with other monomers comprising complementary regions. "HCR" monomers are monomers that are able to assemble upon exposure to an initiator nucleic acid to form a polymer.

As used herein, "polymerization" refers to the association of two or more monomers to form a polymer. The "polymer" can comprise covalent bonds, non-covalent bonds or both. For example, in some embodiments two species of monomers are able to hybridize in an alternating pattern to form a polymer comprising a nicked double-stranded polymer. The polymers are also referred to herein as "HCR products."

A "full initiator" comes from the combination of two or more fractional initiators that, when colocalized, are able to initiate HCR polymerization. Some initiators comprise a nucleic acid region that is complementary to the initiator complement region of an HCR monomer. A fractional initiator is one that, on its own is insufficient to trigger HCR polymerization, but when colocalized with one (or more) other fractional initiators to form a full initiator, can trigger HCR polymerization.

The following terms, in Table 1, are indicated as alternative options (which may vary in breadth depending upon the context) for the terms used herein. The disclosure of the broadest term not only denotes the broadest concept, but also the narrower concept.

TABLE 1

| | |
|---|---|
| Split-initiator probe | Fractional initiator probe |
| Target-binding sequence | Target-binding section |
| Proximal subsequence | Target section |
| Cognate proximal target site | Target section |
| Target-binding region | Target-binding section |
| HCR Initiator I1 | Full HCR Initiator |
| Hairpin H1 | First Hairpin Monomer |
| Hairpin H2 | Second Hairpin Monomer |
| HCR Hairpin | Hairpin Monomer |
| Split-initiator probe pair | Fractional initiator probe pair |
| Cognate target site | Target section |
| Initiator I1 | Full HCR Initiator |
| Probe 1 | First fractional initiator probe |
| Probe 2 | Second fractional initiator probe |

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). It is to be understood that both the general description and the detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

Compositions

Figure 13:
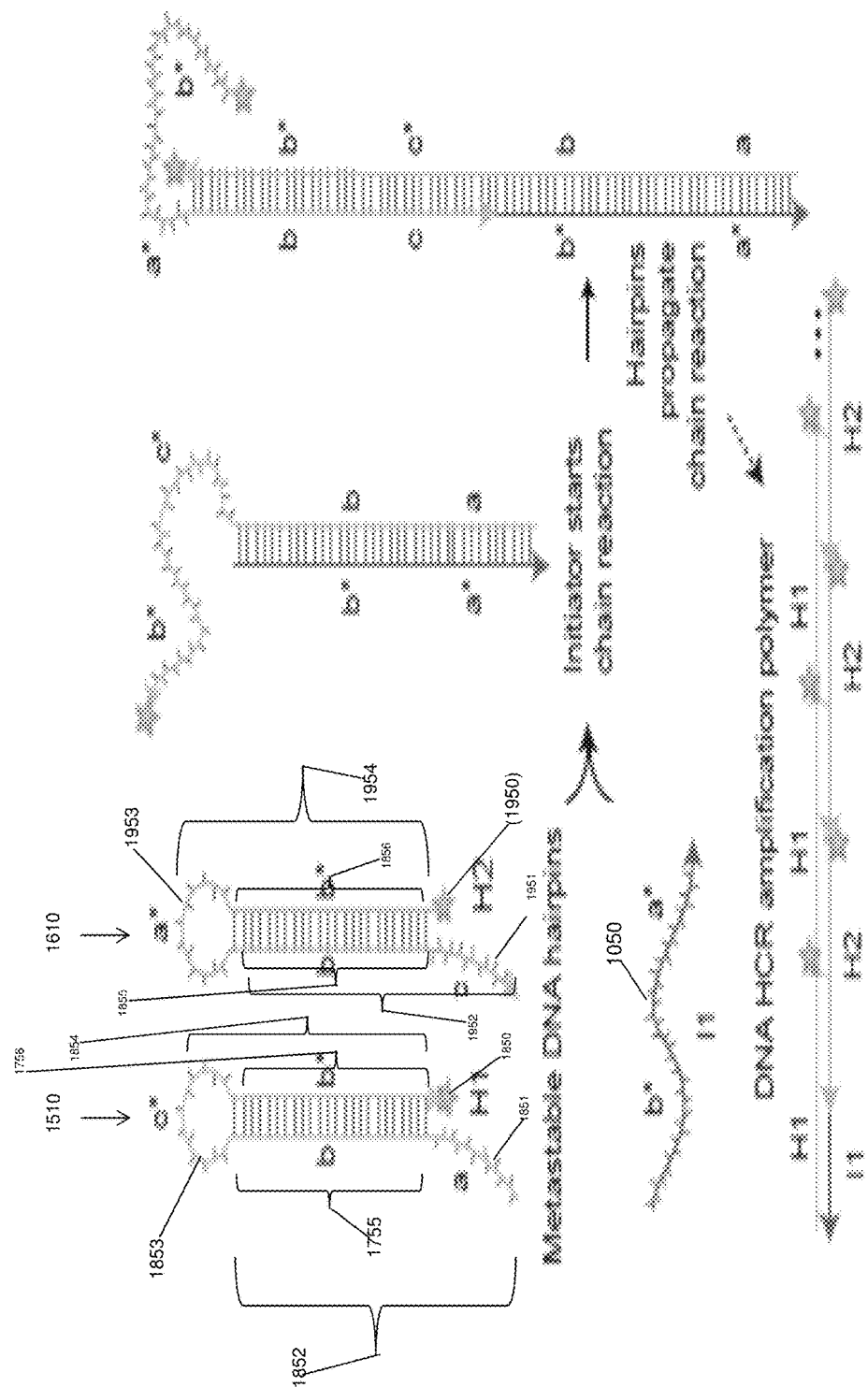
FIG. 13 depicts some embodiments of triggered self-assembly of an HCR amplification polymer from hairpin monomers upon initiation by an HCR initiator. 1050 in FIG. 13 depicts a full initiator, from two parts. Only a part of the fractional initiator probes is depicted. I1 (1050) denotes a full initiator formed by two fractional initiator probes colocalized by a target.
Figure 14:
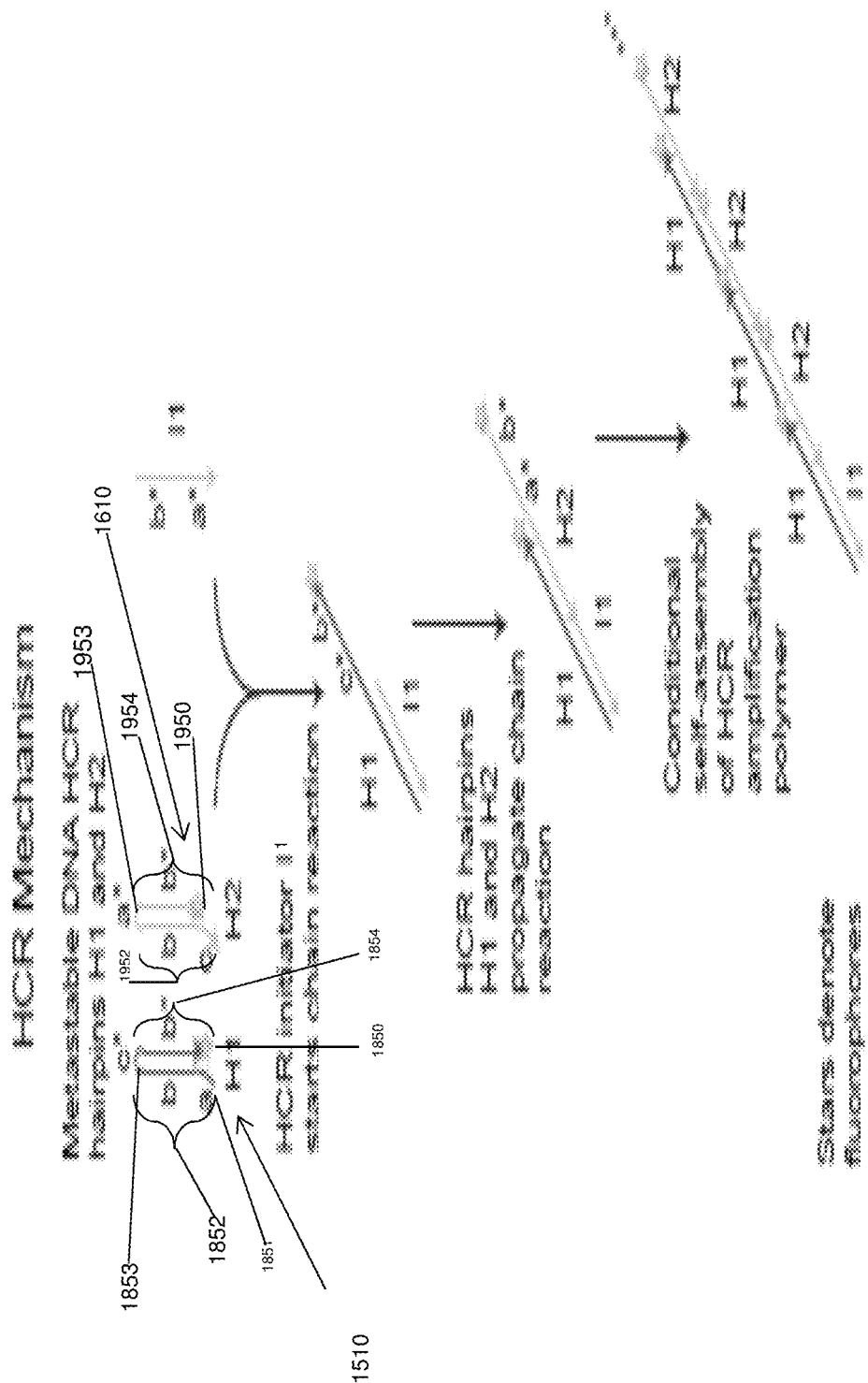
FIG. 14 depicts some embodiments of HCR amplification using hairpin monomers triggered by an HCR initiator. Only a part of the fractional initiator probes is depicted. I1 denotes a full initiator formed by two fractional initiator probes colocalized by a target.
Figure 12:
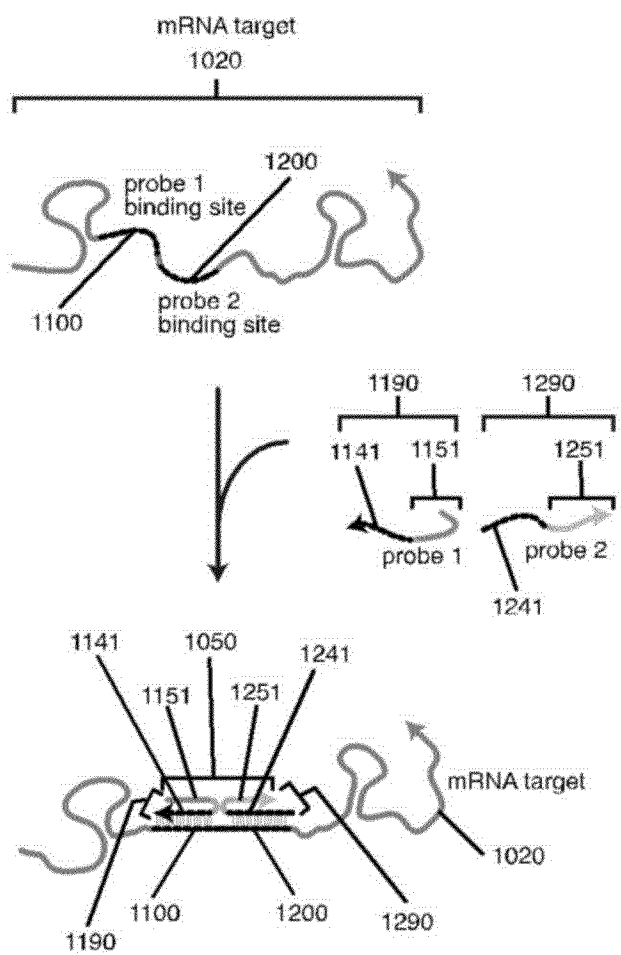
FIG. 12 depicts some embodiments of hybridizing a first fractional initiator probe and a second fractional initiator probe to a target molecule.
Figure 13:
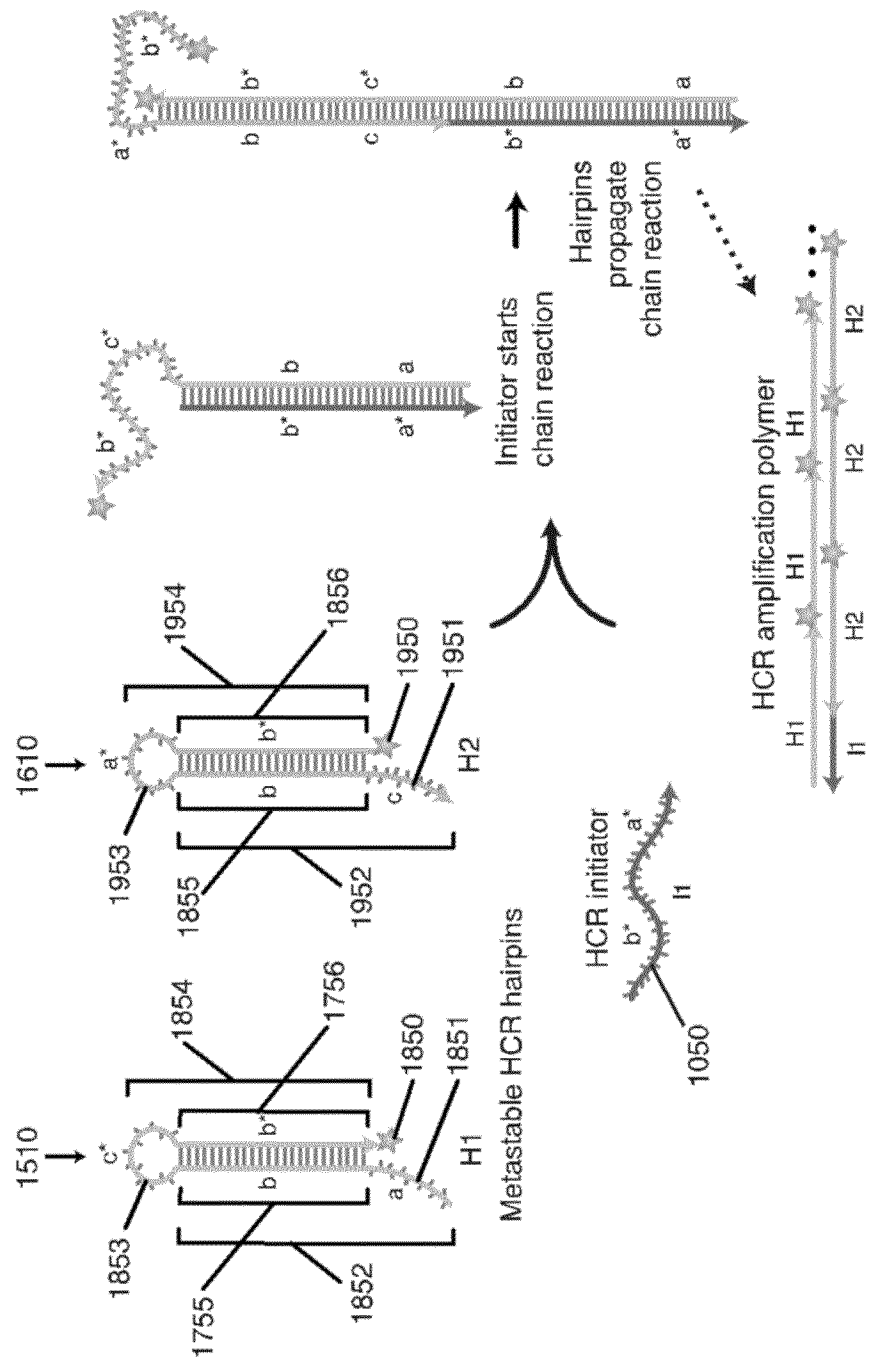
Figure 14:
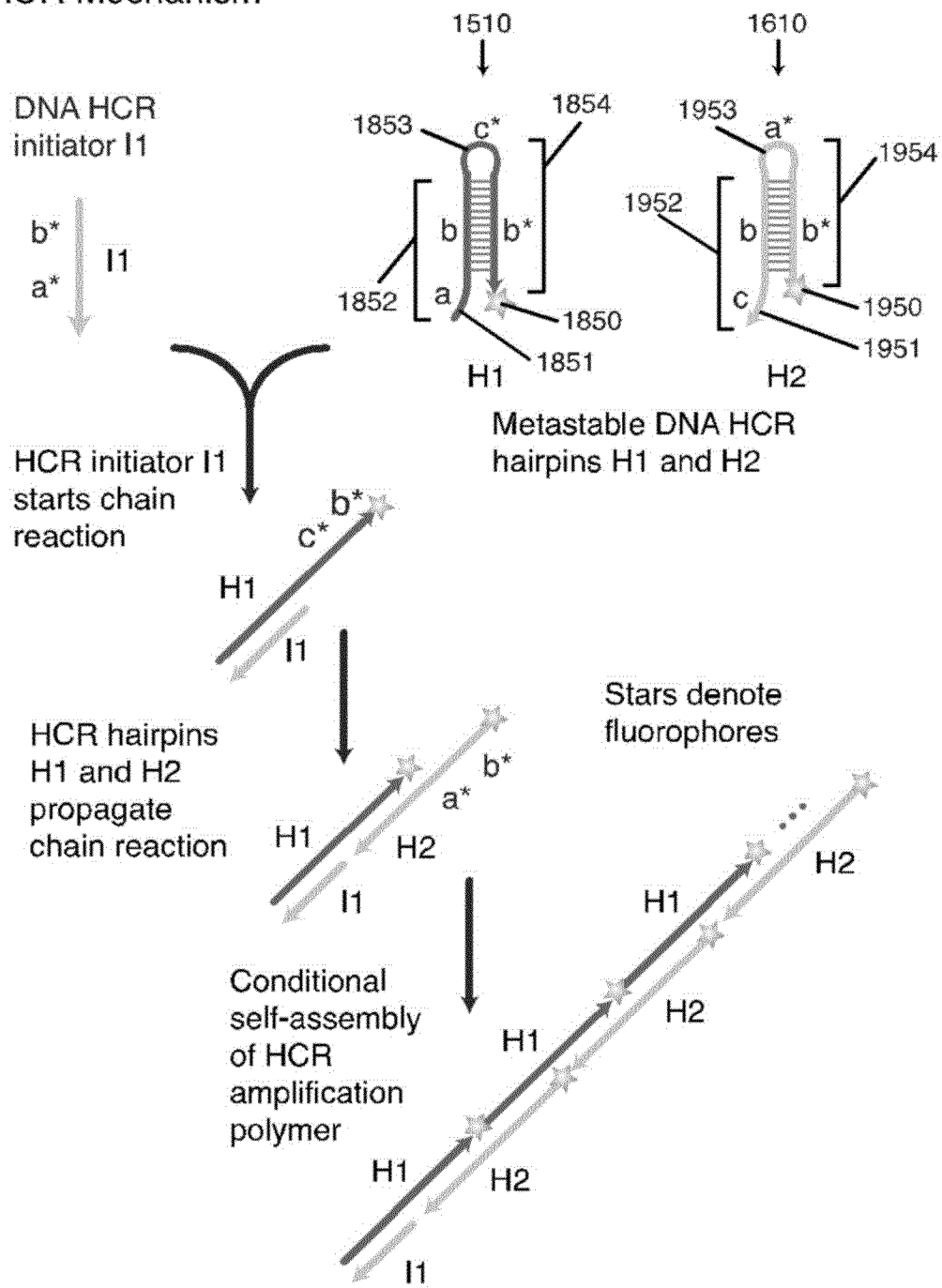
Figure 15:
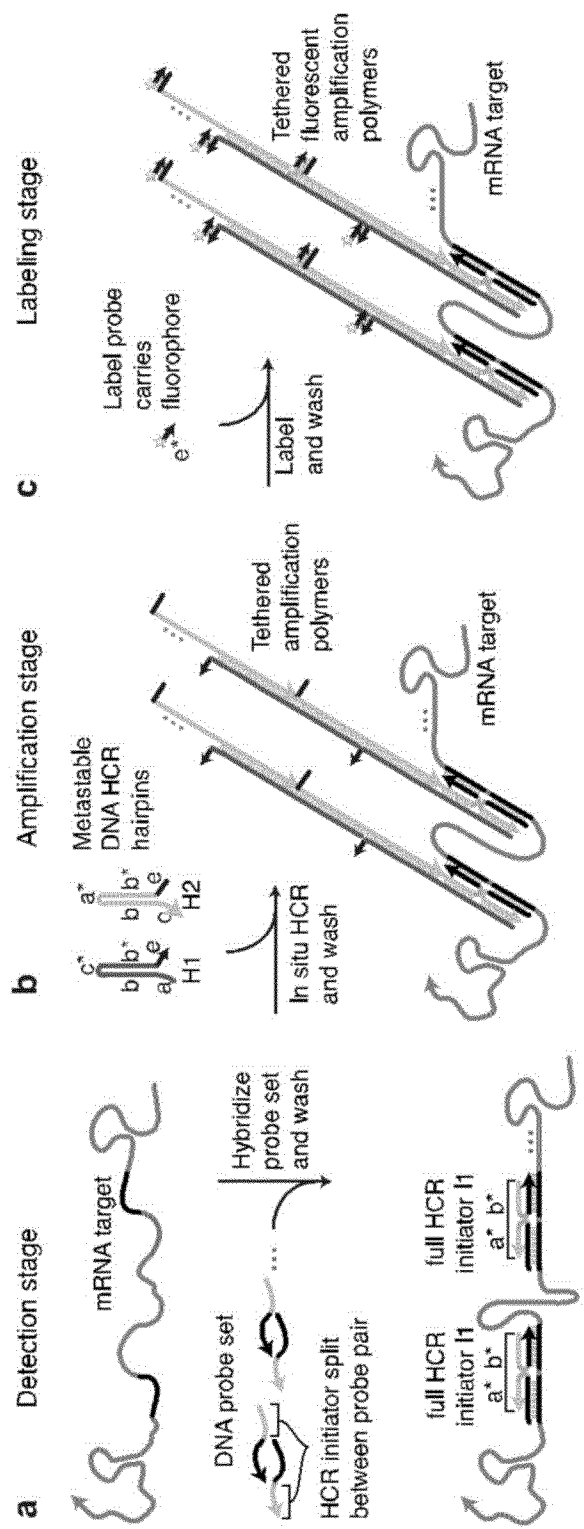
Figure 16:
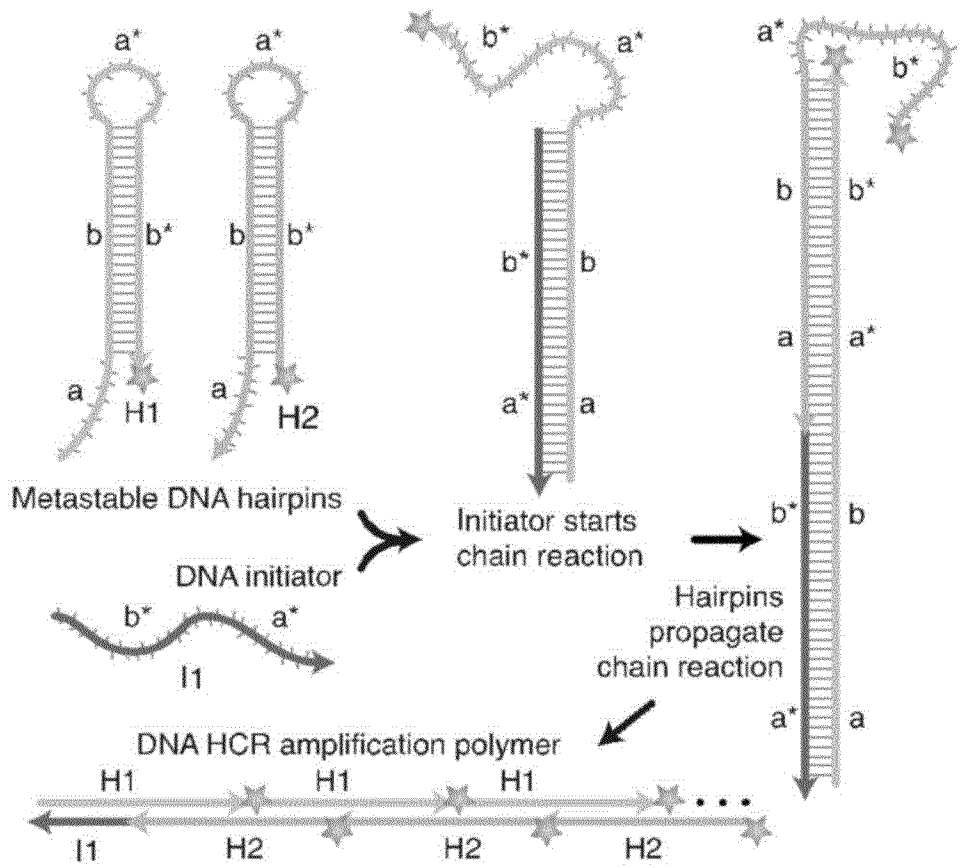

Some embodiments of compositions are outlined in FIGS. 12 and 13, as well as other figures provided herein. In some embodiments, a composition is provided that comprises a first fractional initiator probe (1190) that comprises a first fractional initiator (1151), and a second fractional initiator probe (1290) that comprises a second fractional initiator (1251). In some embodiments, the first and second fractional initiators (1151, 1251) together form a full initiator (1050), from which HCR can progress, via first and second hairpin monomers ((1510, 1610). In some embodiments, the first fractional initiator probe (1190) further comprises a first target binding section (1141) and the second fractional initiator probe (1290) further comprises a second target binding section (1241), wherein the first target binding section (1141) is configured to bind to a first target section (1100) and the second target binding section (1241) is configured to bind to a second target section (1200). These target binding sections are located effectively adjacent on the target molecule, such that when both fractional initiator probes are bound to both targets, the first and second fractional initiators (within the fractional initiator probes) are close enough to form a full initiator (1050), from which HCR can occur. In some embodiments, these fractional initiator probes can be provided as a kit, along with hairpin monomers for HCR polymerization.

In some embodiments, a composition is provided comprising a first hairpin monomer (1510), a second hairpin monomer (1610), a first fractional initiator probe (1190) comprising a first fractional initiator (1151), and a second fractional initiator probe (1290) comprising a second fractional initiator (1251). In some embodiments, the first and second fractional initiators (1151, 1251) together form a full initiator (1050), from which HCR can progress, via the first and second hairpin monomers (1510, 1610).

In some embodiments, the fractional initiator probes and the hairpin monomers can be introduced to the same sample at the same time. In some embodiments, the fractional initiator probes can be introduced to the sample, followed by a wash, and then the hairpin monomers can be introduced to the sample, followed by a wash. In some embodiments, the fractional initiator probes and hairpin monomers can be introduced to the sample at different times.

In some embodiments, one or more of the hairpin monomers can include a reporter molecule, such that polymerization of the hairpin monomers (first and second, and optionally more), will result in a signaling event that is detectable. In some embodiments, the reporter molecule can be covalently associated with the hairpin monomer(s). In some embodiments, the reporter molecule can be subsequently bound to the HCR polymer after polymerization (e.g., in a subsequent hybridization event). In some embodiments, the first hairpin monomer (1510) comprises a label-binding site (not depicted) that is configured to hybridize to a complement to the label-binding site (not depicted). In some embodiments, the complement to the label-binding site further comprises a reporter molecule.

In some embodiments, a composition is provided that includes a first hairpin monomer (1510), comprising: a) a first input domain (1852), comprising a first toehold (1851) and a first stem section (1755), b) a first output domain (1854), comprising a first hairpin loop (1853) and a complement to the first stem section (1756), and c) a first reporter molecule (1850). The composition can further include a second hairpin monomer (1610), comprising: a) a second input domain (1952), comprising a second toehold (1951) and a second stem section (1855), b) a second output domain (1954), comprising a second hairpin loop (1953) and a complement to the second stem section (1856), and c) a second reporter molecule (1950). The composition can further include a) a first fractional initiator probe (1190) comprising a first fractional initiator (1151), and b) a second fractional initiator probe (1290) comprising a second fractional initiator (1251). As noted above, the first and second hairpin monomers can be introduced to the sample together with or separately from the first and second fractional initiator probes. In some embodiments, the monomers can be provided together, but separate from the first and second fractional initiator probes. In some embodiments, the hairpin monomers and the fractional initiator probes can be introduced to the same sample at the same time. In some embodiments, the hairpin monomers and the fractional initiator probes can be introduced to the same sample, but at different, non-overlapping times (with a wash to remove unbound molecules).

In some embodiments, the first stem section has the same sequence as the second stem section. In some embodiments, the complement to the first stem section has the same sequence as the complement to the second stem section. In some embodiments, the complement to the first stem section has the same sequence as the complement to the second stem section, and the first stem section has the same sequence as the second stem section. In some embodiments, the toehold sequence of the two hairpin monomers is the same and the loop sequence of the two hairpin monomers is the same (although the polarity of the two hairpin monomers is reversed, so the two hairpin monomers are not identical).

In some embodiments, the first toehold (1851) is complementary to the second hairpin loop. In some embodiments, the second toehold is complementary to the first hairpin loop. In some embodiments, this circularity allows for the hybridization chain reaction to occur. In some embodiments, the first toehold is not 100% complementary to the second hairpin loop, but is sufficient to allow for hybridization.

In some embodiments, more than two different input domains can be employed, for example, 3, 4, 5, 6, 7, 8, 9, 10, 100, 1000, 2000, 4000 or more input domains can be employed. In some embodiments, a corresponding number of subparts can be used for each input domain.

In some embodiments, any of the compositions described herein comprise a target molecule (1020) that comprises a first target section (1100) and a second target section (1200) (as shown, for example, in FIG. 12). In some embodiments, the target molecule comprises additional target sections, for example, three target sections, four target sections, five target sections, six target sections, seven target sections or more (e.g., 10, 50, 100, etc.). In some embodiments, the number of target sections will mean there are a corresponding number of target-binding sections (e.g., 1141, 1241). In some embodiments, this allows for greater specificity/selectivity for the initial formation of the full initiator (as it requires more target binding sections to bind to the target sections). In some embodiments, this allows for the parallel assaying of more than one target sequence at a time (thus allowing one to assay for multiple targets at once, each one involving two or more target binding sections/fractional initiator probes).

In some embodiments, any of the first fractional initiator probes (1190) described herein further comprises a first target binding section (1141) and any of the second fractional initiator probes (1290) described herein further comprises a second target binding section (1241). In some embodiments, the first target binding section (1141) is configured to bind to the first target section (1100). In some embodiments, the second target binding section (1241) is configured to bind to the second target section (1200). In some embodiments, the first and second fractional initiator probes comprise additional target binding sections, for example, two target binding sections, three target binding sections, four target binding sections, five target binding sections, 10, 20, 30, 40, 50, 100, 1000, 10,000, or more.

In some embodiments, the first target binding section is configured to bind to the first target section through selective protein-protein interactions (such as via an antibody as the first target-binding section). In some embodiments, the first target binding section is configured to bind to the first target section through selective nucleic acid-protein interactions (such as an aptamer as the first target-binding section). In some embodiments, the second target binding section is configured to bind to the second target section through selective protein-protein interactions (such as via an antibody as the second target-binding section). In some embodiments, the second target binding section is configured to bind to the second target section through selective nucleic acid-protein interactions (such as an aptamer as the second target-binding section). In some embodiments, the first target binding section is configured to bind to the first target section through hybridization. In some embodiments, the second target binding section is configured to bind to the second target section through hybridization. In some embodiments, the first target binding section is configured to bind to the first target section through covalent bonding or ionic bonding. In some embodiments, the second target binding section is configured to bind to the second target section through covalent or ionic bonding.

In some embodiments, any reporter molecule whose presence or absence can be monitored can be employed. In some embodiments, the reporter molecule comprises a fluorescent molecule such as a fluorophore, or a colorimetric compound, that allows the resulting polymers to be visualized. In some embodiments, the reporter molecule is directly observable. In some embodiments, the reporter molecule is indirectly observable. In some embodiments, the reporter molecule comprises an enzyme or is enzymatic, and/or can mediate enzymatic signaling after HCR polymerization. In some embodiments, reporting is achieved by catalyzed reporter deposition ("CARD"). In some embodiments, a label binding site on each hairpin monomer can provide binding of a complement to the label binding site, wherein the complement to the label binding site carries a reporter molecule. In some embodiments, one type of reporter molecule carried by the hairpin monomers or the complement to the label binding site can mediate enzymatic signal amplification (CARD) after HCR polymerization) such that a second type of reporter molecules deposited in the vicinity of HCR polymers/target molecules will then be detected. In some embodiments, the reporter molecule is at least one of a luminescent molecule, FRET molecules, fluorophore/quencher molecular pairs, or other detectable markers. In some embodiments, the reporter molecule can allow for a secondary molecule (such as a secondary antibody) to be employed for detection of the polymerization event. In some embodiments, the hairpin monomers can be labeled with reporter molecules (e.g., a fluorophore and a quencher) such that hairpin monomers are quenched but that the conformation change that occurs during HCR polymerization leads to fluorescent HCR amplification polymers.

Methods

In some embodiments a method is provided. The method comprises (i) providing a first fractional initiator probe, (1190) a second fractional initiator probe (1290), a first hairpin monomer (1510), a second hairpin monomer (1610), and a target molecule (1020) (ii) incubating to allow for binding, and (iii) detecting a signal.

In some embodiments, a method of performing HCR is provided. The method comprises (i) adding a first fractional initiator (1151) and a second fractional initiator (1251) to a sample, wherein together the first fractional initiator (1151) and the second fractional initiator (1251) provide a full HCR initiator and (ii) adding a set of HCR hairpin monomers to the sample so as to allow HCR to occur in the presence of the full HCR initiator. The set of HCR hairpin monomers are configured so as to polymerize via HCR.

In some embodiments, a method is provided. The method comprises (a) providing: I. a first fractional initiator probe (1190) comprising a first fractional initiator (1151), II. a second fractional initiator probe (1290) comprising a second fractional initiator (1251). The method can further comprise providing III. a first hairpin monomer (1510), comprising: a. a first input domain (1852), comprising a first toehold (1851) and a first stem section (1755), b. a first output domain (1854), comprising a first hairpin loop (1853) and a complement to the first stem section (1756), and c. a first reporter molecule (1850). Further provided is IV. a second hairpin monomer (1610), comprising: a. a second input domain (1952), comprising a second toehold (1951) and a second stem section (1855), b. a second output domain (1954), comprising a second hairpin loop (1953) and a complement to the second stem section (1856), and c. a second reporter molecule (1950). Further provided is V. a target molecule (1020). The method further comprises (b) incubating the provided first fractional initiator probe and the second fractional initiator probe with a target. As noted herein, the fractional initiator probes can further include target binding sections, so as to colocalize two fractional initiators to thereby form the full initiator.

In some embodiments, the fractional initiator probes can be added initially to the sample that may include a target and then the bulk solution washed away, keeping the bound fractional initiator probes, and then the hairpin monomers can be added so that fractional initiator probes that are specifically bound to the target will colocalize fractional initiators and trigger HCR, but individual fractional initiator probes that are bound non-specifically will not colocalize a full initiator and will not trigger HCR.

In any of the methods described herein, any one or more of the following can be detected and/or assayed for: molecules, DNA molecules, RNA molecules, protein molecules, small molecules, synthetic molecules, or complexes of molecules. In some embodiments, the target is more than one target, such as a complex of proteins, or a complex of a protein and a nucleic acid, etc. Thus, the association of proteins can be assayed by the present fractional initiator approach. In some embodiments, inorganic or non-organic materials can also be assayed for. In some embodiments, any target can be detected, as long as there is a corresponding target binding section that can bind to the target that can be made part of the fractional initiator probe. In some embodiments, the target is any nucleic acid molecule. In some embodiments, the target is a protein. In some embodiments, the target consists of at least one of: mRNA, miRNA, lncRNA, rRNA, non-coding RNA, or genomic DNA. In some embodiments, the target is comprised of an amino acid sequence. In some embodiments, the target is comprised of a complex of molecules. In some embodiments, the target is at least one of: DNA, RNA, protein, or small molecule target molecules or complexes in vitro, in situ, or in vivo. In some embodiments, the target is a complex of molecules that is made up of at least one of: DNA, RNA, protein, or small molecule target molecules. In some embodiments, the target comprises a molecule or complex in vitro, in situ, or in vivo.

Figure 5:
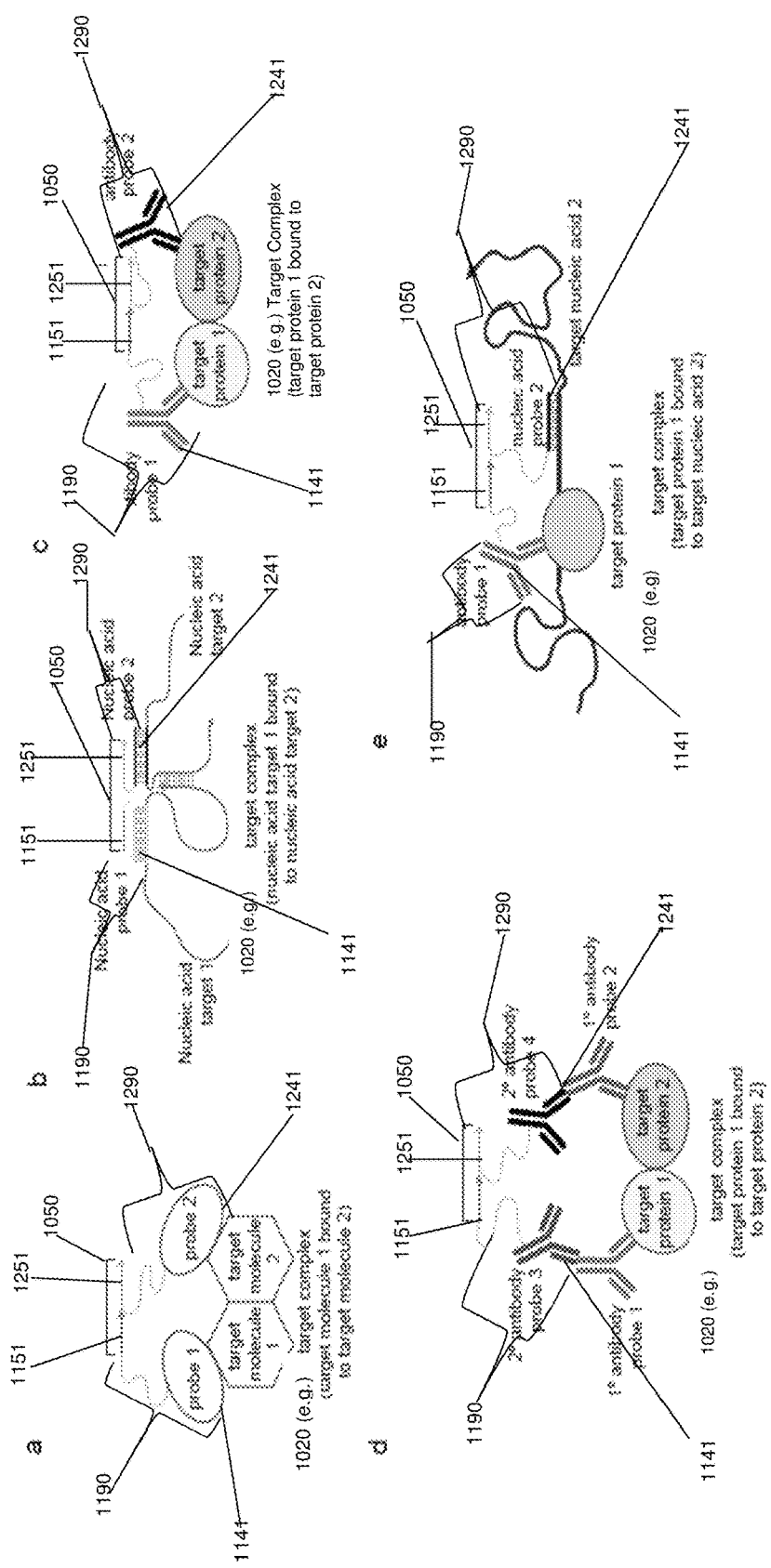
FIG. 5 depicts some embodiments of fractional initiator probes colocalized by a target complex.

In some embodiments, the target molecule can be a complex of molecules such that when the target binding sites within a fractional initiator (aka a split-initiator) probe pair bind specifically to their target sites within the complex, the two halves of the HCR initiator are brought into proximity, such that the full initiator becomes capable of initiating HCR signal amplification. FIG. 5 illustrates detection of a target complex using fractional initiator (aka a split-initiator) probes (panel a), detection of a target complex of nucleic acids using fractional initiator (aka a split-initiator) nucleic acid probes (panel b), detection of a target complex of proteins using fractional initiator (aka a split-initiator) antibody probes (panel c), detection of a target complex of proteins using primary-antibody probes and fractional initiator (aka a split-initiator) secondary-antibody probes (panel d), detection of a target protein/nucleic acid complex using split-initiator antibody and nucleic acid probes (panel e).

In some embodiments, any of the methods described herein can be used as part of an in situ process to image DNA, RNA, protein, or small molecule targets, including DNA in situ hybridization (ISH), RNA in situ hybridization (ISH), or protein immunohistochemistry (IHC).

In some embodiments, any of the methods described herein further comprise applying one or more of the components to a target. In some embodiments, the target is hydrated. In some embodiments, the target is in a solution, but can be immobilized to a solid support. In some embodiments, the target is in a solution. In some embodiments, the target is immobilized on a bead or other support. In some embodiments, the support is a mesh or a gel or a rigid surface. In some embodiments, the target is not immobilized. In some embodiments, the detection occurs in vivo, in vitro, or in situ. In some embodiments, an HCR method is provided that comprises an in vitro method in which the target is immobilized on a bead or microarray. In some embodiments, the target is immobilized on a bead. In some embodiments, the target is immobilized on a microarray. In some embodiments, an HCR method is provided that comprises an in vivo or in vitro method in which the target is not immobilized. In some embodiments, an HCR method is provided that comprises an in vivo or in vitro method in which the target is immobilized.

In some embodiments, incubating results in binding the first fractional initiator probe (1190) to the target molecule and in binding the second fractional initiator probe (1290) to a target molecule. The target molecule can be a single molecule or multiple associated molecules. In some embodiments, incubating occurs at room temperature. In some embodiments, incubating occurs at 4° C. In some embodiments, incubating occurs at 37° C. In some embodiments, incubating occurs at 45° C. In some embodiments, incubating occurs at 50° C. In some embodiments, incubating occurs at 55° C. In some embodiments, incubating occurs at 60° C. In some embodiments, incubating comprises an incubation period of at least 1 minute, for example, 5 minutes, 15 minutes, 30 minutes or 1 hour. In some embodiments, the incubation period exceeds 1 hour, for example, 2 hours, 4 hours, 12 hours, 16 hours, or 24 hours. In some embodiments, incubating occurs in hybridization buffer containing 0% formamide. In some embodiments, incubating occurs in hybridization buffer comprises formamide. In some embodiments, the percent concentration of formamide is between 1% and 80%, for example, between 10% and 70%, or between 30% and 60%. In some embodiments, the hybridization buffer comprises citric acid. In some embodiments, the molar concentration of citric acid is between 1 nM and 30 nM, for example, between 5 nM and 15 nM or between 8 nM and 12 nM. In some embodiments, the hybridization buffer comprises Tween. In some embodiments, the percent concentration of Tween is between 0% and 1.0%, for example, between 0.05% and 0.5%. In some embodiments, the hybridization buffer comprises heparin. In some embodiments, the concentration of heparin is between 20 μg/mL and 80 μg/mL, for example, between 30 μg/mL and 70 μg/mL, for example, between 40 μg/mL and 60 μg/mL. In some embodiments, the hybridization buffer comprises Denhardt's solution. In some embodiments, the hybridization buffer comprises dextran sulfate. In some embodiments, the percent concentration of dextran sulfate is between 1% and 60%, for example, between 40% and 60%.

In some embodiments the first fractional initiator (1151) of any of the methods described herein is part of a first fractional initiator probe (1190) and the second fractional initiator (1251) is part of a second fractional initiator probe (1290). In some embodiments, the first fractional initiator probe (1190) further comprises a first target-binding section (1141) and the second fractional initiator probe (1290) further comprises a second target-binding section (1241). In some embodiments, the first target-binding section (1141) is configured to bind adjacent to the second target-binding section (1241) on a target, when the first fractional initiator probe (1190) and the second fractional initiator probe (1290) are both bound specifically to a target (1020).

While the term "adjacent" is used for binding of the first and second fractional initiator probes (and/or first and second target-binding sections), binding need not be immediately adjacent, as long as the first and second initiator probes are close enough to one another to form a full initiator capable of triggering HCR. In some embodiments, the first target-binding section binds at least within 10 amino acids of the second target binding section, for example within 5 amino acids or within 1 amino acid. In some embodiments, the first target-binding section binds at least within 10 nucleotides of the second target binding section, for example within 5 nucleotides or within 1 nucleotide. In some embodiments, the first and second fractional initiator probes (and/or first and second target-binding sections), are within 2, 5, 10, 50, 100, 1000, Angstroms of each other. In some embodiments, the first and second fractional initiator probes can include spacers—so as to allow more space between the two target sections. Such spacers could include additional nucleic acid sequence, to provide more flexibility for the location of the first and second (or additional) target sections. In some embodiments, each target section on the target is proximal enough to one another to allow the two or more fractional initiators to colocalize a full initiator.

In some embodiments, the first fractional initiator probe (1190) comprises more than one target-binding section, for example, two target binding sections, three target binding sections, four target binding sections, or five target binding sections. This can allow for assaying of multiple possible targets at a time. In some embodiments, the first fractional initiator probe (1190) comprises more than five target binding sections. In some embodiments, the second fractional initiator probe (1290) comprises more than one target-binding section, for example, two target binding sections, three target binding sections, four target binding sections, or five target binding sections. In some embodiments, the second fractional initiator probe (1290) comprises more than five target binding sections.

Figure 4:
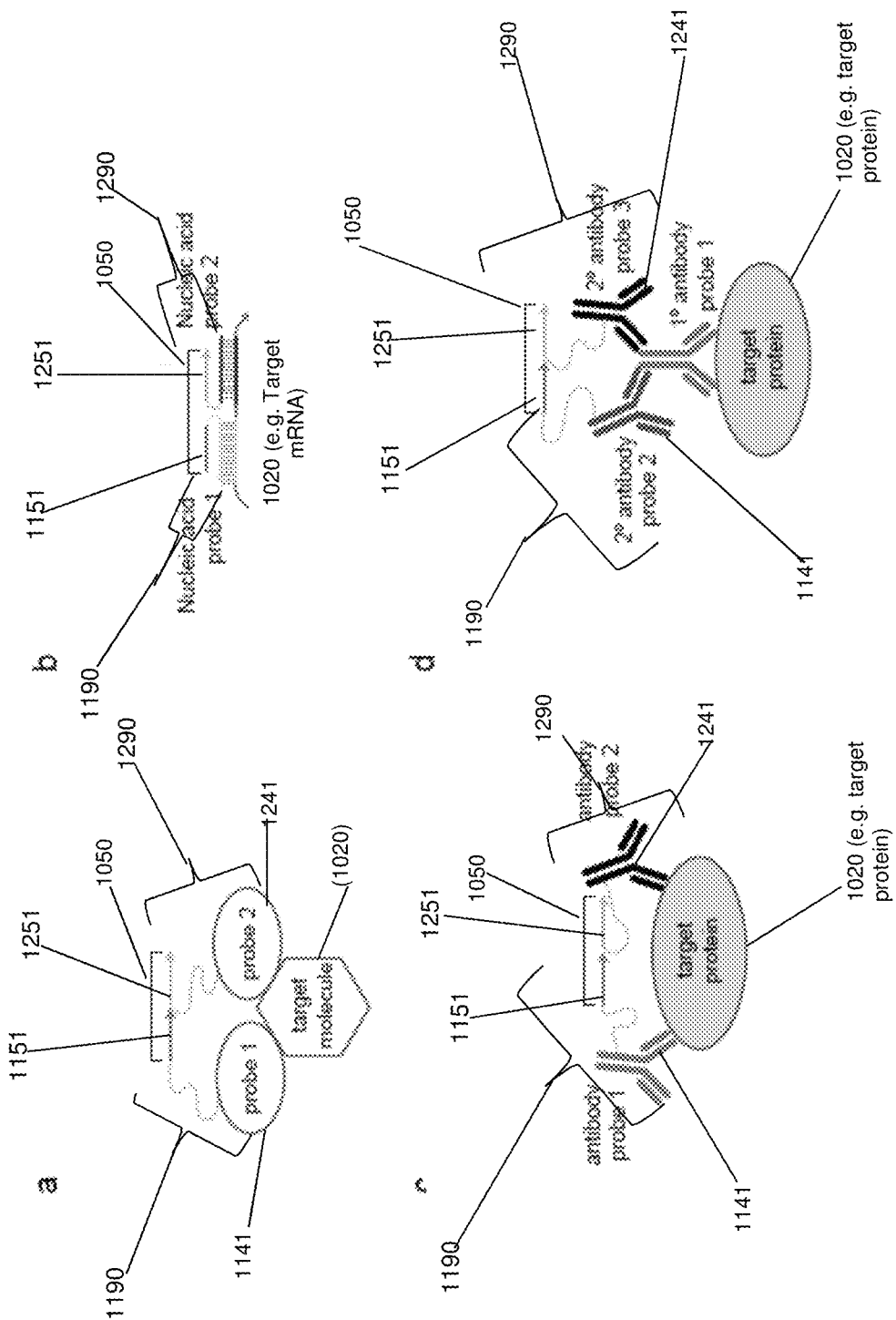
FIG. 4 depicts some embodiments of fractional initiator probes colocalized by a target molecule.

In some embodiments, the target binding section (e.g., region) within each of the fractional initiator (aka a split-initiator) probe pairs can be made of DNA, RNA, 2'OMe-RNA, PNA, amino acids, or any synthetic nucleic acid analog, or any synthetic amino acid analog. FIG. 4 illustrates detection of a target molecule using fractional initiator (aka a split-initiator) probes (panel a), detection of a target mRNA using fractional initiator (aka a split-initiator) nucleic acid probes (panel b), detection of a target protein using fractional initiator (aka a split-initiator) antibody probes (panel c), and detection of a target protein using a primary-antibody probe and split-initiator secondary-antibody probes (panel d). In each case, selective binding of the probe pair to the cognate target molecule colocalizes the two halves of the full HCR initiator, triggering growth of a tethered HCR amplification polymer. The target molecule can be a protein or small molecule such that when the target binding sites within the fractional initiator (aka a split-initiator) probe pair bind specifically to their target sites on the protein or small molecule, the two halves of the HCR initiator are brought into proximity, such that the full initiator becomes capable of initiating HCR signal amplification.

In some embodiments, HCR hairpin monomers may be labeled with reporter molecules that are not fluorescent (e.g., isotopically pure rare earth elements, chromophores, etc.).

Figure 3:
FIG. 3 depicts some arrangements for two adjacent target sections and two fractional initiator probes that hybridize to these adjacent target sections to colocalize two fractional initiators.

For Scheme E, each probe within a fractional initiator (aka a split-initiator) probe pair contains a target binding site and half of an HCR initiator such that when the fractional initiator (aka a split-initiator) probes base-pair specifically to their target sections (e.g., cognate proximal target sites), the two halves of the HCR initiator are co-localized; this functionality can be achieved by arranging the target binding sites and initiator fragments within the fractional initiator (aka a split-initiator) probe pair in a variety of configurations (FIG. 3).

In some embodiments, the HCR initiator within a fractional initiator (aka a split-initiator) probe pair can be split between two probes (not necessarily half-and-half) in such a way that HCR amplification is only initiated if both probes are proximal.

In some embodiments, the HCR initiator can be split between two or more fractional initiator (aka a split-initiator) probes.

In some embodiments, the target mRNA can be detected using a fractional initiator probe set (or probe set) containing one or more fractional initiator (aka a split-initiator) probe pairs; each probe pair contains target-binding sites addressing different subsequences of the target mRNA. Within a fractional initiator probe set, each fractional initiator (aka a split-initiator) probe pair co-localizes to form the same HCR initiator sequence, thus enabling simultaneous growth of HCR amplification polymers off of multiple probe pairs bound to the same target mRNA.

In some embodiments, the target molecule could be an mRNA, a miRNA, a lncRNA, an rRNA, genomic DNA, or any nucleic acid molecule.

In some embodiments, the initiator that is split between the two fractional initiator (aka a split-initiator) probes within a pair could be made of DNA, RNA, 2'OMe-RNA, PNA, or any synthetic polymer capable of initiating HCR amplification.

In some embodiments, any of the methods described herein comprise adding more than a first fractional initiator (1151) and a second fractional initiator (1251), for example, adding 10, 20, 50, 100, 1000, 10,000 etc.

In some embodiments, any of the methods described herein can comprise a 2-stage approach with a wash after each stage. In some embodiments, the target is immobilized and/or the sample is fixed. In some embodiments, the first stage is a detection stage that comprises binding fractional initiator probe(s) to a target and washing away unbound fractional initiator probe(s) and the second stage is an amplification stage in which HCR amplification occurs. This can be followed by washing away unpolymerized HCR monomers (such as hairpin monomers). In some embodiments, there is more than one wash after each stage, for example, two washes, three washes, four washes, or five washes. In some embodiments, the HCR method comprises a single stage with no washes.

In some embodiments, the HCR hairpin monomers comprise a label-binding site, rather than directly incorporating a reporter molecule onto the hairpin monomer itself. In some embodiments, any of the methods described herein further comprises washing the sample to remove unpolymerized HCR hairpin monomers, adding a label probe that comprises a complement to the label binding site and a reporter molecule; washing away unbound label probe, and detecting a presence or absence of the reporter molecule. In some embodiments, the label probe is a hairpin molecule that further comprises a flourophore/quencher pair, such that the fluorophore is quenched when the hairpin monomer is closed, but when the label probe binds the label binding site on an HCR polymer, the fluorophore is unquenched. In some embodiments, the label probe is a duplex with one strand carrying a fluorophore and the other strand carrying a quencher such that when the label probe binds the label binding site on an HCR polymer, the quencher-labeled strand is displaced and the fluorophore-labeled strand is bound to the label binding site on the HCR polymer. In some embodiments, the hairpin monomers carry a reporter that is one part of a FRET pair, and the label probe carries the other part of a FRET pair, such that upon binding of the label probe to the label binding site on an HCR polymer, the two parts of the FRET pair are brought into proximity and can undergo FRET. In some embodiments removing unpolymerized HCR hairpin monomer through washing results in the removal of greater than 50% of the unpolymerized HCR hairpin monomers, for example, greater than 55%, greater than 60%, greater than 65%, greater than 70%, greater than 75%, greater than 80%, greater than 85%, greater than 90%, greater than 95%, greater than 99%, greater than 99.9%, greater than 99.99%, greater than 99.999%, or greater than 99.9999999%.

In some embodiments, any of the washes provided herein can result in the removal of greater than 50% of the fractional initiator (and/or fractional initiator probe) for example, greater than 55%, greater than 60%, greater than 65%, greater than 70%, greater than 75%, greater than 80%, greater than 85%, greater than 90%, greater than 95%, greater than 99%, greater than 99.9%, greater than 99.99%, greater than 99.999%, or greater than 99.9999999%.

In some embodiments, a wash results in removal of at least 50 to 99% of probes that are not bound specifically to the target. In some embodiments, the wash results in the removal of greater than 50% of the probes, for example, greater than 55%, greater than 60%, greater than 65%, greater than 70%, greater than 75%, greater than 80%, greater than 85%, greater than 90%, or greater than 95%, greater than 99%, greater than 99.9%, greater than 99.99%, greater than 99.999%, or greater than 99.9999999%.

Any of the methods described herein can further comprise a first wash. In some embodiments, the first wash removes unbound first fractional initiator probe (1190) and unbound second fractional initiator probe (1290) from a sample containing a first target molecule. In some embodiments, following the first wash colocalized first and second initiator probes on the target molecules are bound by the first hairpin monomer (1510), which is then bound by the second hairpin monomer (1610), resulting in HCR amplification. In some embodiments, following the first wash, unbound hairpin monomers are washed from the sample. In some embodiments, the method comprises additional washes, for example 2 washes, 3 washes, 4 washes, 5 washes, 6 washes, or 7 washes. In some embodiments, the method comprises more than 7 washes.

In some embodiments, a fractional initiator can be from 1-1000 nucleotides in length, e.g., 10-80, 10-60, 10-50, 20-50, 20-30 nucleotides in length. In some embodiments, it can be of any functional length.

In some embodiments, each target section can be from 1-1000 nucleotides in length, e.g., 10-80, 10-60, 10-50, 20-50, 20-30 nucleotides in length. In some embodiments, it can be of any functional length.

In some embodiments, each target binding section can be from 1-1000 nucleotides in length, e.g., 10-80, 10-60, 10-50, 20-50, 20-30 nucleotides in length. In some embodiments, it can be of any functional length. In some embodiments, the target binding section and/or the target section are not nucleic acids, and thus can be proteins etc. as described herein. In some embodiments, the target binding sections can each be from individual atoms up to hundreds of kDa (e.g., antibodies etc.) or larger.

In some embodiments, each full initiator can be as long as the sum of the fractional initiators that form the full initiator. In some embodiments, each fractional initiator can be about ½ the size of the full initiator. In some embodiments, the fractional size of the fractional initiator depends upon the number of fractional initiators to complete the full initiator. Thus, when 2, 3, 4, 5, etc. fractional initiators are employed in a single full initiator, then ½, ⅓, ¼, ⅕, etc. of the initiator will be present in each fractional initiator. In some embodiments, the size of the initiator need not be evenly divided for each fractional initiator. The size of the full initiator is adequate to allow for HCR to occur through the full initiator.

In some embodiments, any of the methods and/or compositions described herein comprise adding at least one additional fractional initiator probe, for example, adding three fractional initiators, adding four fractional initiators, adding five fractional initiators, adding six fractional initiators, adding seven fractional initiators, adding eight fractional initiators, a nine fractional initiators, adding 10 fractional initiators, adding 11 fractional initiators, adding 12 fractional initiators, or adding 14 fractional initiators, adding 15 fractional initiators. In some embodiments, more than 15 fractional initiators are added, for example, between 16 and 100 fractional initiators or more, e.g., 500, 1000, etc.

In some embodiments, the target molecule (1020) comprises a first target section (1100) and a second target section (1200). The first fractional initiator probe (1190) can comprise a first target-binding section (1141) and the second fractional initiator probe (1290) comprises a second target-binding section (1241). The first target section (1100) is configured to bind to (or be bound by) the first target-binding section (1141) and the second target section (1200) is configured to bind to (or be bound by) the second target-binding section (1241).

In some embodiments, any of the methods described herein further comprises: binding the first hairpin monomer (1510) to both the first fractional initiator (1151) and the second fractional initiator (1251), binding the second hairpin monomer (1610) to the first hairpin monomer (1510), and detecting a signal. The signal can be generated or amplified via the first and second hairpin monomers going through a hybridization chain reaction to thereby add and/or concentrate an amount of a reporter molecule that is associated with one or both of the first and/or second hairpin monomers.

Wash steps can be performed prior to the addition of the hairpin monomers and/or detection. In some embodiments, the method comprises a wash to remove unbound first and second fractional initiator probes from a sample that contains a target. In some embodiments, the method comprises more than one wash, for example, 2 washes, 3 washes, 4 washes, or 5 washes. In some embodiments, individual fractional initiator probes that remain within the sample and/or solution after the wash and are not specifically bound to the target do not colocalize a full initiator and hence do not trigger HCR.

In some embodiments, any of the methods described herein comprise binding an additional first hairpin monomer (1510) to the second hairpin monomer (1610) (which is already bound to a first hairpin monomer). Thus, extending the chain of monomers can be achieved via HCR polymerization. In some embodiments, there are at least 10 additional first hairpin monomers. In some embodiments there are at least 100 additional first hairpin monomers, e.g., 1000, 10000, etc. In some embodiments, the method comprises binding an additional second hairpin monomer to the additional first hairpin monomer, which is already bound to a second hairpin monomer). In some embodiments, there are at least 10 additional second hairpin monomers. In some embodiments, there are at least 100 additional second hairpin monomers, e.g., 1000, 10000, etc. In some embodiments, any of the methods described herein comprise an alternating cascade of polymerization events in which a full initiator binds a first hairpin monomer (1510) which in turn binds a second hairpin monomer (1610) which in turn binds another first hairpin monomer which in turn binds another second hairpin monomer, and so on, such that the polymer grows via alternating addition of first and second hairpin monomers. In some embodiments the alternating cascade comprises binding of more than two hairpin monomers, for example, three hairpin monomers, four hairpin monomers, five hairpin monomers, six hairpin monomers, seven hairpin monomers, eight hairpin monomers, nine hairpin monomers, 10 hairpin monomers, 100, 1000, 10000, 100000, 1000000, or more.

In some embodiments, in any of the binding reactions described herein, binding comprises hybridization. In some embodiments, binding comprises selective protein-protein interaction. In some embodiments, binding comprises selective nucleic acid-protein interaction. In some embodiments, binding comprises ionic binding. In some embodiments, binding comprises covalent binding.

In some embodiments, in any of the methods or compositions described herein, the reporter molecule is a fluorescent molecule. In some embodiments, the reporter molecule comprises a quenched or FRET arrangement, in which a fluorescent molecule on a hairpin monomer is dequenched when a polymer configuration is achieved by the first and second hairpin monomers. In some embodiments, the reporter molecule is a non-fluorescent molecule. In some embodiments, the reporter molecule is a rare earth element.

In some embodiments, the first and second hairpin monomers form a FRET pair when combined as a polymer. In some embodiments, the FRET pair is formed due to a change in quenching or FRET that occurs when the hairpin monomers open and polymerize. Thus, in some embodiments, the hairpin monomers are configured to allow for FRET (e.g., meeting proximity requirements and reporter molecule pairing requirements for changes in FRET to be monitored).

In some embodiments, the first fractional initiator probe (1190) can comprise an amino acid sequence and the second fractional initiator probe (1290) can comprises an amino acid sequence. In some embodiments, the probe will also include a nucleic acid sequence to hybridize to the target sequence(s). These can be the first target binding sections and the second target binding sections. In some embodiments, the target binding sections are complementary to the first and second target sections (1100 and 1200). In some embodiments, the first and second fractional initiator probes will also include first and second fractional initiators, which can comprise nucleotides, providing a nucleic acid sequence of adequate length, which when colocalized, forms the full initiator. In some embodiments, the first fractional initiator probe (1190) comprises a nucleic acid sequence and the second fractional initiator probe (1290) comprises a nucleic acid sequence. In some embodiments, the first and second fractional initiators (1151, 1251) can base-pair with the first hairpin monomer (1510). In some embodiments, the first fractional initiator probe comprises one or more of the following: DNA, RNA, 2'Ome-RNA, LNA, synthetic nucleic acid analog, amino acid, synthetic amino acid analog, and PNA and the second fractional initiator probe comprises one or more of the following: DNA, RNA, 2'Ome-RNA, LNA, synthetic nucleic acid analog, amino acid, synthetic amino acid analog, and PNA.

In some embodiments, any of the wash buffers described herein comprises formamide. In some embodiments, the percent concentration of formamide is between 0% and 80%, for example, between 10% and 70%, or between 30% and 60%. In some embodiments, the wash buffer comprises citric acid. In some embodiments, the molar concentration of citric acid is between 1 nM and 30 nM, for example, between 5 nM and 15 nM or between 8 nM and 12 nM. In some embodiments, the wash buffer comprises Tween. In some embodiments, the percent concentration of Tween is between 0% and 1.0%, for example, between 0.05% and 0.5%. In some embodiments, the wash buffer comprises heparin. In some embodiments, the concentration of heparin is between 20 µg/mL and 80 µgmL, for example, between 30 µg/mL and 70 µg/mL, for example, between 40 µg/mL and 60 µg/mL.

A fractional initiator is distinct from other conditional probes. For example, in some embodiments, a fractional initiator is not a conformation-changing probe (e.g., scheme B in FIG. 2). In some embodiments, the fractional initiator is one that involves two separate strands of nucleic acids. In some embodiments, the fractional initiator is dependent upon at least two separate binding events to at least two different target sections (although the two sections can be on a single molecule).

In some embodiments, the method provided herein can be used to improve the signal-to-background ratio for In Situ Signal Amplification via Hybridization Chain Reaction (HCR).

Figure 15:
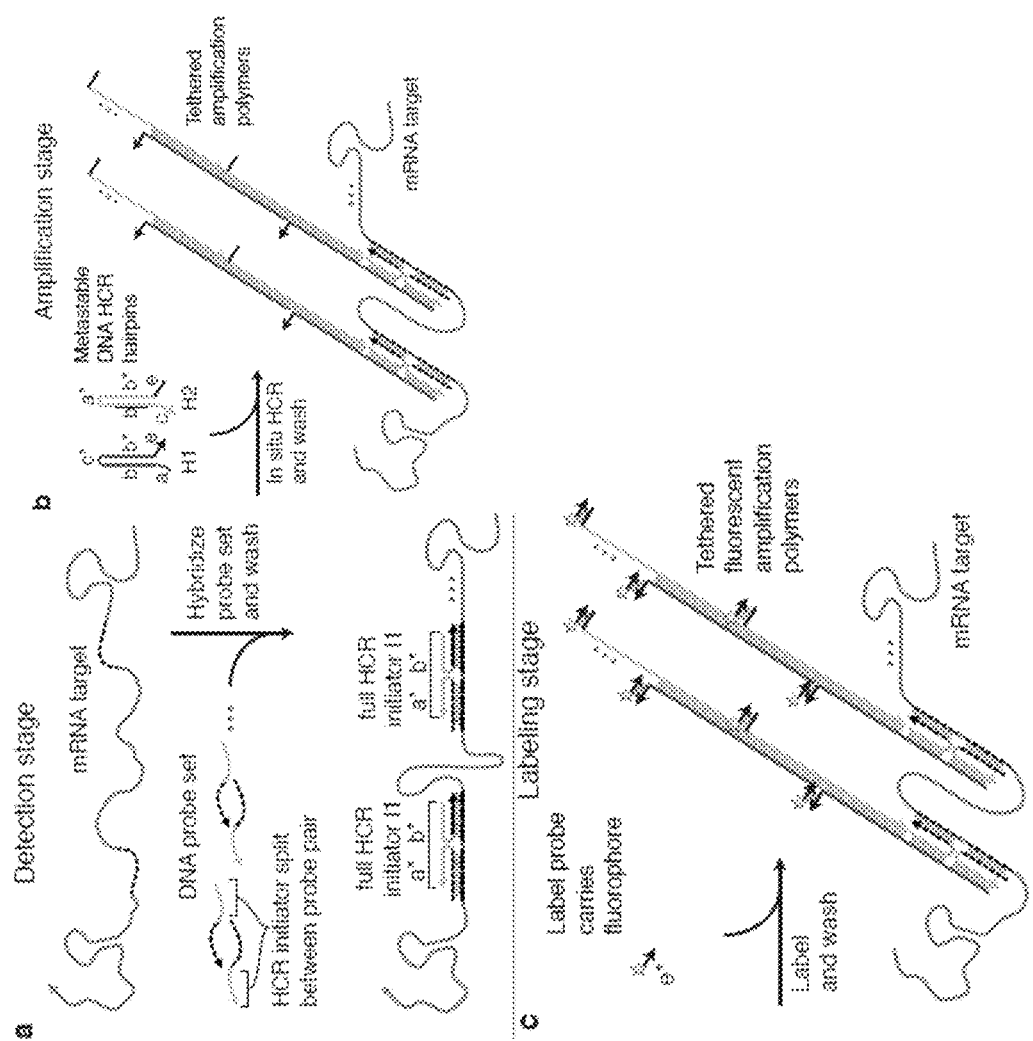
FIG. 15 depicts some embodiments of a three-stage in situ HCR protocol using fractional initiator probes with hairpin monomers that carry label binding sites.

FIG. 15 depicts further embodiments involving HCR, in particular, a three-stage in situ HCR protocol using fractional initiator probes with hairpin monomers that carry label binding sites. Panel (a) Detection stage: fractional-initiator probe pairs are hybridized to the target mRNA and unused probes are washed from the sample. Each fractional initiator probe set contains one or more probe pairs that selectively bind to different subsequences along the target mRNA. Each probe within a pair carries a part of the HCR initiator I1 (e.g., ½). Selective hybridization of the two probes within a pair to their cognate target binding sites colocalizes the two halves of full HCR initiator I1. Panel (b) Amplification stage: full HCR initiator I1 triggers self-assembly of tethered amplification polymers and unused H1 and H2 hairpin monomers are washed from the sample. Each hairpin monomer carries a label binding site. The label binding sites decorate the resulting HCR amplification polymer. Panel (c) Labeling stage: label probes comprising a complement to the label binding site and additionally comprising a fluorophore reporter are hybridized to the amplification polymers and then unbound label probes are washed from the sample. Stars denote fluorophores. Each of the stages may be repeated, combined, or separated depending upon the desired results. In some embodiments, the stages occur in the listed order.

Figure 16:
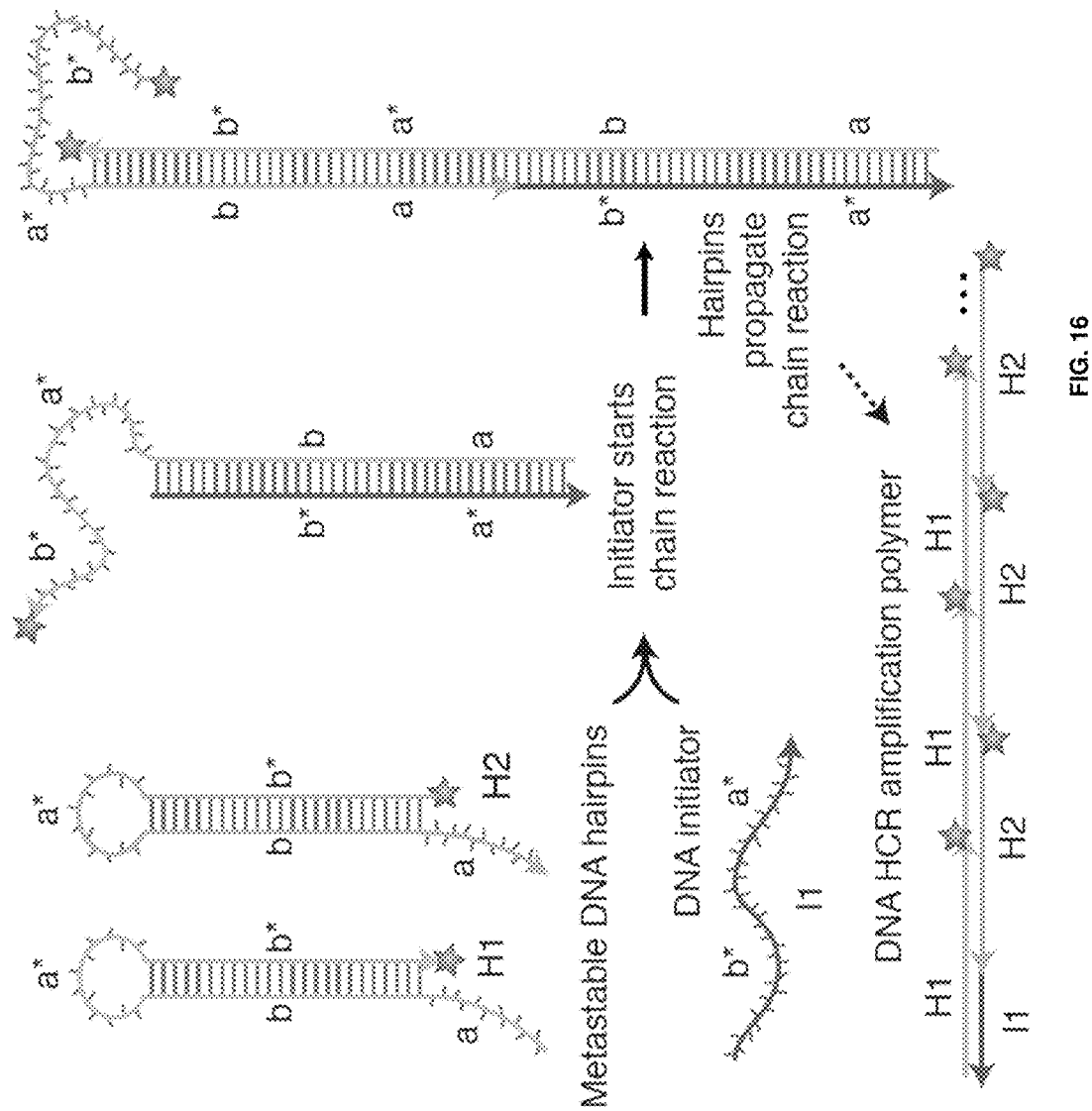
FIG. 16 depicts some embodiments of a HCR mechanism using simplified HCR hairpin monomers.
Figure 1:
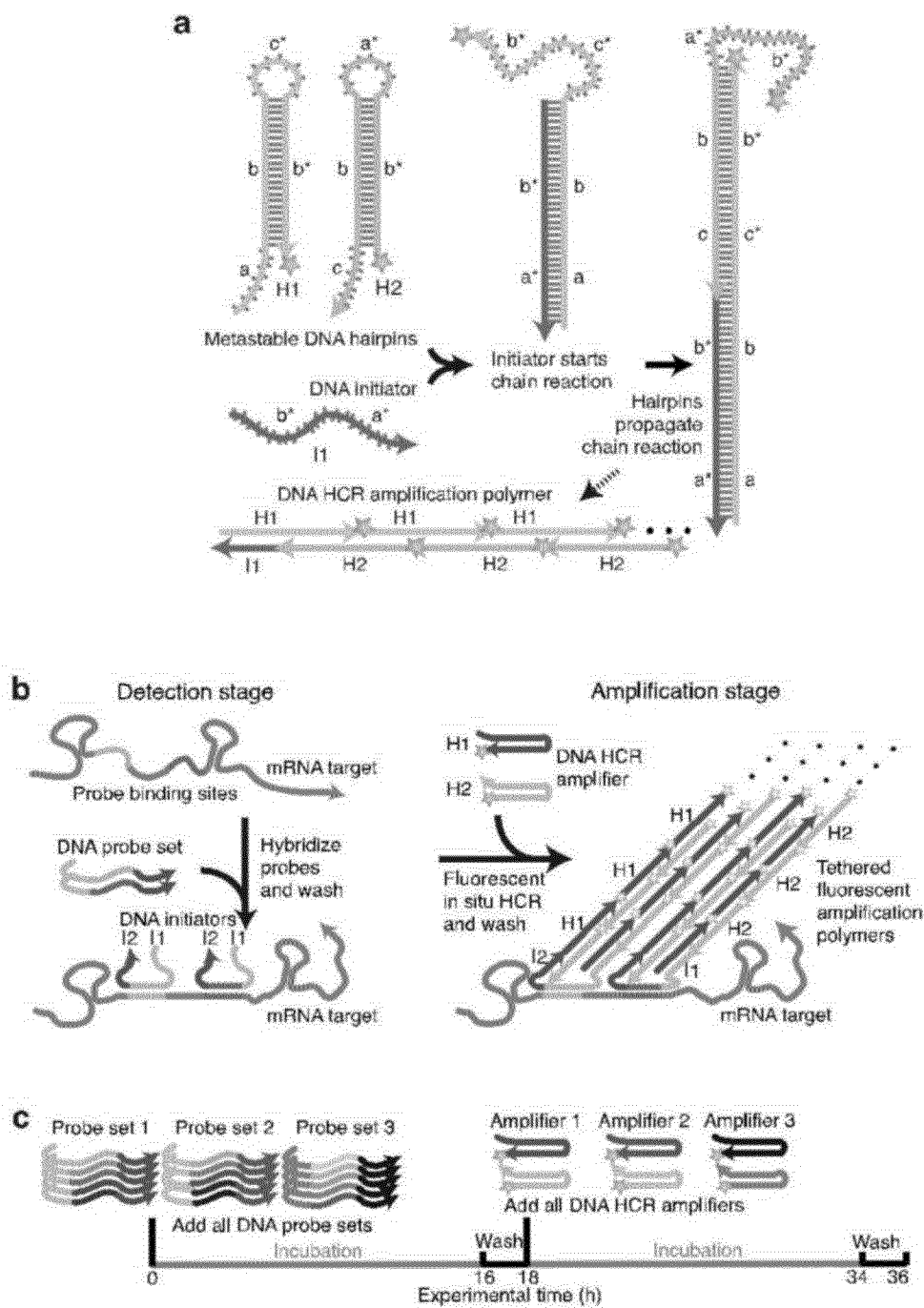
Figure 2:
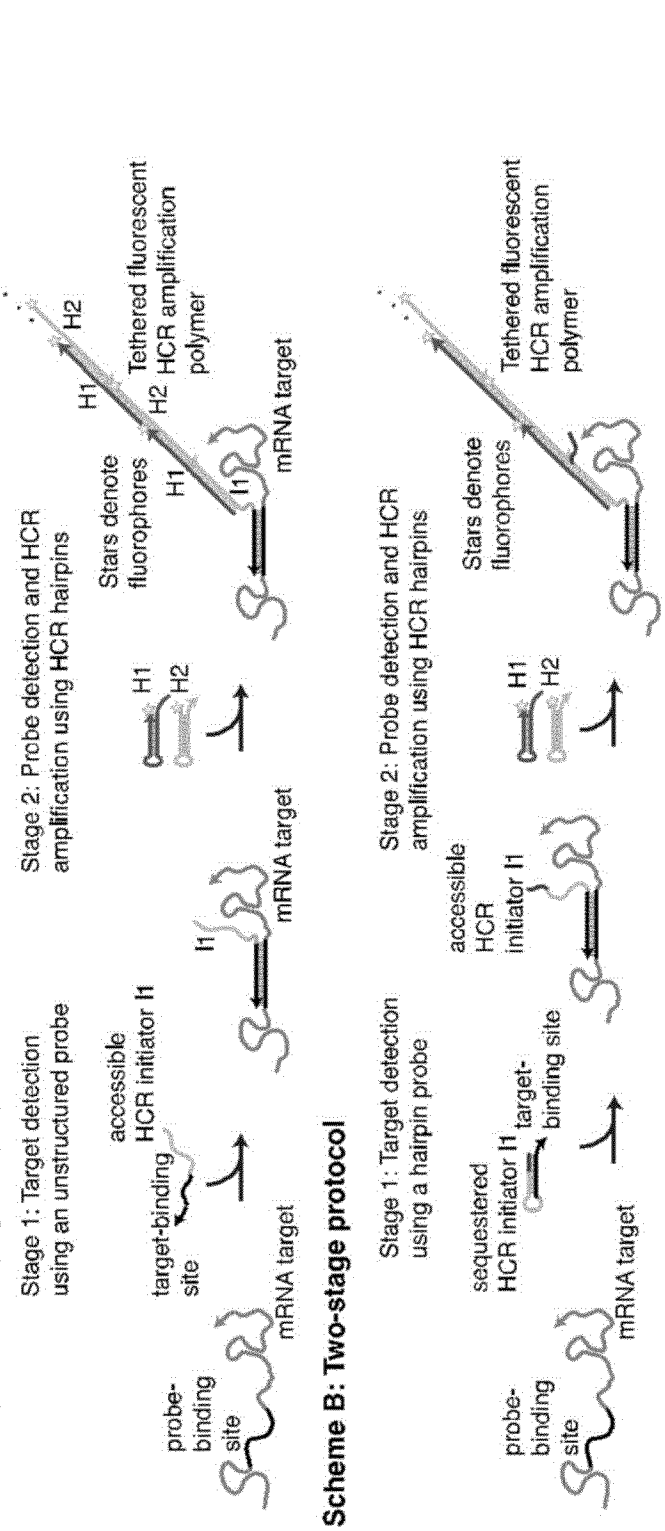
Figure 2:
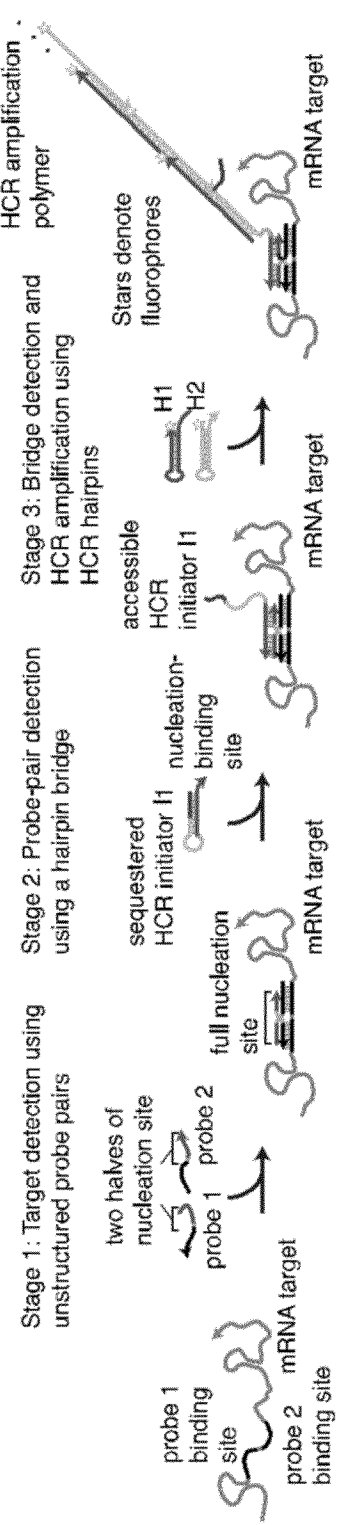
Figure 2:
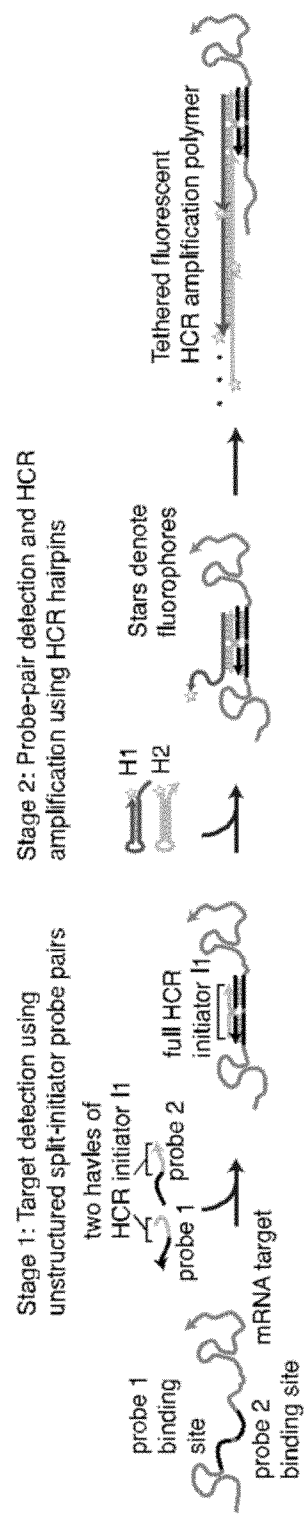
Figure 3:
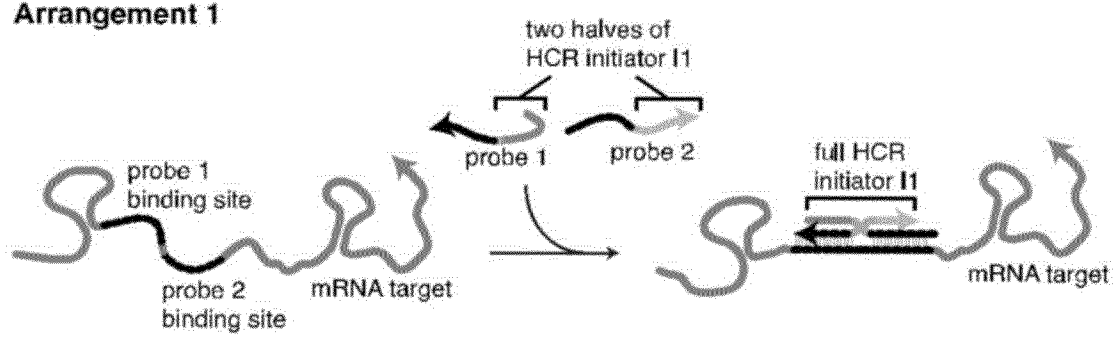
Figure 3:
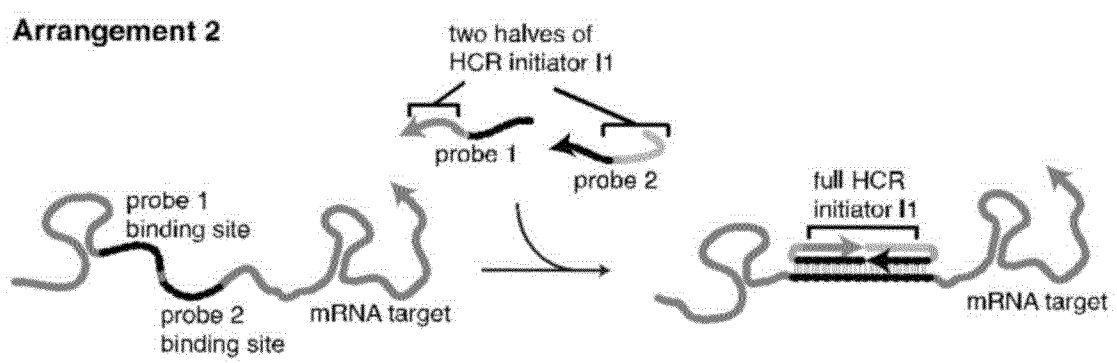
Figure 3:
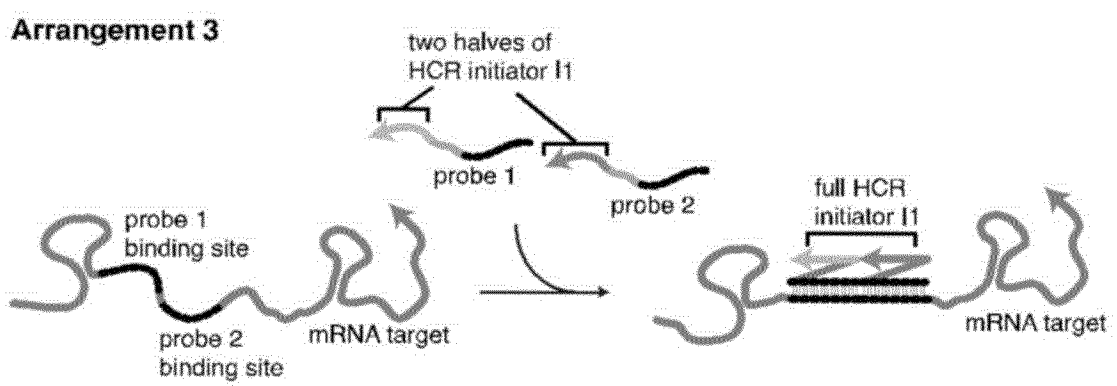
Figure 3:
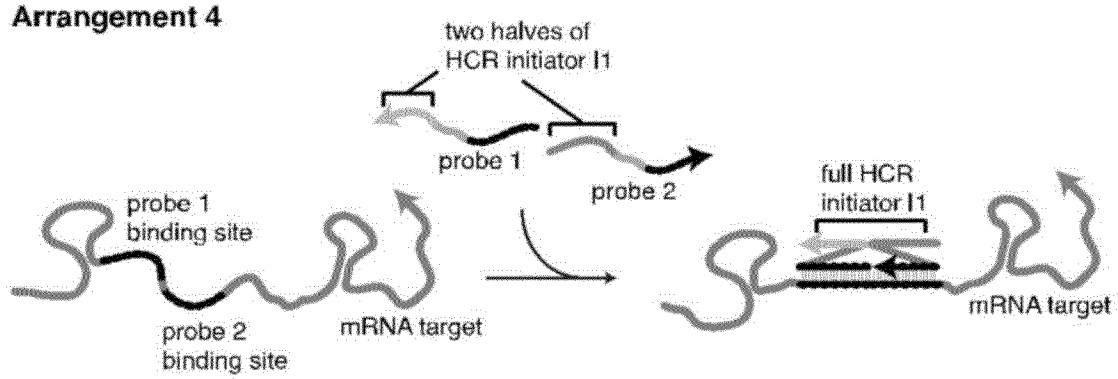
Figure 3:
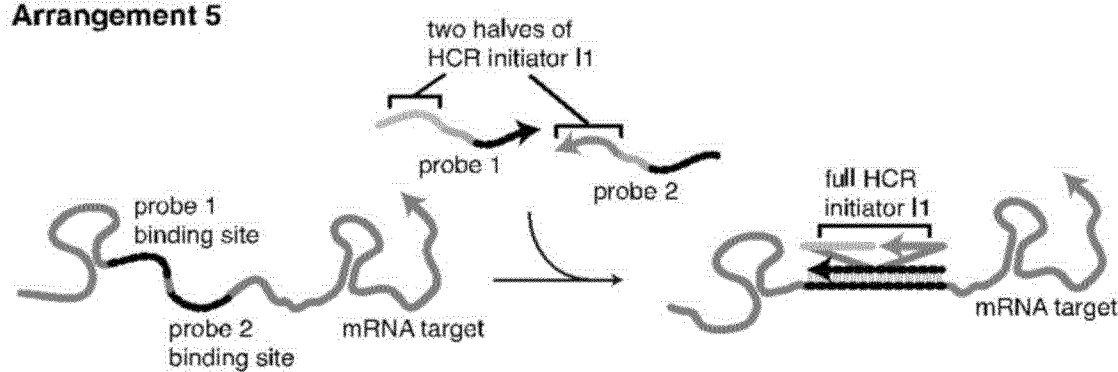
Figure 4:
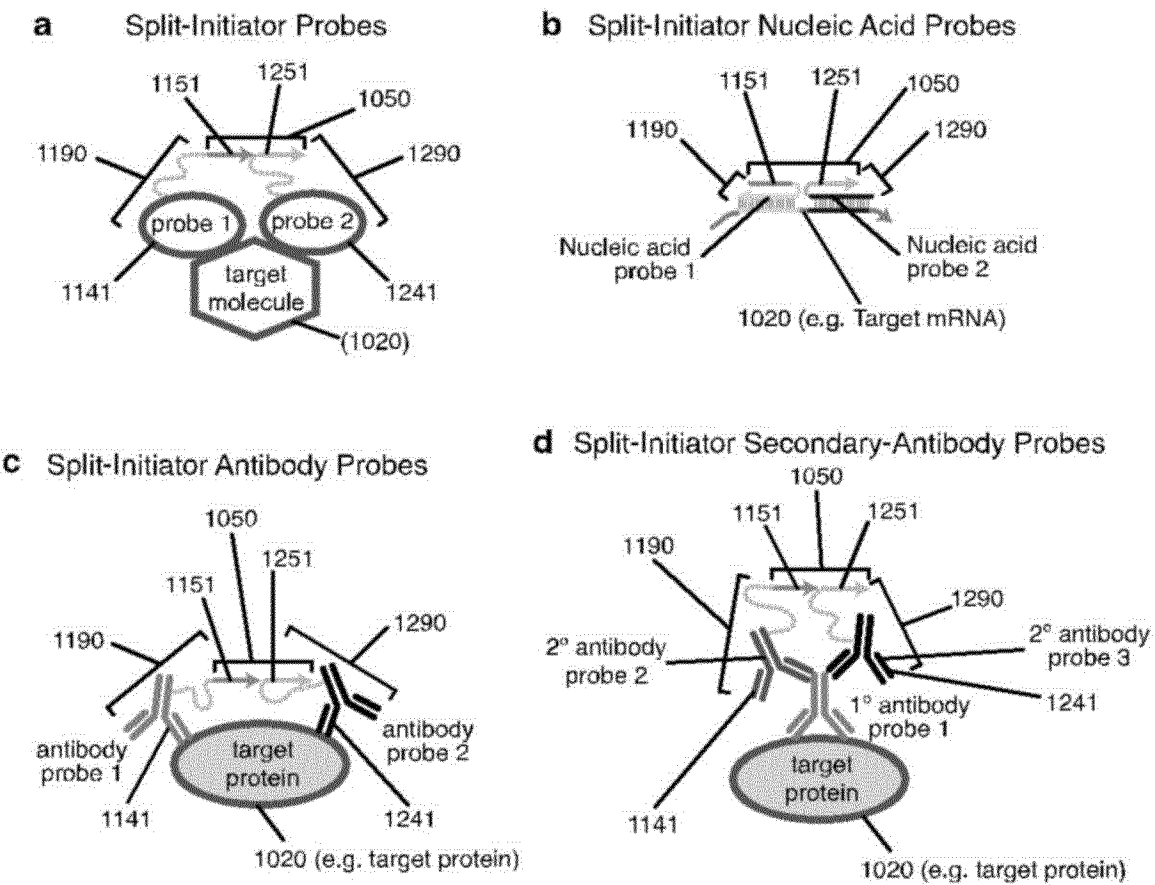
Figure 5:
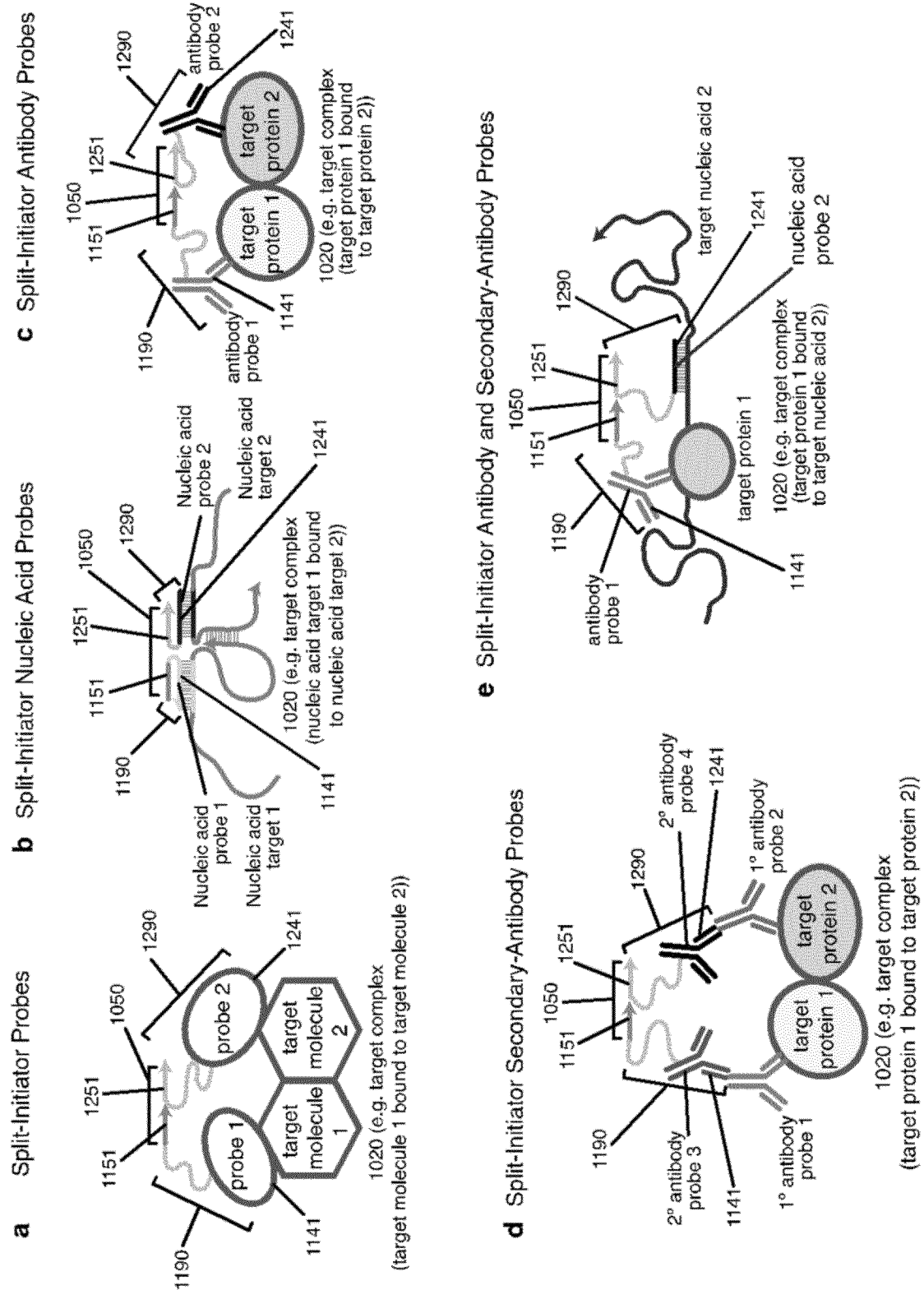
Figure 6:
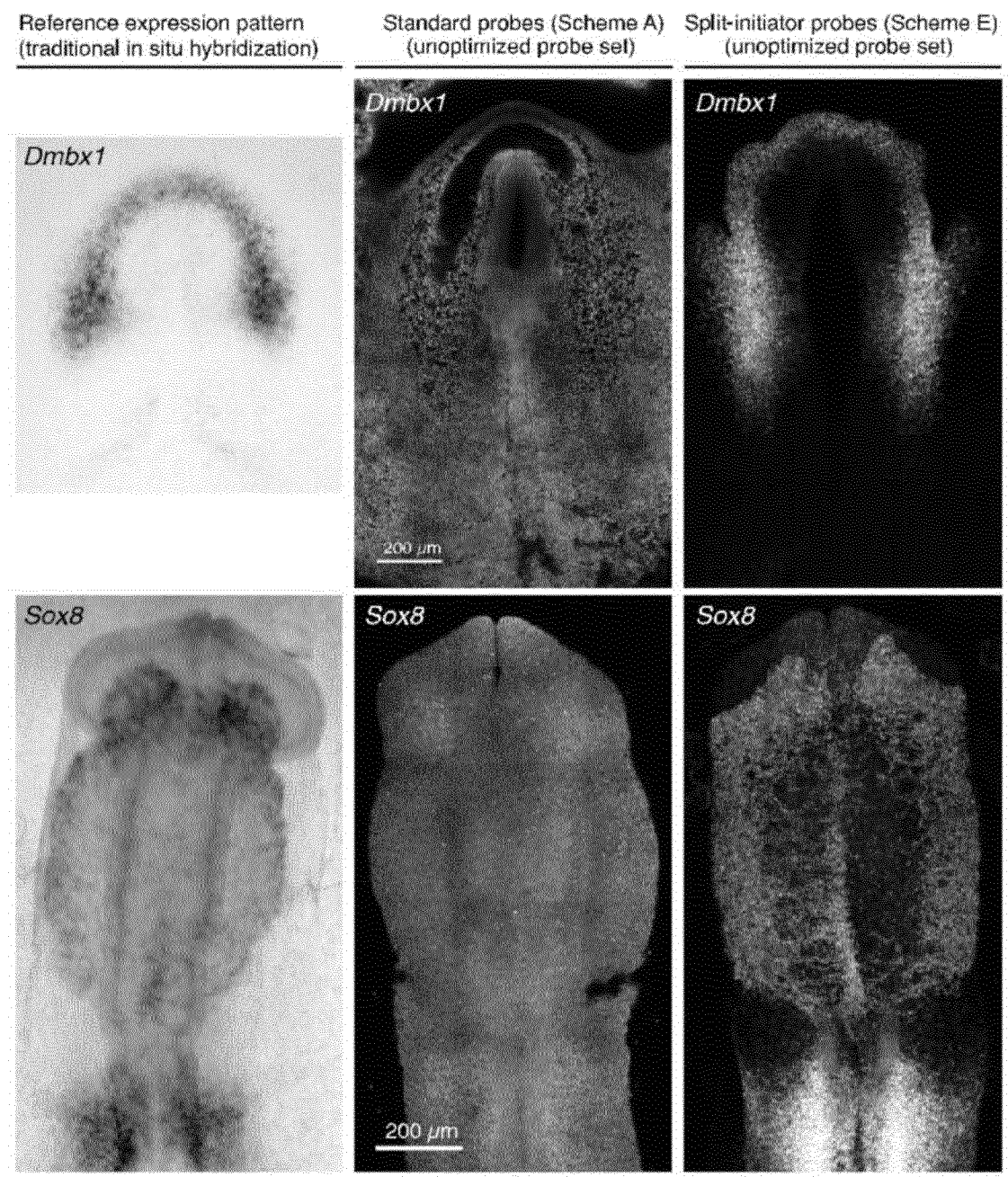
Figure 7:
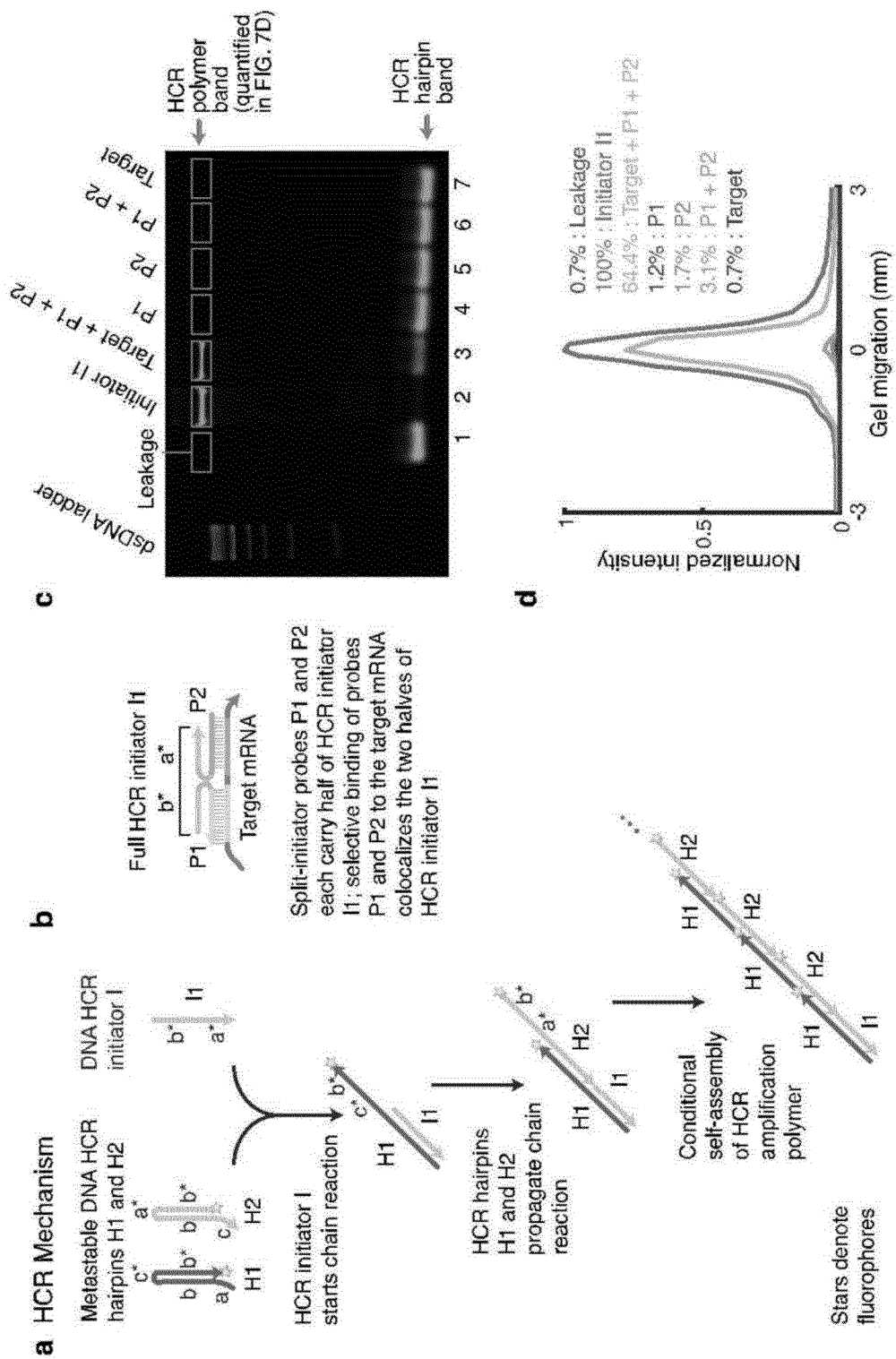
Figure 8:
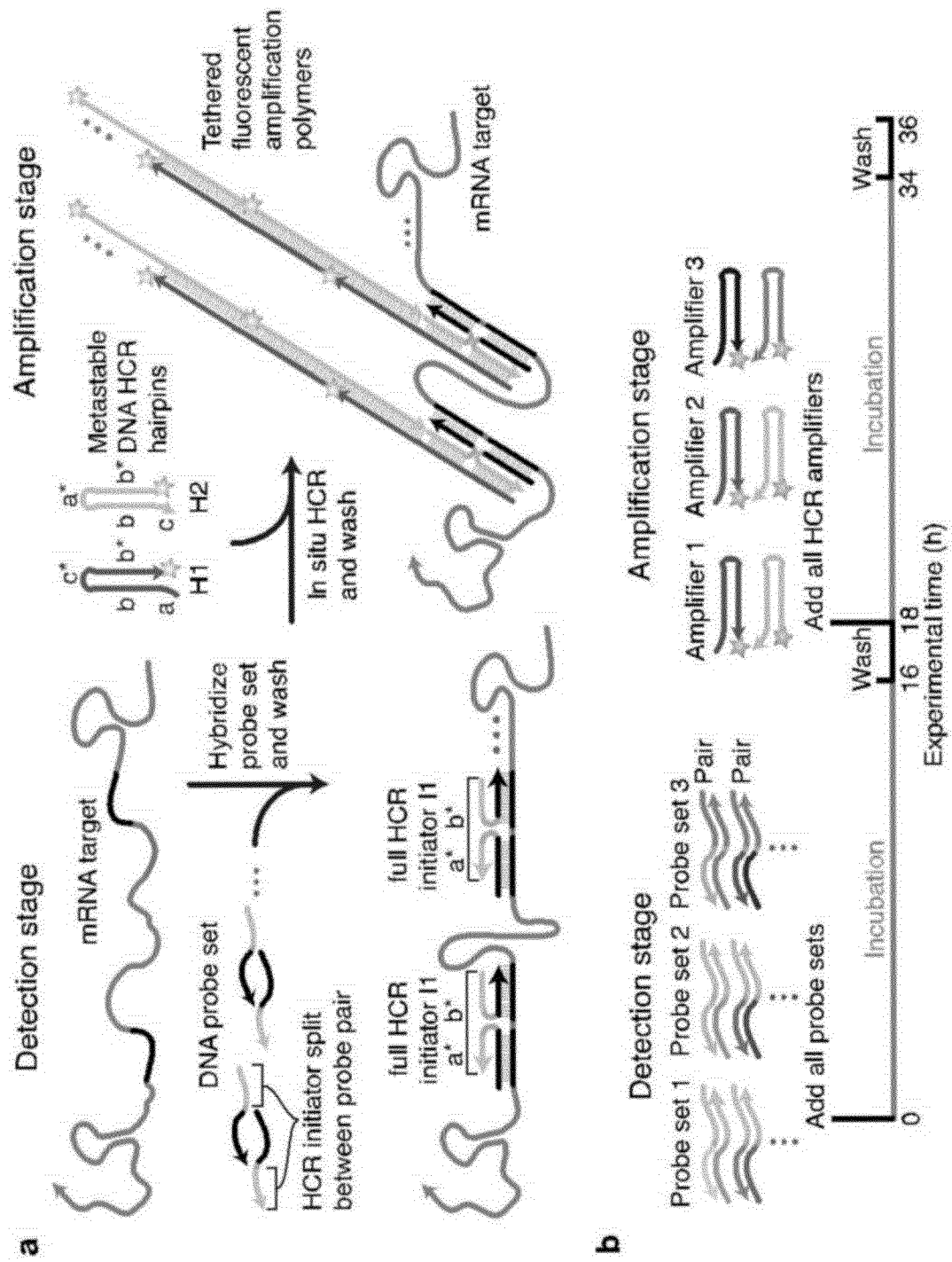
Figure 9:
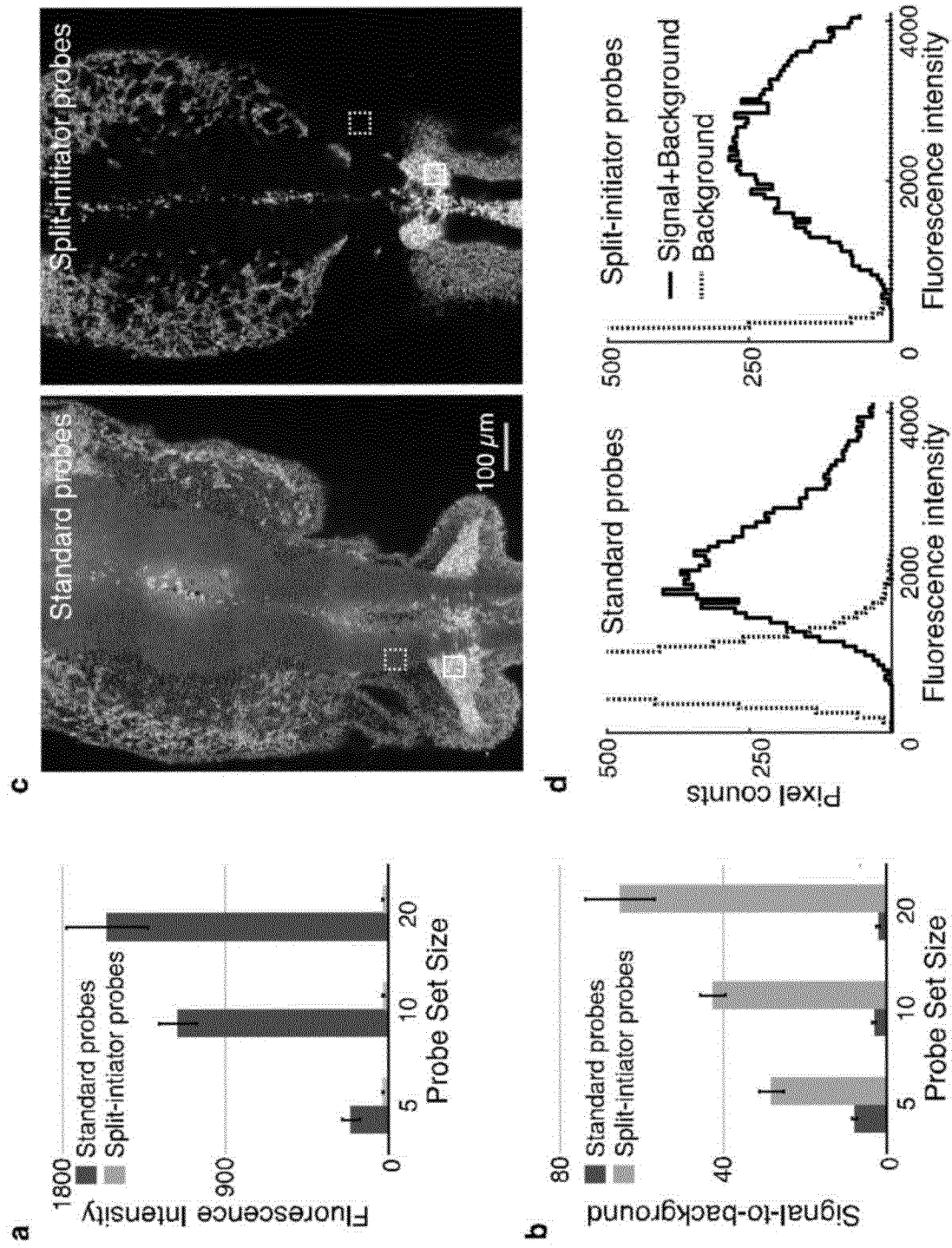
Figure 10:
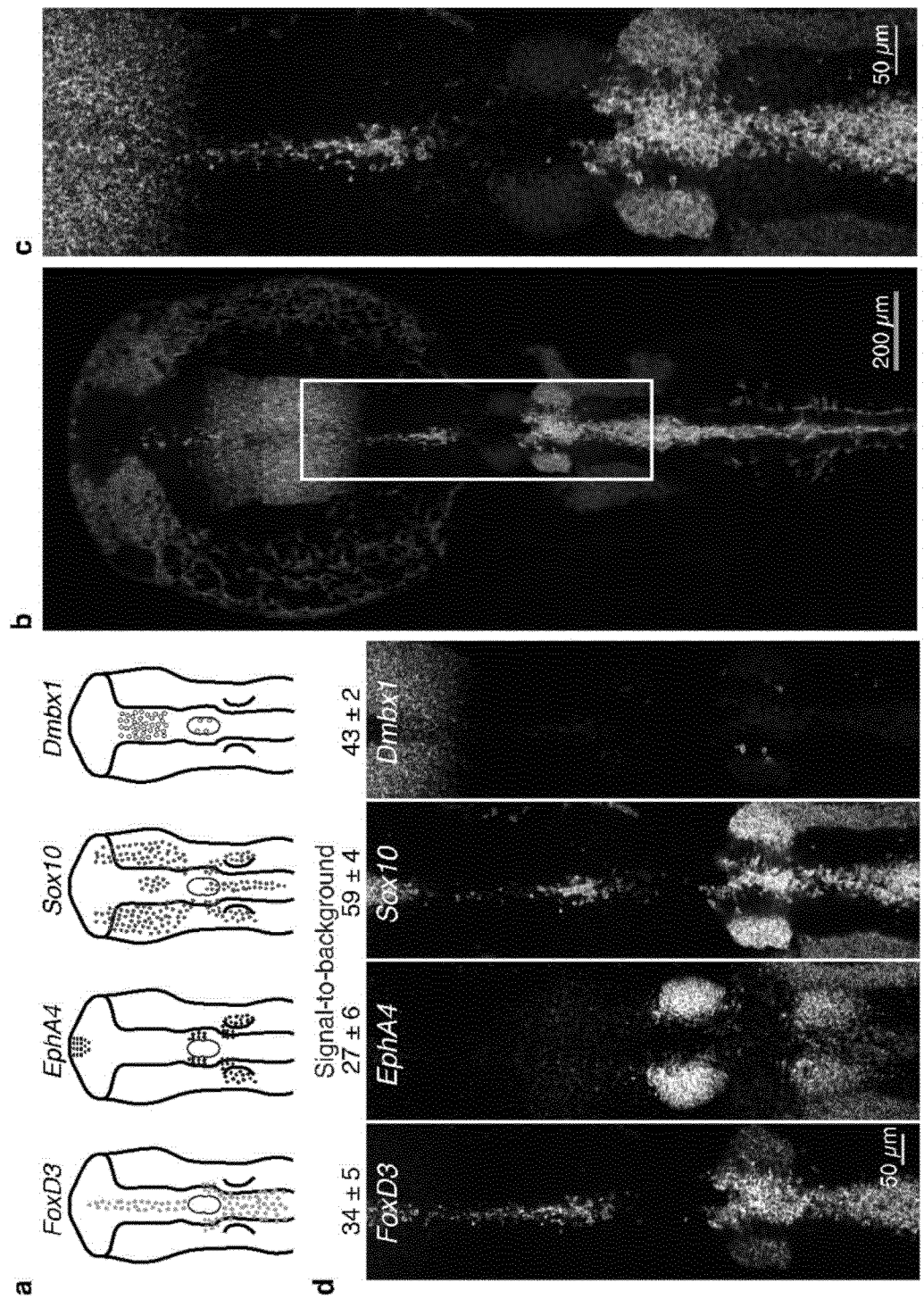
Figure 11:
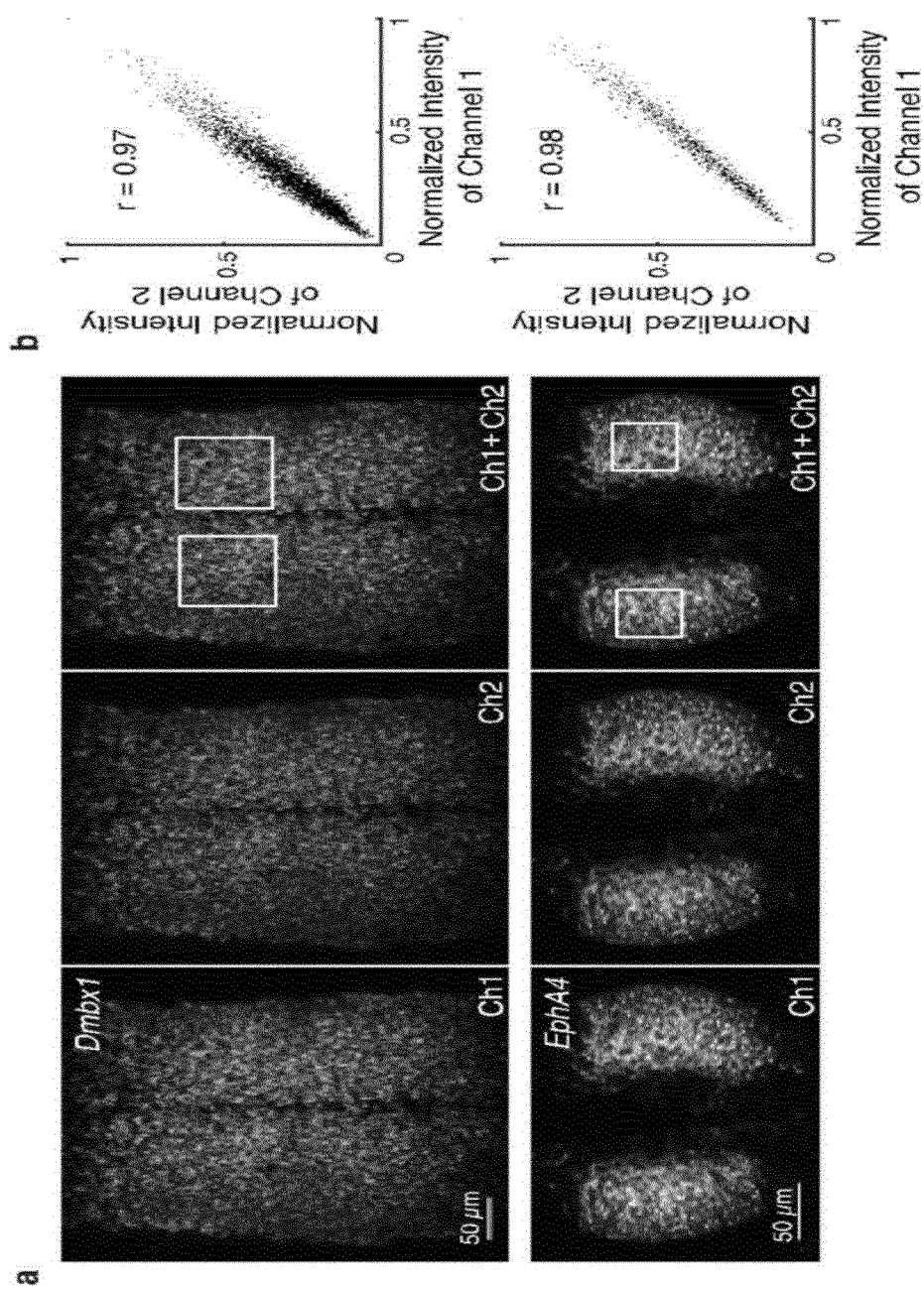

FIG. 16 depicts an HCR mechanism using simplified HCR hairpins. Metastable fluorescent hairpins self-assemble into fluorescent amplification polymers upon detection of a cognate initiator. Initiator I1 nucleates with hairpin H1 via base-pairing to single-stranded toehold 'a', mediating a branch migration that opens the hairpin to form complex I1·H1 containing single-stranded segment 'a*-b*'. This complex nucleates with the second hairpin monomer (hairpin H2) by means of base-pairing to toehold 'a', mediating a branch migration that opens the hairpin to form complex I1·H1·H2 containing single-stranded segment 'b*-a*'. Thus, the initiator sequence is regenerated, providing the basis for a chain reaction of alternating H1 and H2 polymerization steps. Stars denote fluorophores. Arrowhead denotes 3' end of each strand. Note that the two hairpins have the same sequence domains but with opposite strand polarity (a-b-a*-b* for hairpin monomer H1 running 5' to 3') and (a-b-a*-b* for hairpin monomer H2 running 3' to 5').

In some embodiments, "domain a" is the same as domain "c" (e.g., as shown in FIG. 13). That is, both hairpins use the same loop and toehold sequences. This is a special case of the standard HCR case that uses less sequence space to achieve the same functionality.

FISH

In some embodiments, the method is part of a biotechnology protocol. In some embodiments, the method can be part of Fluorescence In Situ Hybridization (FISH). Fluorescence in situ hybridization methods provide biologists with a crucial window into the spatial organization of endogenous biological circuitry by revealing the expression patterns of target mRNAs within cells, tissues, organs, organisms, and ecosystems (1-7). If autofluorescence within the sample is low, sufficient signal can be generated using a fractional initiator probe set containing one or more nucleic acid probes, each carrying one or more fluorescent reporter molecules, and each containing a target binding sequence complementary to a portion of the target mRNA (8-14); in many settings, including whole-mount vertebrate embryos and thick brain sections, this approach does not yield sufficient signal, so probes are instead used to mediate in situ signal amplification to increase the signal-to-background ratio (3, 6, 7, 11, 15-31).

In some embodiments, the method allows one to map target mRNAs within a sample with a high signal-to-background ratio. In some embodiments, a FISH method incorporates in situ signal amplification, in which case all fluorescence within the sample is either amplified signal or some form of background:

Amplified Signal. Amplified signal is generated when probes hybridized specifically to their cognate targets and then subsequently mediate generation of fluorescent amplification products at the site of the target molecule.

Background. All other fluorescence in the sample is some form of background:

Autofluorescence. Autofluorescence is background fluorescence inherent to the sample.

Amplified Background. Amplified background is generated when non-specific binding of a reagent in any stage of a protocol leads to generation of an amplification product in subsequent stages of the protocol.

Unamplified Background. Unamplified background is generated if a fluorescent reagent binds non-specifically in the sample, but does not lead to generation of amplification products.

Hence, the performance of the technique depends both on what goes right (generation of amplified signal) and on what goes wrong (generation of background from any of three sources: autofluorescence, unamplified background, amplified background). To achieve a high signal-to-background ratio in a voxel within an image, it is useful to generate amplified signal that is significantly higher than the total background within the voxel.

Programmable in situ amplification based on the mechanism of hybridization chain reaction (HCR) (32) allows straightforward multiplexing, deep sample penetration, high signal-to-background, and subcellular resolution in diverse organisms (33-35). An HCR amplifier includes two kinetically trapped nucleic acid hairpin molecules (H1 and H2) that co-exist metastably in the absence of a cognate initiator strand (I1; FIG. 1a). Arrival of the initiator triggers a chain reaction in which H1 and H2 hairpins sequentially nucleate and open to assemble into a long nicked double-stranded amplification polymer (32). Using in situ HCR, DNA probes complementary to mRNA targets carry DNA HCR initiators that trigger chain reactions in which metastable fluorophore-labeled DNA hairpins self-assemble into tethered fluorescent amplification polymers (FIG. 1b). The same two-stage in situ hybridization protocol is used independent of the number of target RNAs (FIG. 1c): in the detection stage, all fractional initiator probe sets are hybridized in parallel; in the amplification stage, orthogonal HCR amplifiers operate in parallel.

HCR draws on principles from the disciplines of molecular programming and dynamic nucleic acid nanotechnology to provide isothermal enzyme-free signal amplification in diverse technological settings (36-39) and it is particularly well-suited to the demands of in situ amplification (33, 34). First, HCR is programmable, providing the basis for straightforward multiplexing using orthogonal amplifiers that operate independently and carry spectrally distinct fluorophores. Use of a two-stage protocol independent of the number of target mRNAs is convenient for any sample, but essential for delicate samples such as sea urchin embryos that are easily damaged during serial multiplexing protocols. Second, HCR hairpin monomers do not self-assemble until they encounter a probe carrying the cognate initiator, enabling deep sample penetration prior to growth of bright amplification polymers at the site of target molecules. The use of amplification reagents that are structured hairpins with a duplex stem reduces the potential for non-specific hybridization within the sample and also increases the ease of engineering multiple orthogonal amplifiers. The fact that amplification polymers can carry hundreds of fluorophores (34) makes it possible to achieve high signal-to-background even when autofluorescence is high (e.g., in whole-mount vertebrate embryos (34, 40, 41) or in bacteria contained within environmental samples or other organisms (42-44)). Third, HCR amplification polymers remain tethered to their initiating probes, preventing signal from diffusing away from targets, and leading to subcellular resolution. Fourth, because HCR amplifier sequences are independent of mRNA target sequences, previously validated amplifiers (34) can be used for new studies without modification. To map a new target mRNA, all that is needed is a new DNA fractional initiator probe set carrying DNA initiators for an existing DNA HCR amplifier. Taken together, the properties of in situ HCR lead to straightforward multiplexing, deep sample penetration, high signal-to-background, and subcellular resolution in diverse organisms, offering biologists a dramatically improved window into the spatial organization of biological circuitry. Below is described five Schemes (A, B, C, D, E) that adopt different approaches to optimize the signal-to-background ratio using HCR in situ signal amplification (FIG. 2). A standard in situ HCR approach depicted in FIG. 1b (34) corresponds to Scheme A.

Scheme A: Two-stage protocol: Target detection with an unstructured probe followed by probe detection and HCR amplification using HCR hairpin monomers. An unstructured probe contains a target-binding section (e.g., target binding sequence) and an unstructured HCR initiator sequence. The initiator is accessible to initiate HCR whether or not the probe is hybridized to the cognate target mRNA. HCR hairpin monomers predominantly do not interact except when they are initiated by a cognate HCR initiator; initiation triggers polymerization via sequential hairpin nucleation and opening, yielding an HCR amplification polymer base-paired to the initiator.

Stage 1: Target detection using an unstructured probe: Probes are hybridized within the fixed sample and unused probes are washed away. Probes predominantly bind to the cognate target mRNA but a non-negligible fraction of probes bind elsewhere in the sample. Probes that remain in the sample will trigger amplification during Stage 2, whether or not they are bound to the cognate target mRNA.

Stage 2: Probe detection and HCR amplification using HCR hairpin monomers: HCR hairpin monomers are hybridized within the fixed sample and unused hairpins are washed away. Probes within the sample initiate growth of tethered HCR amplification polymers, generating amplified signal at the site of probes bound to target molecules and amplified background at the site of probes bound elsewhere in the sample. HCR hairpin monomers that bind non-specifically in the sample do not trigger HCR polymerization and hence do not contribute to generation of amplified background, instead contributing a negligible amount of unamplified background.

Performance implications: Scheme A is vulnerable to non-specific probe binding during Stage 1, which leads to generation of amplified background during Stage 2. Because the probe is unstructured, Scheme A has the benefit that the target binding sequence and the HCR initiator sequence are independent; as a result, validated HCR initiators and HCR hairpin monomers can be used for diverse new probes and targets without changing the HCR initiator and HCR hairpin monomer sequences.

Scheme B: Two-stage protocol: Target detection using a hairpin probe followed by probe detection and HCR amplification using HCR hairpin monomers. A hairpin probe contains a target-binding section (e.g., target binding sequence) and an HCR initiator sequence; the HCR initiator is initially inaccessible due to base-pairing within the hairpin probe; if the hairpin probe base-pairs to its cognate target mRNA, the probe changes conformation and the HCR initiator becomes accessible and capable of initiating HCR amplification. HCR hairpin monomers predominantly do not interact except when they are initiated by a cognate HCR initiator; initiation triggers polymerization via sequential hairpin nucleation and opening, yielding an HCR amplification polymer base-paired to the initiator.

Stage 1: Target detection using a hairpin probe: Probes are hybridized within the fixed sample and unused probes are washed away. Probes predominantly bind to the cognate target mRNA but a non-negligible fraction of probes bind elsewhere in the sample. A probe hybridized to a cognate target mRNA changes conformation to expose an accessible HCR initiator, leading to generation of amplified signal in Stage 2. A probe bound elsewhere in the sample has an inaccessible HCR initiator and thus does not trigger HCR amplification, avoiding generation of amplified background in Stage 2.

Stage 2: Probe detection and HCR amplification using HCR hairpin monomers: HCR hairpin monomers are hybridized within the fixed sample and unused hairpins are washed away. A probe hybridized to its cognate target triggers growth of a tethered HCR amplification polymer, generating amplified signal at the site of the target molecule. A probe bound elsewhere in the sample does not trigger amplification, avoiding generation of amplified background. HCR hairpin monomers that bind non-specifically in the sample do not trigger HCR polymerization and hence do not contribute to generation of amplified background, instead contributing a negligible amount of unamplified background.

Performance Implications: Scheme B is not vulnerable to non-specific probe binding during Stage 1, as non-specifically-bound probes do not trigger HCR amplification during Stage 2. Hence, Scheme B has the property that even if reagents bind non-specifically at any stage of the protocol, amplified background will predominantly not be generated. The drawback of Scheme B is that using hairpin probes, there is some degree of sequence complementarity between the target-binding sequence and the HCR initiator sequence. As a result, changing the target-binding section (e.g., target binding sequence) necessitates changing the HCR initiator and HCR hairpin monomer sequences, which is a disadvantage compared to the simplicity of Scheme A.

Scheme C: Three-stage protocol: Target detection with unstructured probe pairs followed by probe-pair detection using an unstructured bridge followed by bridge detection and HCR amplification using HCR hairpin monomers. Unstructured probes come in pairs; each probe contains a target-binding section (e.g., target binding sequence) and half of an unstructured nucleation sequence; for the two probes within a probe pair, the two target-binding section (e.g., target binding sequence)s are complementary to target sections (e.g., proximal subsequences) of the target mRNA such that when the two probes bind specifically to their target sections (e.g. cognate target sites), the two halves of the nucleation sequence are brought into proximity. An unstructured bridge strand contains proximal binding sequences complementary to the two halves of the nucleation sequence; the unstructured bridge strand also contains an HCR initiator that is accessible to initiate HCR whether or not the bridge strand is specifically base-paired to its cognate nucleation site. HCR hairpin monomers predominantly do not interact except when they are initiated by a cognate HCR initiator; initiation triggers polymerization via sequential hairpin nucleation and opening, yielding an HCR amplification polymer base-paired to the initiator.

Stage 1: Target detection using unstructured probe pairs: Probes are hybridized within the fixed sample and unused probes are washed away. Probe pairs predominantly base-pair to their target sections (e.g., cognate target sites), co-localizing the two halves of the nucleation sequence; a non-negligible fraction of probes bind elsewhere in the sample, but probes that are bound non-specifically predominantly do not co-localize the two halves of the nucleation sequence.

Stage 2: Probe pair detection using an unstructured bridge: Unstructured bridge strands are hybridized within the fixed sample under experimental conditions such that a bridge strand predominantly base-pairs stably to the full nucleation sequence created by a cognate probe pair specifically base-paired to proximal target sections (e.g., cognate target sites); furthermore, the experimental conditions are such that the bridge strand predominantly does not base-pair stably to the half-nucleation site carried by an individual probe that is not proximal to its partner probe. A non-negligible fraction of bridges bind non-specifically in the sample; non-specifically bound bridges will trigger HCR amplification during Stage 3, generating amplified background.

Stage 3: Bridge detection and HCR amplification using HCR hairpin monomers: HCR hairpin monomers are hybridized within the fixed sample and unused hairpins are washed away. Bridge strands within the sample initiate growth of tethered HCR amplification polymers; for bridge strands base-paired to their cognate nucleation site formed by a cognate pair of probes base-paired to proximal target sections (e.g., cognate target sites), these polymers represent amplified signal. For bridge strands bound elsewhere in the sample, these polymers correspond to amplified background. HCR hairpin monomers that bind non-specifically in the sample do not trigger HCR polymerization and hence do not contribute to generation of amplified background, instead contributing a negligible amount of unamplified background.

Performance implications: Scheme C is not vulnerable to non-specific probe binding in Stage 1, as bridges predominantly do not base pair stably to isolated probes in Stage 2. However, Scheme C is vulnerable to non-specific binding of bridges in Stage 2, which leads to generation of amplified background in Stage 3. Note that the unstructured bridge in Stage 2 of Scheme C is subject to the same conceptual weakness as the unstructured probe in Stage 1 of Scheme A. The benefit of Scheme C relative to Scheme A is that using Scheme C a library of bridge sequences can be optimized for use in a given species and then those bridge sequences can be reused for diverse new probes and targets without changing the bridges sequences. By comparison, using Scheme A, each new probe sequence would need to be optimized for use in a given species. However, even using optimized bridge sequences with Scheme C, a non-negligible fraction of bridges will bind non-specifically in the sample, generating amplified background in the next stage in the protocol. Likewise, even using optimized probe sequences using Scheme A, a non-negligible fraction of probes will bind non-specifically in the sample, generating amplified background in the next stage in the protocol.

Scheme D: Three-stage protocol: Target detection with unstructured probe pairs followed by probe-pair detection using a hairpin bridge followed by bridge detection and HCR amplification using HCR hairpin monomers. Unstructured probes come in pairs; each probe contains a target-binding section (e.g., target binding sequence) and half of an unstructured nucleation sequence; for the two probes within a probe pair, the two target-binding section (e.g., target binding sequence)s are complementary to target sections (e.g., proximal subsequences) of the target mRNA such that when the two probes bind specifically to their target sections (e.g., cognate target sites), the two halves of the nucleation sequence are brought into proximity. A hairpin bridge contains proximal binding sequences complementary to the two halves of the nucleation sequence; the hairpin bridge also contains an HCR initiator that is initially inaccessible due to base-pairing within the hairpin bridge; if the hairpin bridge base-pairs to both halves of its cognate nucleation sequence, the bridge changes conformation and the HCR initiator becomes accessible and capable of initiating HCR amplification. HCR hairpin monomers predominantly do not interact except when they are initiated by a cognate HCR initiator; initiation triggers polymerization via sequential hairpin nucleation and opening, yielding an HCR amplification polymer base-paired to the initiator.

Stage 1: Target detection using unstructured probe pairs: Probes are hybridized within the fixed sample and unused probes are washed away. Probe pairs predominantly base-pair to their target sections (e.g., cognate target sites), co-localizing the two halves of the nucleation sequence; some probes bind elsewhere in the sample, but probes that are bound non-specifically predominantly do not co-localize the two halves of the nucleation sequence.

Stage 2: Probe-pair detection using a hairpin bridge: Hairpin bridge strands are hybridized within the fixed sample and unused bridges are washed away. Hairpin bridge strands predominantly base-pair stably to the full nucleation sequence created by a cognate probe pair specifically base-paired to proximal target sections (e.g., cognate target sites); a specifically bound hairpin bridge changes conformation to expose an accessible HCR initiator, leading to generation of amplified signal in Stage 3. A hairpin bridge bound elsewhere in the sample has an inaccessible HCR initiator and does not trigger HCR amplification, avoiding generation of amplified background in Stage 3.

Stage 3: Bridge detection and HCR amplification using HCR hairpin monomers: HCR hairpin monomers are hybridized within the fixed sample and unused hairpins are washed away. Specifically-bound hairpin bridges with exposed HCR initiators will trigger growth of tethered fluorescent amplification polymers, generating amplified signal at the site of target molecules. HCR hairpin monomers that bind non-specifically in the sample do not trigger HCR polymerization and hence do not contribute to generation of amplified background, instead contributing a negligible amount of unamplified background.

Performance implications: Scheme D is not vulnerable to non-specific probe binding in Stage 1, as hairpin bridges predominantly do not base pair stably to isolated probes in Stage 2. Furthermore, Scheme D is not vulnerable to non-specific hairpin bridge binding in Stage 2, as non-specifically-bound hairpin bridges do not trigger amplification during Stage 3. Hence, Scheme D shares the important property with Scheme B that even if reagents bind non-specifically at any stage in the protocol, amplified background will predominantly not be generated. The advantage of Scheme D relative to Scheme B is that the bridge nucleation sites, and hence the HCR initiator and HCR hairpin monomer sequences, are independent of the target binding sites in the probes; as a result, a validated HCR initiator and amplifier can be used for diverse new probes and targets without changing the HCR initiator and amplifier sequences.

A drawback of Scheme D relative to Scheme B is the increase in number of stages from two to three.

Scheme E: Two-stage protocol: Target detection with unstructured fractional initiator (aka a split-initiator) probe pairs followed by probe-pair detection and HCR amplification using HCR hairpin monomers. Unstructured fractional initiator (aka a split-initiator) (a.k.a., fractional initiator) probes come in pairs; each probe contains a target-binding section (e.g., target binding sequence) and half of an unstructured HCR initiator; for the two probes within a probe pair, the two target-binding section (e.g., target binding sequence)s are complementary to target sections (e.g., proximal subsequences) of the target mRNA such that when the two probes bind specifically to their target sections (e.g., cognate target sites), the two halves of the HCR initiator are brought into proximity. HCR hairpin monomers predominantly do not interact except when they are initiated by a cognate HCR initiator (full initiator); initiation triggers polymerization via sequential hairpin nucleation and opening, yielding an HCR amplification polymer base-paired to the initiator (full initiator).

Stage 1: Target detection using unstructured fractional initiator (aka a split-initiator) probe pairs: Probes are hybridized within the fixed sample and unused probes are washed away. Probe pairs predominantly base-pair to their target sections (e.g., cognate target sites), co-localizing the two halves of the HCR initiator; some probes bind elsewhere in the sample, but probes that are bound non-specifically predominantly do not co-localize the two halves of the HCR initiator.

Stage 2: Probe-pair detection and HCR amplification using HCR hairpin monomers: HCR hairpin monomers are hybridized within the fixed sample and unused hairpins are washed away. Probe pairs that are hybridized specifically to their target sections (e.g., cognate target sites) co-localize the two halves of an HCR initiator, cooperatively initiating growth of tethered fluorescent HCR amplification polymers, generating amplified signal at the site of target molecules. Probes bound non-specifically do not co-localize the two halves of an HCR initiator, do not trigger HCR amplification, and thus avoid generating amplified background. HCR hairpin monomers that bind non-specifically in the sample do not trigger HCR polymerization and hence do not contribute to generation of amplified background, instead contributing a negligible amount of unamplified background.

Performance Implications: Scheme E is not vulnerable to non-specific probe binding in Stage 1, as isolated fractional initiator (aka a split-initiator) probes do not initiate HCR amplification in Stage 2. Hence, Scheme E shares the important property with Schemes B and D that active background suppression is provided at every stage of the protocol: even if reagents bind non-specifically at any stage in the protocol, amplified background will predominantly not be generated.

Compared to Scheme D, Scheme E has, among other advantages, the advantage that an HCR hairpin monomer serves the role of the hairpin bridge, thus eliminating the need for a separate hairpin bridge and reducing the number of stages in the protocol from three to two. Compared to Scheme C, Schemes D and E have, among other advantages, the advantage that the bridge will not contribute to generation of amplified background if it binds non-specifically. Compared to Scheme B, Scheme E has, among other advantages, the advantage that the HCR initiator and HCR hairpin monomers sequences are independent of the target-binding section (e.g., target binding sequences) in the probes. As a result, validated HCR initiators and HCR hairpin monomers can be used for diverse new probes and targets without changing the HCR initiator and HCR hairpin monomer sequences. Overall, Scheme E has the all of the benefits and none of the drawbacks of Schemes A, B, C, and D: the simplicity of a two-stage protocol, the versatility to re-use validated HCR initiators and HCR hairpin monomers with new target sequences, and the robustness to avoid generating amplified background even if reagents bind non-specifically in the sample at any stage of the protocol.

Figure 2:
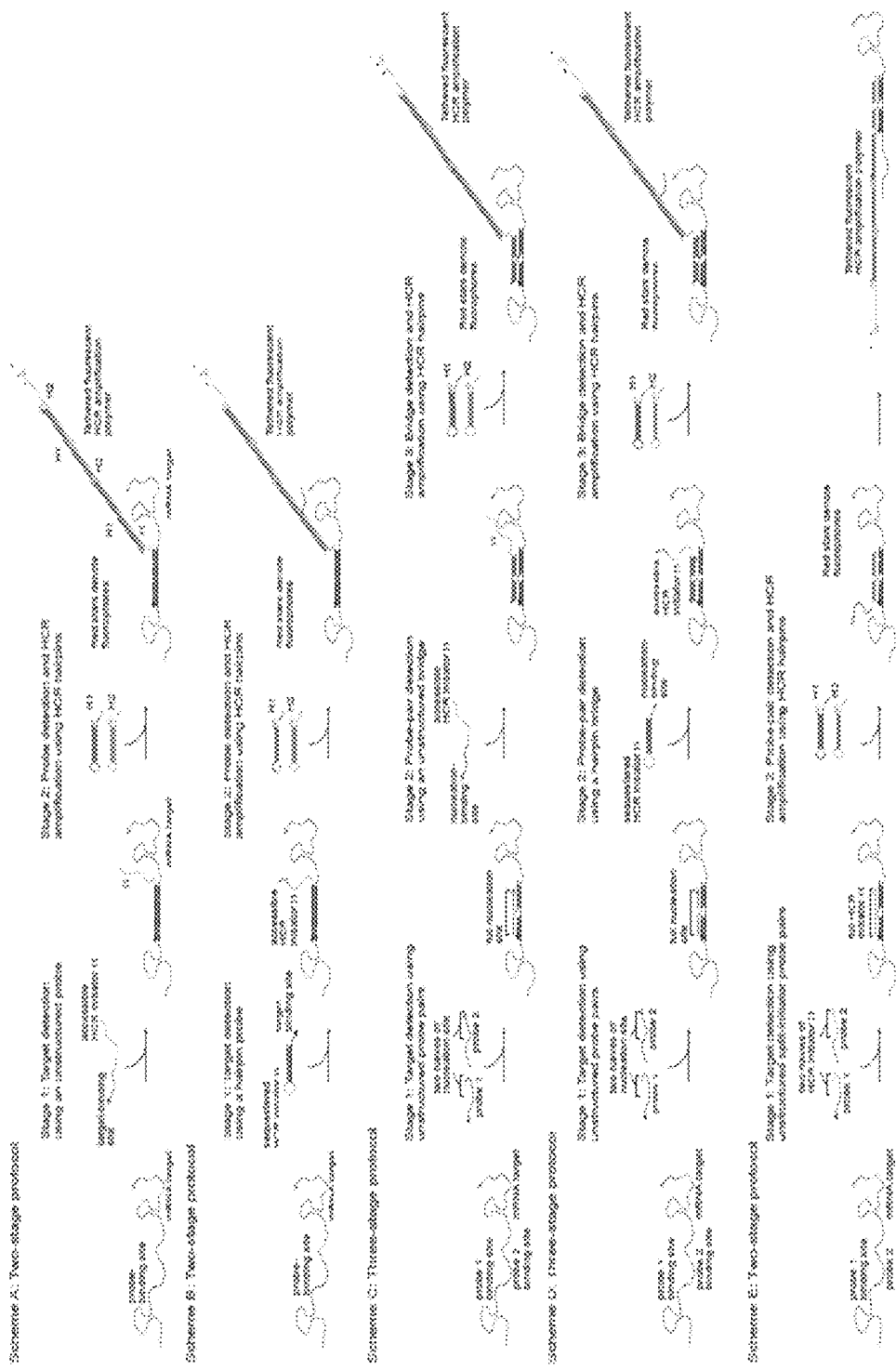
FIG. 2 depicts schematics of in situ HCR using either two-stage or three-stage protocols.

FIG. 1 describes in situ amplification via hybridization chain reaction (HCR). (a) HCR mechanism. Metastable fluorescent hairpins self-assemble into fluorescent amplification polymers upon detection of a cognate initiator. Initiator I1 nucleates with the first hairpin monomer (e.g., hairpin H1) via base-pairing to single-stranded toehold 'a', mediating a branch migration that opens the hairpin to form complex I1 H1 containing single-stranded segment 'c*-b*'. This complex nucleates with the second hairpin monomer (hairpin H2) by means of base-pairing to toehold 'c', mediating a branch migration that opens the hairpin to form complex I1 1 H2 containing single-stranded segment 'b*-a*'. Thus, the initiator sequence is regenerated, providing the basis for a chain reaction of alternating H1 and H2 polymerization steps. Stars denote fluorophores. Arrowhead denotes 3' end of each strand. (b) In situ hybridization protocol (using standard probes of Scheme A).

With regard to the detection stage: fractional initiator probe sets are hybridized to mRNA targets and unused probes are washed from the sample. With regard to the amplification stage: initiators trigger self-assembly of tethered fluorescent amplification polymers and unused hairpins are washed from the sample. (c) Experimental timeline. The same two-stage protocol is used independent of the number of target mRNAs. For multiplexed experiments (three-color example depicted), fractional initiator probe sets for different target mRNAs (five probes depicted per set) carry orthogonal initiators that trigger orthogonal HCR amplification cascades labeled by spectrally distinct fluorophores.

FIG. 2 provides the above noted schematics for five schemes, in summary form. Scheme A: Two-stage protocol: Target detection with an unstructured probe followed by probe detection and HCR amplification using HCR hairpin monomers. Scheme B: Two-stage protocol: Target detection using a hairpin probe followed by probe detection and HCR amplification using HCR hairpin monomers. Scheme C: Three-stage protocol: Target detection with unstructured probe pairs followed by probe-pair detection using an unstructured bridge followed by bridge detection and HCR amplification using HCR hairpins monomer. Scheme D: Three-stage protocol: Target detection with unstructured probe pairs followed by probe-pair detection using a hairpin bridge followed by bridge detection and HCR amplification using HCR hairpin monomers. Scheme E: Two-stage protocol: Target detection with unstructured fractional initiator (aka a split-initiator) probe pairs followed by probe-pair detection and HCR amplification using HCR hairpin monomers. Arrowhead denotes 3' end of each strand.

FIG. 3: Alternative arrangements for two target-binding sites and two fractional initiators (HCR initiator fragments) within a split initiator probe pair. For each Arrangement (1,2,3,4,5), each probe within a probe pair carries half of the full HCR initiator (aka half of the HCR initiator I1); specific binding of the two probes within a pair to the cognate target molecule leads to colocalization of the two halves of the full HCR initiator (aka half of the HCR initiator I1). Arrowhead denotes 3' end of each strand.

FIG. 4 provides additional embodiments in which the split initiator probes are colocalized by a target molecule. (a) Fractional initiator (aka a split-initiator) probes. First fractional initiator probe (Probe 1) and second fractional initiator probe (probe 2) each carry half of HCR initiator I1; selective binding of first fractional initiator probe (Probe 1) and second fractional initiator probe (Probe 2) to the target molecule colocalizes the two halves of HCR initiator I1. (b) Fractional initiator (aka a split-initiator) nucleic acid probes. Nucleic acid probe 1 and nucleic acid probe 2 each carry half of HCR initiator I1; selective binding of nucleic acid probe 1 and nucleic acid probe 2 to the target mRNA colocalizes the two halves of HCR initiator I1. (c) Fractional initiator (aka a split-initiator) antibody probes. Antibody probe 1 and antibody probe 2 each carry half of HCR initiator I1; selective binding of antibody probe 1 and antibody probe 2 to the protein target colocalizes the two halves of HCR initiator I1. (d) Split-initiator secondary-antibody probes. Primary-antibody probe 1 binds selectively to the protein target; secondary-antibody probe 2 and secondary-antibody probe 3 each carry half of HCR initiator I1; selective binding of secondary-antibody probe 2 and secondary-antibody probe 3 to primary-antibody probe 1 colocalizes the two halves of HCR initiator I1.

FIG. 5 provides additional embodiments regarding fractional initiator (aka a split-initiator) probes colocalized by a target complex. (a) Fractional initiator (aka a split-initiator) probes. Target complex comprises molecule 1 bound to molecule 2; first fractional initiator probe (probe 1) and second fractional initiator probe (probe 2) each carry half of HCR initiator I1; selective binding of probe 1 to molecule 1 within the target complex and selective binding of probe 2 to molecule 2 within the target complex colocalizes the two halves of HCR initiator I1. (b) Fractional initiator (aka a split-initiator) nucleic acid probes. Target complex comprises nucleic acid target 1 bound to nucleic acid target 2; nucleic acid probe 1 and nucleic acid probe 2 each carry half of HCR initiator I1; selective binding of nucleic acid probe 1 to nucleic acid target 1 within the target complex and selective binding of nucleic acid probe 2 to nucleic acid target 2 within the target complex colocalizes the two halves of HCR initiator I1. (c) Fractional initiator (aka a split-initiator) antibody probes.

Target complex comprises protein target 1 bound to protein target 2; antibody first fractional initiator probe (probe 1) and antibody second fractional initiator probe (probe 2) each carry half of HCR initiator I1; selective binding of antibody first fractional initiator probe (probe 1) to protein target 1 within the target complex and selective binding of antibody second fractional initiator probe (probe 2) to protein target 2 within the target complex colocalizes the two halves of HCR initiator I1. (d) Fractional initiator (aka a split-initiator) secondary-antibody probes. Target complex comprises protein target 1 bound to protein target 2; primary-antibody first fractional initiator probe (probe 1) binds selectively to protein target 1 within the target complex and primary-antibody second fractional initiator probe (probe 2) binds selectively to protein target 2 within the target complex; secondary-antibody probe 3 and secondary-antibody probe 4 each carry half of HCR initiator I1; selective binding of secondary-antibody probe 3 to primary-antibody first fractional initiator probe (probe 1) and selective binding of secondary-antibody probe 4 to primary-antibody second fractional initiator probe (probe 2) colocalizes the two halves of HCR initiator I1. (e) Fractional initiator (aka a split-initiator) antibody and nucleic acid probes. Target complex comprises protein target 1 bound to nucleic acid target 2; antibody probe 1 and nucleic acid probe 2 each carry half of HCR initiator I1; binding of antibody probe 1 to protein target 1 within the target complex and binding of nucleic acid probe 2 to nucleic acid target 2 within the target complex colocalizes the two halves of HCR initiator I1.

Figure 8:
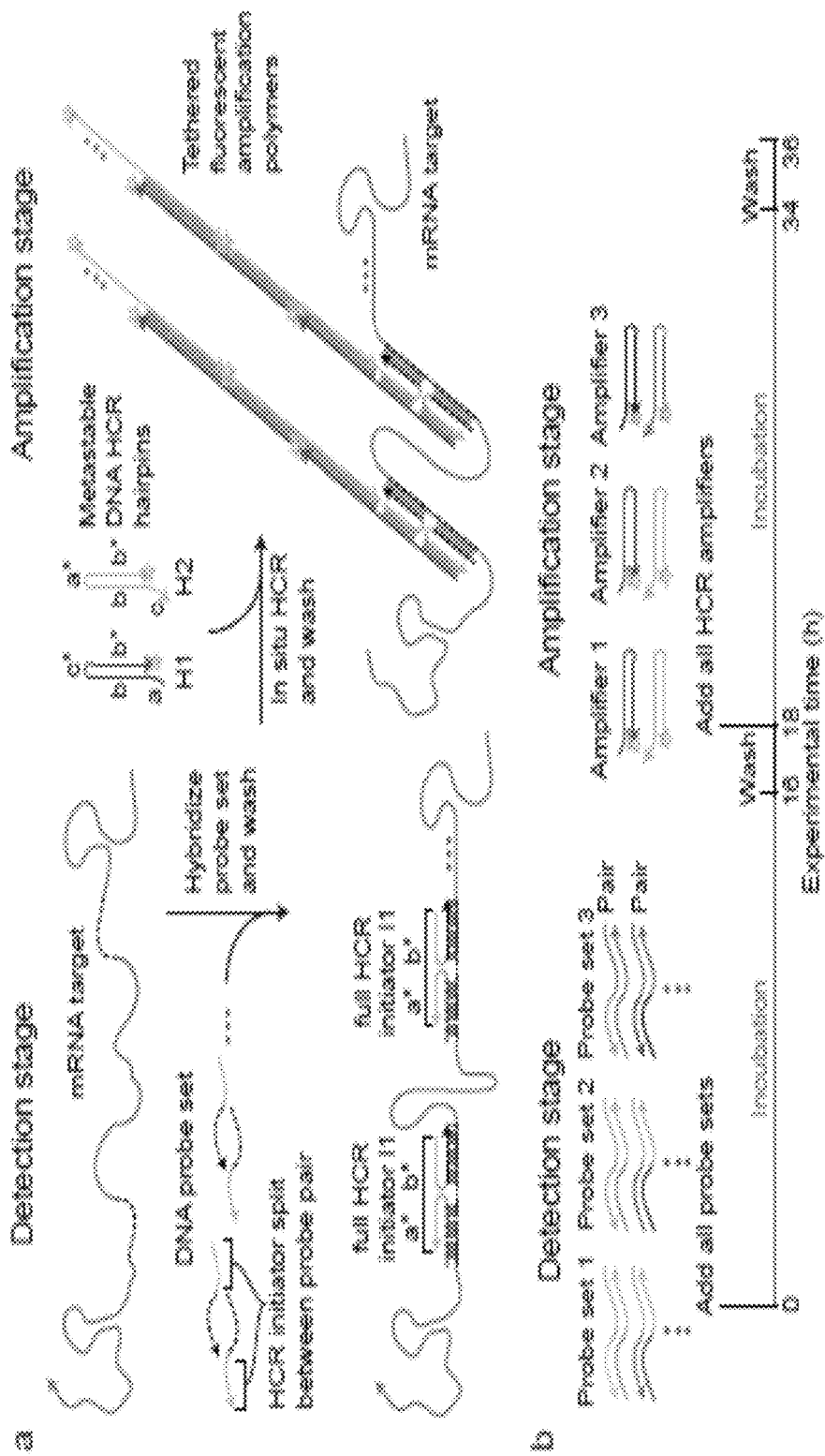
FIG. 8 depicts some embodiments of in situ HCR using fractional initiator probes.

The schematic of FIG. 8 summarizes in situ HCR for imaging nucleic acid target molecules using fractional initiator (aka a split-initiator) nucleic acid probes (Scheme E). In situ HCR using fractional initiator (aka a split-initiator) probes (Scheme E). (a) Two-stage in situ HCR protocol. Detection stage: fractional initiator (aka a split-initiator) probe pairs are hybridized to the target mRNA and unused probes are washed from the sample. Each fractional initiator probe set contains one or more probe pairs that selectively bind to different subsequences along the target mRNA. Each probe within a pair carries half of HCR initiator I1. Selective hybridization of the two probes within a pair to their cognate target binding sites colocalizes the two halves of HCR initiator I1. Amplification stage: full HCR initiator I1 triggers self-assembly of tethered fluorescent amplification polymers and unused H1 and H2 hairpins are washed from the sample. Stars denote fluorophores. (b) Experimental timeline for a multiplexed experiment. A two-stage protocol is used independent of the number of target mRNAs.

Hairpin Monomers

Two or more distinct species of nucleic acid hairpin monomers are preferably utilized in an HCR reaction. Each hairpin monomer species typically comprises at least one region that is complementary to a portion of another hairpin monomer species. However, the monomers are designed such that they are kinetically trapped and the system is unable to equilibrate in the absence of an initiator molecule that can disrupt the secondary structure of one of the monomers. Thus, the monomers are unable to polymerize in the absence of the initiator. Introduction of a full initiator species triggers a chain reaction of alternating kinetic escapes by the two or more monomer species resulting in formation of a polymer. In some embodiments, two hairpin monomers polymerize in the presence of an initiator to form a nicked, double-stranded polymer.

In some embodiments, two or more hairpin monomers are employed that have a hairpin structure. The hairpin monomers can comprise loops protected by long stems. In some embodiments, monomers with a different secondary structure are provided. However, the secondary structure can be such that the monomers are metastable under the reaction conditions in the absence of an initiator nucleic acid. In the presence of a full initiator, the secondary structure of a first hairpin monomer changes such that it is able to hybridize to a sticky end of a second hairpin monomer species. This in turn leads to a change in the secondary structure of the second hairpin monomer, which is then able to hybridize to another first hairpin monomer and continue the process. In this way, once a single copy of the first hairpin monomer interacts with a single copy of the initiator, a chain reaction is produced such that the hairpin monomers are able to assemble into a polymer comprising alternating hairpin monomer species.

A number of criteria can be used to design the monomers to achieve the desired properties. These include, for example and without limitation, sequence symmetry minimization, the probability of adopting the target secondary structure at equilibrium, the ensemble defect corresponding to the average number of incorrectly paired nucleotides at equilibrium relative to the target structure, the test tube ensemble defect corresponding to the concentration of incorrectly paired nucleotides at equilibrium, and hybridization kinetics.

Monomers can be synthesized using standard methods, including commercially available nucleic acid synthesizers or obtained from commercial sources such as Integrated DNA Technologies (Coralville, Iowa).

In some embodiments, monomers are derivitized with a compound or molecule to increase the molecular weight of the polymer resulting from HCR. Preferably they are derivitized at a location that does not interfere with their ability to hybridize. In some embodiments, monomers are derivitized with label binding site. In other embodiments monomers comprise a fluorophore or colorimetric compound that allows the resulting polymers to be visualized.

Initiator

The full initiator can be a nucleic acid molecule. The full initiator is complementary to a portion of a hairpin monomer, preferably a portion of the hairpin monomer that is available for hybridization with the full initiator while the hairpin monomer is in its kinetically trapped state. The full initiator also preferably comprises a sequence that is complementary to a portion of the hairpin monomer adjacent to the sticky end such that hybridization of the full initiator to the sticky end causes a conformational change in the hairpin monomer and begins the HCR chain reaction. For example, the full initiator can comprise a region that is complementary to the first complementary region of the hairpin monomer, as described above.

In some embodiments, the sequence of the full initiator is complementary to the sticky end (initiator complementary region) and first complementary region of a first hairpin monomer. As described herein, in some embodiments this will also influence the sequence of the second complementary region and the loop of the second hairpin monomer species.

In some embodiments, the full initiator is a nucleic acid that is to be detected in a sample or a portion of a nucleic acid that is to be detected. In this case, the sequence of the target nucleic acid is taken into consideration in designing the HCR hairpin monomers. For example, the initiator complement region, preferably a sticky end, of one hairpin monomer is designed to be complementary to a portion of the target nucleic acid sequence. Because the second hairpin monomer will hybridize to the first hairpin monomer, the sequence of the second hairpin monomer will also reflect at least a portion of the sequence of the target nucleic acid.

In some embodiments, amplification of diverse recognition events is achieved by coupling HCR to nucleic acid aptamer triggers. An aptamer is identified that is able to specifically bind an analyte of interest. The analyte is not limited to a nucleic acid but may be, for example, a polypeptide or small molecule. The aptamer is linked to a nucleic acid comprising an initiator region in such a way that the initiator is unavailable to stimulate HCR in the absence of analyte binding to the aptamer.

Detecting HCR

The products of HCR are readily detectable by methods known to one of skill in the art for the detection of nucleic acids, including, for example, agarose gel electrophoresis, polyacrylamide gel electrophoresis, capillary electrophoresis, and gel-filled capillary electrophoresis. As the polymers comprise nucleic acids, they can be visualized by standard techniques, such as staining with ethidium bromide. Other methods also can be suitable including light scattering spectroscopy, such as dynamic light scattering (DLS), viscosity measurement, colorimetric systems and fluorescence spectroscopy. As discussed in more detail, in some methods for in situ imaging and detection, HCR products are fluorescently labeled.

In some embodiments HCR is monitored by fluorescence resonance energy transfer (FRET). Certain monomers are labeled with fluorescent dyes so that conformational changes resulting from HCR can be monitored by detecting changes in fluorescence. In one embodiment, one of a pair of hairpin molecules is labeled with a fluorophore at the junction of the region complementary to the initiator strand and the duplex region and labeled at the opposing side of the duplex region with a quencher molecule. Upon polymerization, the fluorophore and quencher are separated spatially in the aggregated nucleic acid structure, providing relief of the fluorescence quenching. In this case, the presence of a single initiator is amplified by the chain of fluorescent events caused by HCR. In the context of in situ imaging, the presence of a single target molecule can be amplified by the chain of fluorescence events. In addition, for in situ imaging the quenching of fluorescence in unreacted monomers reduces background noise. Thus, unreacted monomers do not need to be removed from the sample.

Relative target abundance can be quantified for different samples by immobilizing the targets (e.g., via fixation within an embryo, or via crosslinking to a blot, or via binding to a bead) and then detecting the targets using fractional initiator probes that are colocalized by the target to trigger HCR, generating a signal that scales linearly with target abundance. If one or more of the samples has known target abundance, absolute quantitation can be performed for the other samples.

Application to In Situ Imaging

Some embodiments of HCR provide for an enzyme-free approach to in situ amplification that can be multiplexed in parallel. Furthermore, HCR amplification triggered by fractional initiator probes provides a means for reducing the background signal resulting from nonspecific probe binding. Fractional initiator probes colocalize a full initiator only if they bind specifically to the cognate target. Hence, they trigger HCR if and only the target is specifically detected, leading to self-assembly of a tethered (to the target) non-covalent 'polymer' built from HCR monomers, preferably hairpin monomers as described above. The HCR monomers can be fluorescently labeled so that the polymers can be detected and the presence and/or location of the target determined.

The HCR hairpin monomers are also referred to herein as "amplifiers" because the polymerization of the monomers upon triggering by a full HCR initiator produces a detectable signal, which is amplified compared to the signal that would be produced by the binding of a single probe to the target. The amplifiers can each be labeled with the same or different fluorophores. For example, the system can be designed to use more than two monomer species per target, with at least one species fluorescently labeled. An HCR amplifier comprising two types of hairpin monomers can have a different fluorophore type labeling each of the two hairpin monomer types. An HCR amplifier comprising four hairpin monomer types can have four different fluorophores, one for each type of hairpin monomer. In such cases, the HCR amplification polymers would be decorated with multiple types of fluorophores in a known ratio (e.g., 1:1 for a polymer made from two alternating types of hairpin monomer, or 1:1:1:1 for a polymer made from four alternating types of hairpin monomer). Fluorescent labels are well known to one of skill in the art and include those, for example, in the "The Handbook-A Guide to Fluorescent Probes and Labeling Technologies," 10th Edition.

In some embodiments, amplifiers within the system are labeled with both a fluorophore and a quencher to form a construct analogous to a "molecular beacon" (Tyagi et al. Nature Biotechnology 14:303-308, 1996). For example, a hairpin monomer can comprise both a fluorophore and a quencher, such that the quencher reduces fluorescence while the monomer is in the hairpin form but not when the monomer is incorporated into an HCR polymer. Thus, molecular beacon versions of HCR monomers can reduce background signal resulting from any unpolymerized monomers, such as those that bind non-specifically or that simply remain unreacted in the sample.

For imaging of biological samples, it can be advantageous to use amplifier components that are small in size to allow penetration into the sample. For example, in some embodiments HCR components less than about 20 nanometers are used, e.g., less than 15 nm, 10 nm, and between about 8 and 16 nm. In some embodiments the HCR hairpin monomers are less than about 8 nm. Standard procedures for in situ imaging can be used to cause the HCR products to enter the sample. The skilled artisan will be able to select the appropriate methods for causing the HCR components to enter the sample.

Advantages of HCR for in situ imaging include, without limitation, the ability to rapidly amplify a signal based on a small amount of analyte present and the ability to image a diversity of analytes in the same sample.

As described herein the use of HCR for in situ detection and imaging provides a number of advantages. Specificity can be achieved using fractional initiator probes that colocalize a full initiator only of two or more fractional initiator probes bind specifically to their target sections (e.g., cognate target sites). Specificity can be achieved by using triggered probes that protect the initiators until the probes bind specifically to targets. Self-quenching HCR monomers can be labeled with fluorophore/quencher pairs that become separated during self-assembly into tethered amplification polymers. This automatic background suppression is particularly useful for in vivo applications where unused amplification components cannot be washed away before imaging. Versatility can be achieved by selecting structure-switching aptamers (Ellinton et al. Nature 346:818-822, 1990 and Tuerk et al. Science 249:505-510, 1990) that generalize the triggered probe concept to the detection of proteins and small molecules. Small probe and amplification monomers, preferably with maximum dimensions of 8-16 nm facilitate sample penetration. Isothermal conditions are ideal for HCR amplification, avoiding damage to the morphology of fixed samples or their components and facilitating in vivo imaging. Multiplexing follows naturally from the use of independent HCR amplifiers that operate simultaneously, for example using spectrally distinct fluorophores to encode unique combinatorial signatures directly into the structure of each HCR product. Sensitive quantitative amplification can be achieved using nonlinear HCR mechanisms that offer exponential growth into tethered polymers of a prescribed finite size. Finally, biocompatibility for in vivo applications follows from the use of nucleic acid amplifier components.

Imaging Multiple Analytes

HCR amplification allows one to amplify multiple targets simultaneously. HCR targeting a number of analytes (for example, gene transcripts or proteins) can be used simultaneously. In some embodiments, each HCR system is labeled with a spectrally distinguishable dye. Accordingly, the number of analytes is equal to the number of spectrally distinguishable dyes that are available. For many situations, this will be sufficient.

To study the expression of multiple mRNAs or proteins, it is desirable to perform multiplexed amplification of all recognition events simultaneously using orthogonal HCR amplifiers. To increase the number of distinct targets that can be imaged using a limited supply of spectrally distinct fluorophores, the unamplified combinatorial multiplexing approach of Levsky and co-workers (Levsky et al. Science 297:836-840, 2002) can be adapted for HCR amplification by labeling the monomers for each amplifier with different unique dye combinations. The use of barcodes with a minimum of two colors provides a basis for screening single-color signals resulting from probes that are not bound specifically.

Therefore, in some embodiments only a single probe pair is used for each target and combinatorial multiplexing is performed by labeling the monomers for each HCR amplifier with different unique dye combinations.

If the H1 and H2 hairpins are end-labeled with different dyes, the HCR product will carry an equal number of each dye by construction. In general, N spectrally distinct fluorophores can be used to address T: $N!/[(N-2)!2!]$ targets with dual-color amplifiers (e.g., 4 dyes for 6 targets, 5 dyes for 10 targets). However, since combinatorial barcodes are not employed as a background diagnostic using this approach, the number of targets can be increased to $T=N!/[N-2]!2!+N$ by allowing single-color amplifiers (e.g., 4 dyes for 10 targets, 5 dyes for 15 targets). Furthermore, it is possible to label HCR monomers with more than one dye to increase the number of targets that can be addressed up to $T=\Sigma_{(i=1,N)}N!/[(N-i)!i!]=2^N-1$ (e.g., 4 dyes for 15 targets, 5 dyes for 31 targets). HCR systems also can be designed that used M hairpins per amplifier.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims. All references cited herein are incorporated by reference in their entirety.

EXAMPLES AND DESCRIPTION

Example 1

Figure 6:
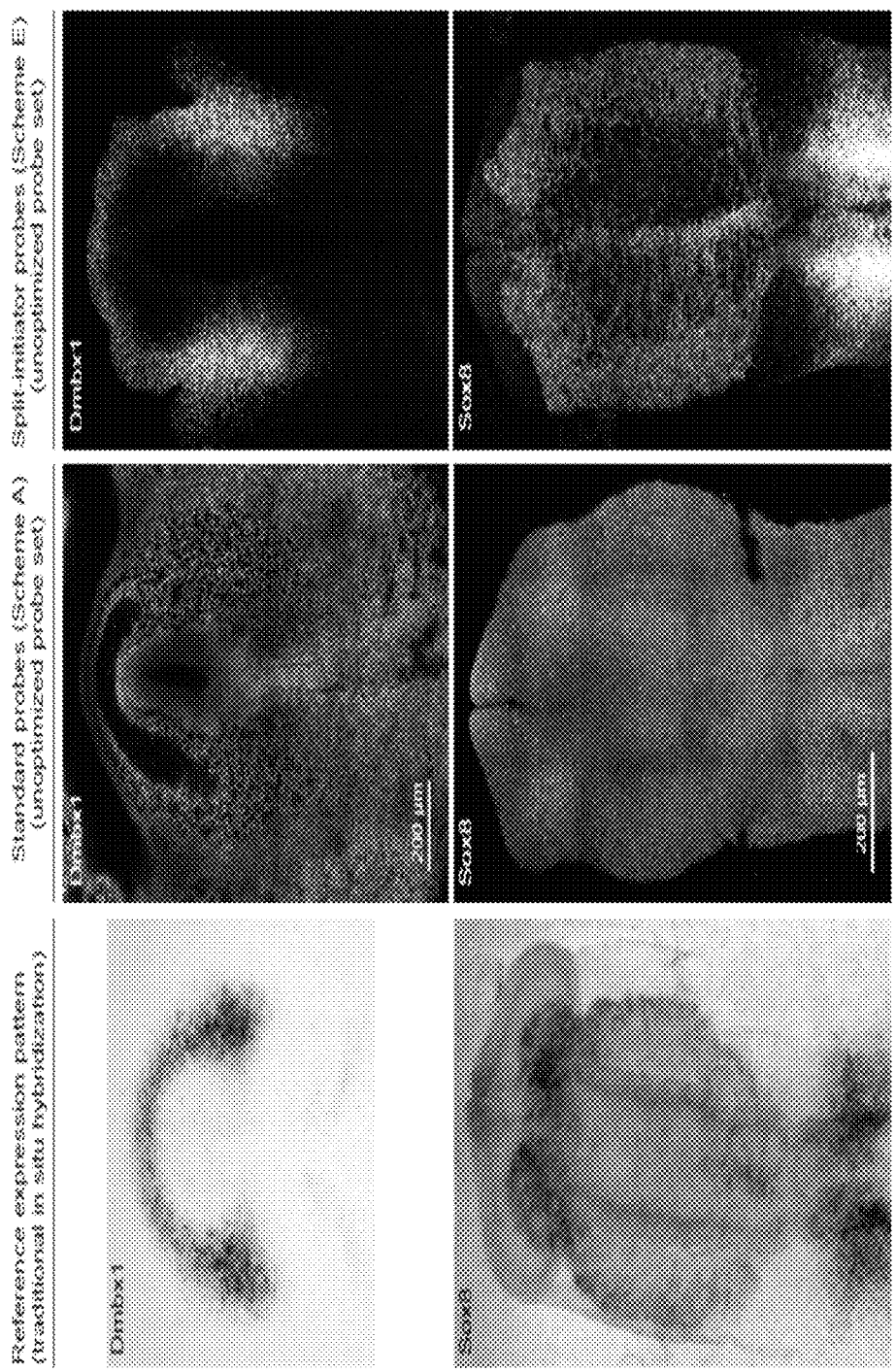
FIG. 6 depicts imaging target mRNAs in whole-mount chicken embryos using unoptimized standard probes and fractional initiator probes.

FIG. 6 demonstrates imaging of two target mRNAs in whole-mount chicken embryos using unoptimized fractional initiator probe sets.

Using standard probes (Scheme A), non-specific probe binding leads to amplified background, resulting in low signal-to-background. Using fractional initiator (aka a split-initiator) probes (Scheme E), automatic background suppression during both stages of the protocol ensures that non-specific probe binding does not lead to amplified background, resulting in high signal-to-background even using an unoptimized fractional initiator probe set. The automatic background suppression property of fractional initiator (aka a split-initiator) probes (Scheme E) is extremely beneficial when mapping the expression pattern of a new target mRNA, allowing rapid generation of high-quality results without requiring tedious fractional initiator probe set optimization (i.e., removal of bad probes observed to bind non-specifically in the sample).

The benefits of active background suppression are illustrated in FIG. 6, depicting imaging of target mRNAs in whole-mount chicken embryos using unoptimized fractional initiator probe sets with either standard probes (Scheme A) or fractional initiator (aka a split-initiator) probes (Scheme E). Target mRNA Dmbx1: Stage HH 7 embryo; target mRNA Sox8: Stage HH10 embryo. With standard probes (Scheme A), low signal-to-background was observed using an unoptimized fractional initiator probe set due to non-specific probe binding, leading to generation of amplified background. With fractional initiator (aka a split-initiator) probes (Scheme E), high signal-to-background is achieved even using an unoptimized fractional initiator probe set; probes that bind non-specifically in the sample do not co-localize the two halves of the HCR initiator, and thus do not trigger HCR signal amplification, avoiding generation of amplified background. Scheme A uses a probe set containing 12 unstructured probes, each containing a target binding site for a different subsequence of the target mRNA. Scheme E uses a fractional initiator probe set containing 12 probe pairs; these 12 pairs address the same target subsequences as the 12 probes for Scheme A. Reference images from GEISHA (Darnell, D. K., Kaur, S., Stanislaw, S., Davey, S., Konieczka, J. H., Yatskievych, T. A., and Antin, P. B. (2007). GEISHA: An In situ hybridization gene expression resource for the chicken embryo. Cytogenet. Genome Res. 117:30-35).

Example 2

Figure 7:
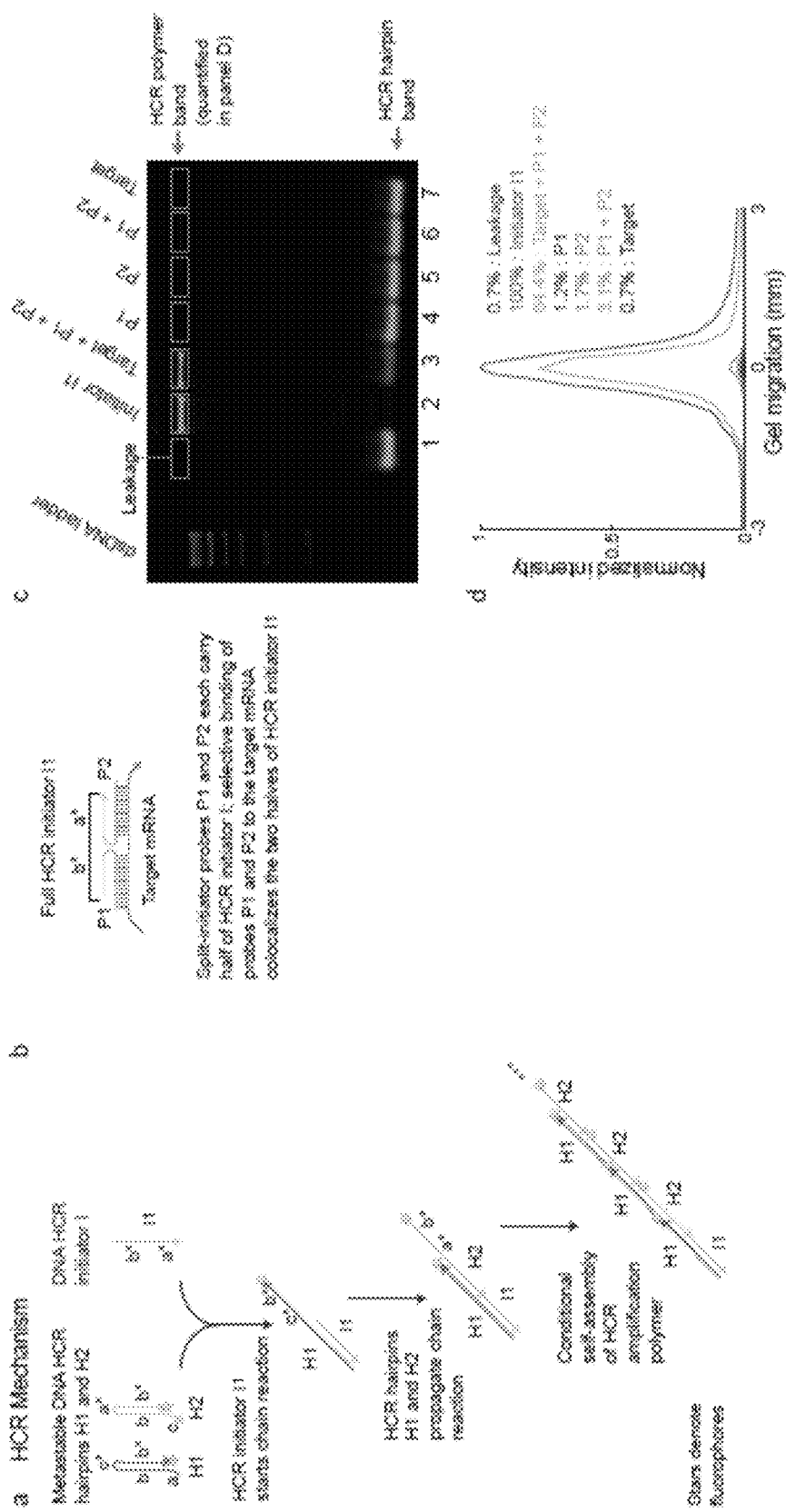
FIG. 7 depicts some embodiments of triggering HCR using fractional initiator probes and displays test tube data demonstrating triggering HCR using fractional initiator probes colocalized by a target. Only a part of the fractional initiator probes is depicted, and the target coordinating the two fractional initiator probes is not depicted. I1 denotes a full initiator formed by two fractional initiator probes colocalized by a target.

Cooperative initiation of HCR using fractional initiator (aka a split-initiator) probes (Scheme E)(FIG. 7). (a) HCR mechanism triggered by a full HCR initiator I1. Metastable fluorescent hairpins self-assemble into fluorescent amplification polymers upon detection of a cognate initiator. Initiator I1 nucleates with the first hairpin monomer (hairpin H1) via base-pairing to single-stranded toehold 'a', mediating a branch migration that opens the hairpin to form complex I1 H1 containing single-stranded segment 'c*-b*'. This complex nucleates with the second hairpin monomer (hairpin H2) by means of base-pairing to toehold 'c', mediating a branch migration that opens the hairpin to form complex I11 H2 containing single-stranded segment 'b*-a*'. Thus, the initiator sequence is regenerated, providing the basis for a chain reaction of alternating H1 and H2 polymerization steps. Stars denote fluorophores. Arrowhead denotes 3' end of each strand. (b) Target-mediated colocalization of fractional initiator (aka a split-initiator) probes (Scheme E). Fractional initiator (aka a split-initiator) probes P1 and P2 each carry half of HCR initiator I1. Selective binding of P1 and P2 to the target mRNA colocalizes the two halves of HCR initiator I1, allowing cooperative initiation of the HCR amplification cascade of panel A.

(c) In vitro validation of cooperative initiation of HCR using split-initiator probes P1 and P2 (Scheme E). Reaction conditions: hairpins H1 and H2 at 0.5 μM each (Lanes 1-7); oligos I1, P1, P2, and/or Target at 5 nM each (Lanes as noted on the gel); 5 SSCT buffer; overnight reaction at room temperature. Hairpins H1 and H2 labeled with Alexa 647 fluorophore. dsDNA 1 kb ladder pre-stained with SYBR Gold. Lane 1: Metastable hairpins H1 and H2 exhibit minimal leakage out of their kinetically trapped states in the absence of HCR initiator I1. Lane 2: Full conversion of HCR hairpin monomers H1 and H2 into amplification polymer in the presence of HCR initiator I1 (I1 as an oligo). Lane 3: Strong conversion of hairpins H1 and H2 to polymer in the presence of Target and both fractional initiator (aka a split-initiator) probes P1 and P2, demonstrating cooperative initiation of HCR. Lanes 4-6: Minimal conversion of HCR hairpin monomers H1 and H2 into polymer in the presence of probe P1, probe P2, or both probes P1 and P2, demonstrating active background suppression. Lane 7: Minimal conversion of HCR hairpin monomers H1 and H2 into polymer in the presence of Target alone. (d) Quantification of the polymer bands in panel c. Multi Gauge software (Fuji Photo Film) was used to calculate the Alexa 647 intensity profile surrounding the polymer band for Lanes 1-7. Each intensity profile is displayed for ±3 mm of gel migration distance with the peak value centered at 0. The quantification percentages were calculated using Multi Gauge with auto-detection of signal and background; the calculated values were normalized to the measured value for Lane 2.

The gel study of FIG. 7c demonstrated cooperative initiation of HCR using fractional initiator (aka a split-initiator) probes (Scheme E). Lane 1 shows that there is minimal leakage of hairpins H1 and H2 out of their kinetically trapped states in the absence of HCR initiator I1. As a positive control, Lane 2 demonstrates conversion of metastable HCR hairpin monomers H1 and H2 into polymer in the presence of full HCR initiator I1 (where I1 is a single oligo).

Using fractional initiator (aka a split-initiator) probes, strong conversion of metastable HCR hairpin monomers H1 and H2 into polymer were observed if the target was present together with fractional initiator (aka a split-initiator) probes P1 and P2. However, minimal conversion to polymer was observed if P1 or P2 is present alone (Lanes 4 and 5), or if P1 and P2 were present together but in the absence of the Target (Lane 6).

These results demonstrated the active background suppression properties of fractional initiator (aka a split-initiator) probes (Scheme E): probes that are not colocalized via selective hybridization to the target predominantly do not trigger HCR amplification. The fact that in the absence of the target, P1 and P2 do not trigger HCR even when they are both present in solution (Lane 6), indicates that fractional initiator probes provide automatic background suppression even in the absence of washes.

Example 3

Figure 9:
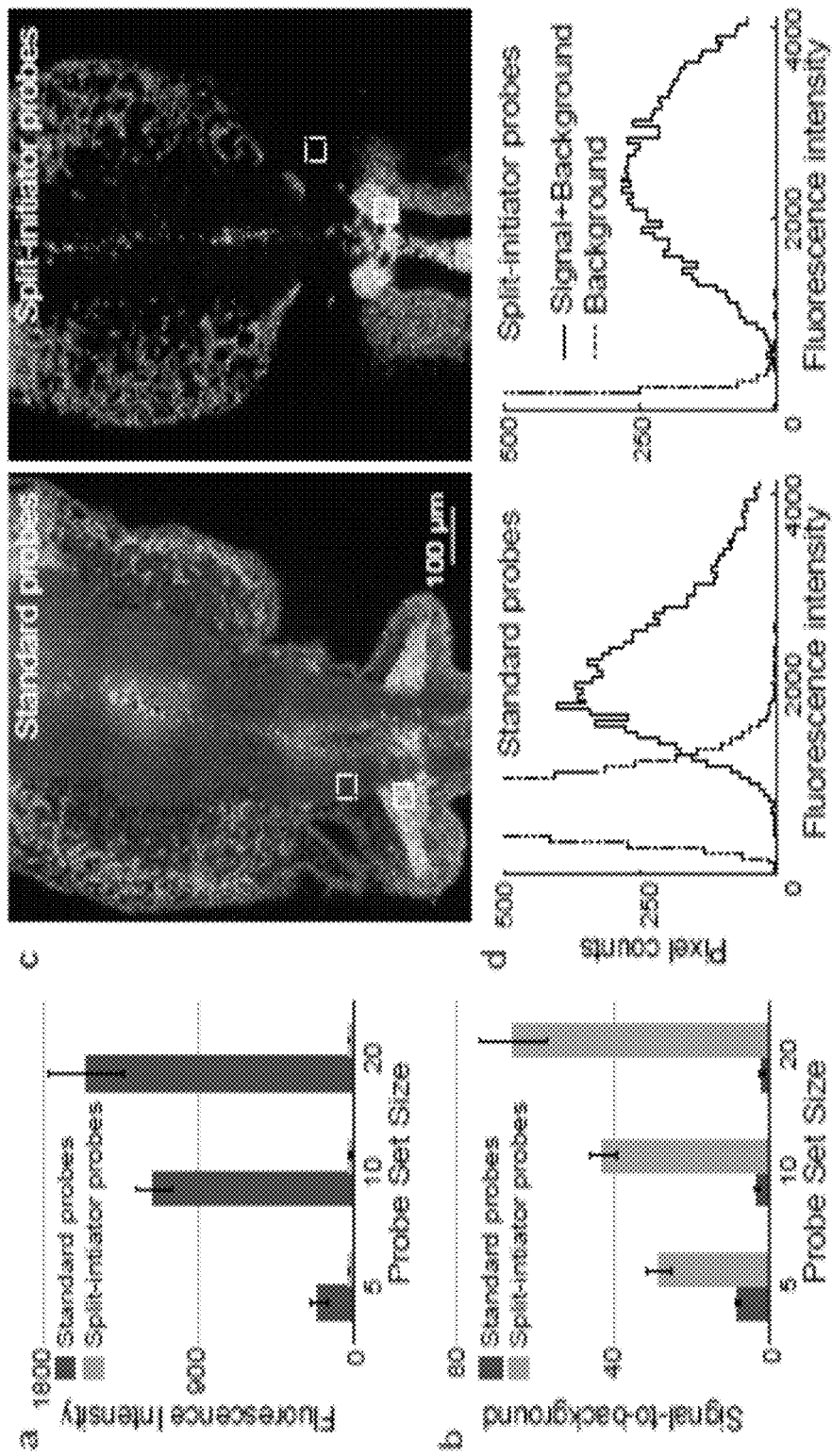
FIG. 9 depicts background and signal-to-background using standard probes and fractional initiator probes.

FIG. 9 compares the performance of standard probes (Scheme A) and fractional initiator (aka a split-initiator) probes (Scheme E) as the size of the probe set is increased for imaging of a mRNA target in whole-mount chicken embryos. For tests with standard probes, an optimized probe set of 5 probes was used, and then these probes were augmented with additional unoptimized probes to form probe sets of 10 probes and 20 probes. For tests with fractional initiator (aka a split-initiator) probes, probe sets were used with 5, 10, and 20 probe pairs, where each probe pair targets approximately the same binding site as the corresponding standard probe. Using standard probes, increasing the probe set size resulted in a substantial increase in background (panel a) and a corresponding decrease in signal-to-background as a result of some subset of the additional probes binding non-specifically within the sample.

These data illustrate the importance of probe set optimization using standard probes (Scheme A) that do not provide active background suppression: if there are any bad probes in the probe set, they will undermine performance by generating amplified background. In contrast, using fractional initiator (aka a split-initiator) probes (Scheme E), as the number of probe pairs increases from 5 to 10 to 20, the background remains approximately constant (panel a) and the signal-to-background ratio increases monotonically (panel b).

These data illustrate the significant benefit of automatic background suppression using fractional initiator (aka a split-initiator) probes: even if there are bad probes in the fractional initiator probe set, they do not generate amplified background, making it straightforward to increase signal-to-background by increasing the number of probes without performing probe set optimization. Representative images using the probe sets with 20 probes (standard probes) or 20 probe pairs (fractional initiatory (split-initiator) probes) are shown in panel c. Representative pixel intensity distributions for these images are shown in panel d. With fractional initiator (aka a split-initiator) probes, the pixel intensity distributions for background and signal+background are predominantly non-overlapping.

The following is provided for slightly more detail for FIG. 9, which presents background and signal-to-background using standard probes (Scheme A) and fractional initiator (aka a split-initiator) probes (Scheme E). (a) Fluorescent background using probe sets with 5, 10, or 20 probes (standard probes) vs 5, 10, or 20 probe pairs (fractional initiator (aka a split-initiator) probes). Unoptimized standard probes resulted in non-specific probe binding, leading to generation of amplified background. Unoptimized fractional initiator (aka a split-initiator) probes that bind non-specifically in the sample did not co-localize the two halves of the HCR initiator, and thus did not trigger HCR signal amplification, avoiding generation of amplified background. (b) Signal-to-background ratio for the probe sets of panel a. Fractional initiator (aka a split-initiator) probes with active background suppression outperformed unoptimized standard probes in signal-to-background measurements. (c) Confocal micrographs in the neural crest of fixed whole-mount chicken embryos. Probe sets: 20 probes for standard probes of Scheme A, 20 probe pairs for fractional initiator (aka a split-initiator) probes of Scheme E. (d) Pixel intensity histograms for Signal+Background (pixels with in solid boundary in panel c) and Background (pixels within dashed boundary in panel c). For each image, the total number of pixels within solid and dashed boundaries is the same. Embryos fixed: stage HH10. Target: Sox10.

Example 4

Figure 10:
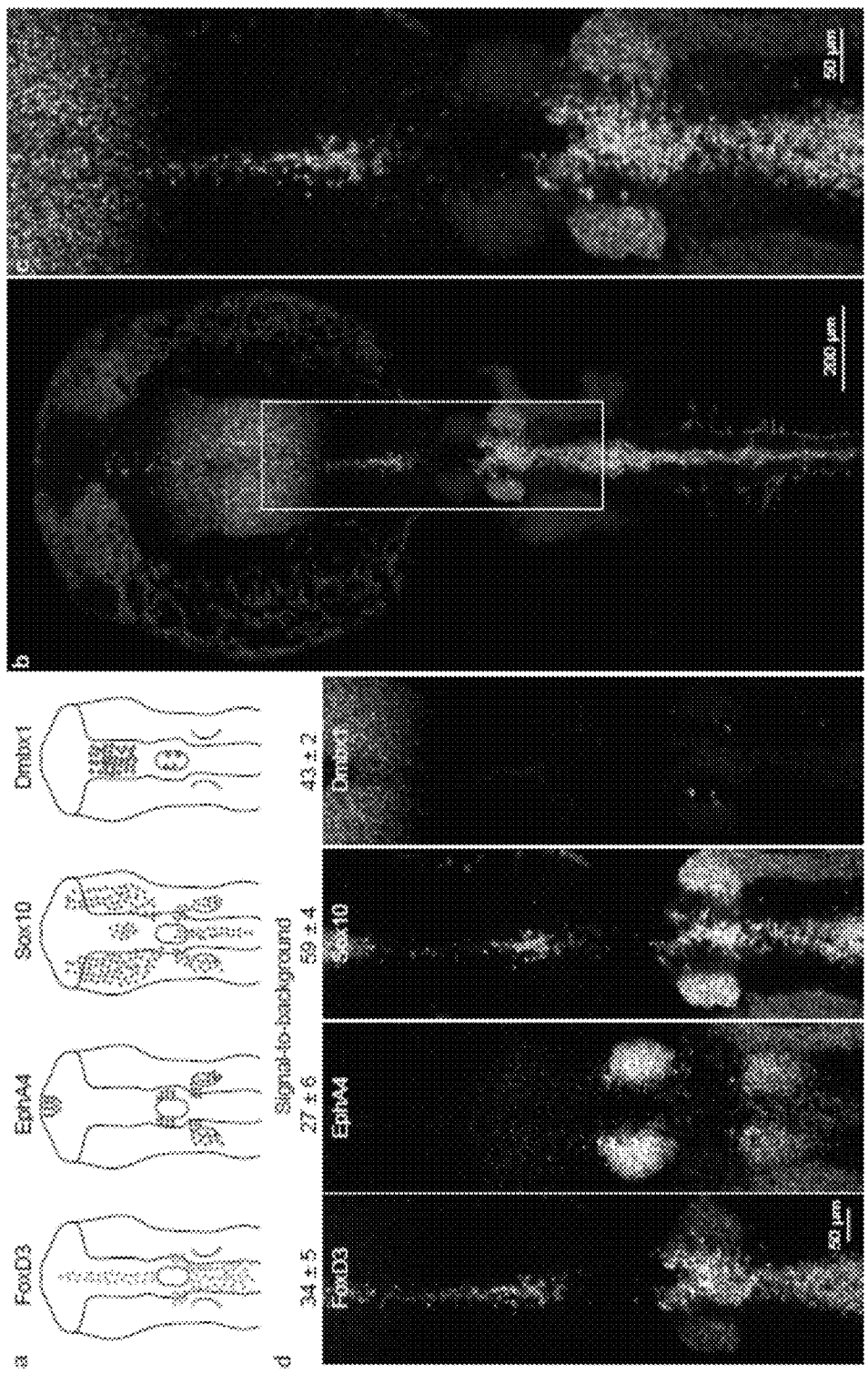
FIG. 10 depicts multiplexed imaging of mRNA expression with high signal-to-background in a fixed whole-mount chicken embryo using fraction initiator probes without probe set optimization.

FIG. 10 demonstrates imaging for 4 target mRNAs in whole-mount chicken embryos with high signal-to-background using unoptimized fractional initiator (aka a split-initiator) probes (Scheme E).

Due to the automatic background suppression property of fractional initiator (aka a split-initiator) probes, the signal-to-background ranges from approximately 25 to 60 for the four target mRNAs without performing any probe set optimization.

FIG. 10. Multiplexed imaging of mRNA expression with high signal-to-background in a fixed whole-mount chicken embryo using fractional initiator (aka a split-initiator) probes without probe set optimization (Scheme E). (a) Expression schematics for four target mRNAs: FoxD3, EphA4, Sox10, Dmbx1. (b) Four-channel confocal micrographs in the head and neural crest. (c) Zoom of depicted region of panel b. (b) Four individual channels from panel c with signal-to-background measurements. Probe sets: 12-20 pairs of unoptimized fractional initiator (aka a split-initiator) probes per target. Amplifiers: four orthogonal HCR amplifiers carrying spectrally distinct fluorophores (one HCR amplifier per target). Embryo fixed: stage HH10.

Example 5

Figure 11:
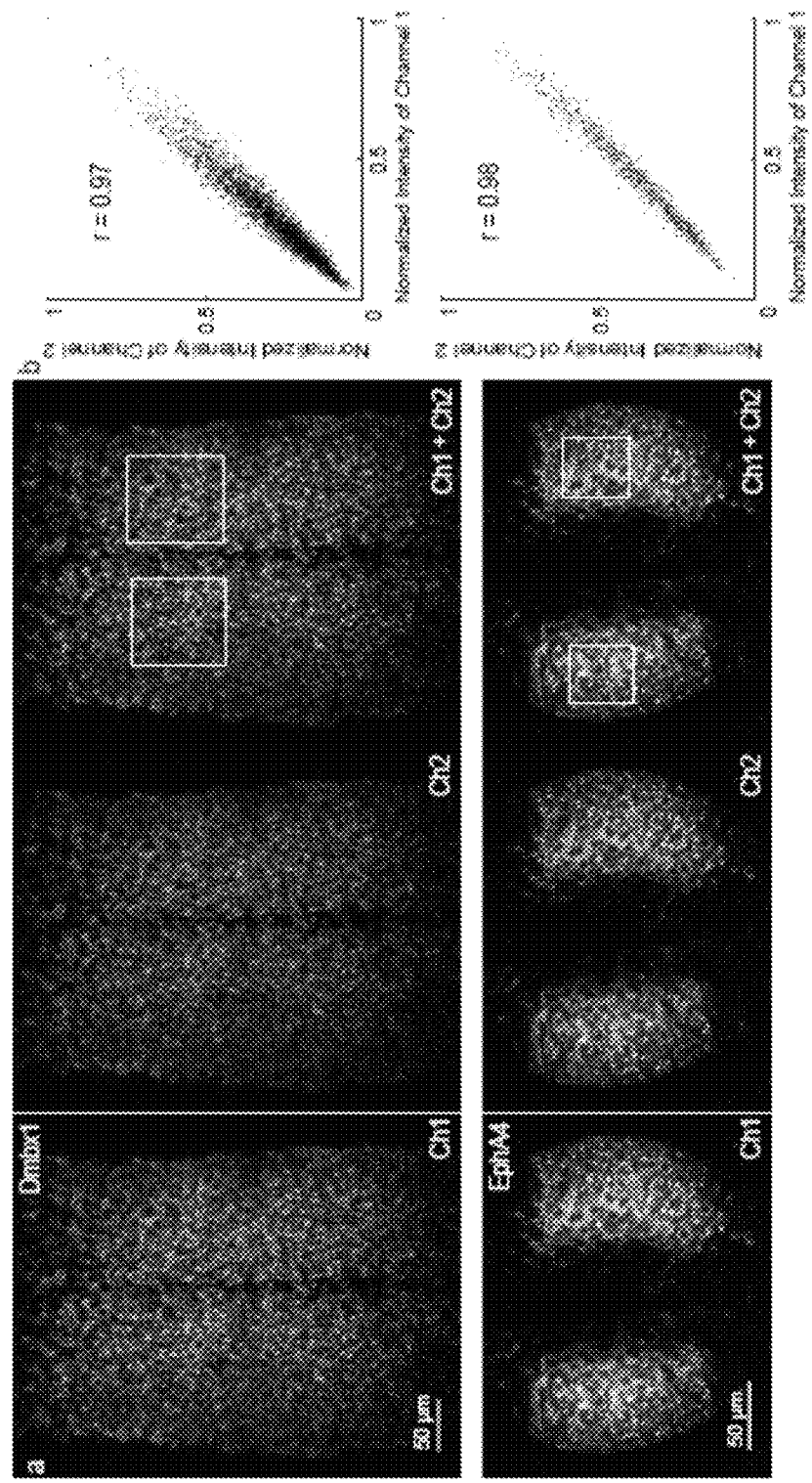
FIG. 11 depicts quantitative imaging of mRNA expression with subcellular resolution in fixed whole-mount chicken embryos using fractional initiator probes.

FIG. 11 demonstrates that in situ HCR using fractional initiator (aka a split-initiator) probes (Scheme E) allows for quantitative analysis of mRNA expression with subcellular resolution within whole-mount chicken embryos.

Each target mRNA was redundantly detected using two fractional initiator probe sets that each triggered a different spectrally-distinct HCR amplifier. Plotting a 2-channel scatter plot of normalized voxel intensities resulted in a tight linear relationship with approximately zero intercept, indicating that HCR signal scales linearly with the number of target mRNAs per imaging voxel. Accuracy improves as the distribution becomes linear and the intercept vanishes; precision improves as the scatter becomes tighter. The 2×2 µm voxels provided subcellular resolution.

These results demonstrate that in situ HCR with fractional initiator (aka a split-initiator) probes allows accurate and precise relative quantitation of mRNA expression with subcellular resolution in an anatomical context without the need for probe set optimization.

FIG. 11. Quantitative imaging of mRNA expression with subcellular resolution in fixed whole-mount chicken embryos. (a) Two-channel redundant detection of target mRNAs. Targets: Dmbx1 and EphA4. Confocal microscopy: 0.2×0.2 µm pixels. Probe sets: 20 pairs of fractional initiator (aka a split-initiator) probes per channel for each target. Amplifiers: two orthogonal HCR amplifiers carrying spectrally distinct fluorophores for each target. Embryos fixed: stage HH10. (b) Highly correlated normalized signal (Pearson correlation coefficient, r) for 2×2 µm voxels in the selected regions of panel b.

REFERENCES

1. Gall J G & Pardue M L (1969) Formation and Detection of RNA-DNA Hybrid Molecules in Cytological Preparations. Proc Natl Acad Sci USA 63:378-383.
2. Cox K H, Deleon D V, Angerer L M, & Angerer R C (1984) Detection of mRNAs in Sea Urchin Embryos by Insitu Hybridization Using Asymmetric RNA Probes. Dev Biol 101(2):485-502.
3. Tautz D & Pfeifle C (1989) A non-radioactive in situ hybridization method for the localization of specific RNAs in Drosophila embryos reveals translational control of the segmentation gene hunchback. Chromosoma 98:81-85.
4. Rosen B & Beddington R S P (1993) Whole-Mount Insitu Hybridization in the Mouse Embryo: Gene-Expression in three Dimensions. Trends Genet 9(5):162-166.
5. Wallner G, Amann R, & Beisker W (1993) Optimizing Fluorescent In situ Hybridization with rRNA-Targeted Oligonucleotide Probes for Flow Cytometric Identification of Microorganisms. Cytometry 14(2):136-143.
6. Nieto M A, Patel K, & Wilkinson D G (1996) In situ hybridization analysis of chick embryos in whole mount and tissue sections. Methods Cell Biol, (Academic Press), Vol 51, pp 219-235.
7. Thisse C & Thisse B (2008) High-resolution in situ hybridization to whole-mount zebrafish embryos. Nat Protoc 3(1):59-69.
8. Kislauskis E H, Li Z, Singer R H, & Taneja K L (1993) Isoform-Specific 3'-Untranslated Sequences Sort α-Cardiac and β-Cytoplasmic Actin Messenger RNAs to Different Cytoplasmic Compartments. J Cell Biol 123(1): 165-172.
9. Femino A, Fay F S, Fogarty K, & Singer R H (1998) Visualization of Single RNA Transcripts In Situ. Science 280(5363):585-590.
10. Levsky J M, Shenoy S M, Pezo R C, & Singer R H (2002) Single-Cell Gene Expression Profiling. Science 297:836-840.
11. Kos man D, et al. (2004) Multiplex Detection of RNA Expression in Drosophila Embryos. Science 305:846.
12. Capodieci P, et al. (2005) Gene Expression Profiling in Single Cells within Tissue. Nat Methods 2(9):663-665.
13. Chan P M, Yuen T, Ruf F, Gonzalez-Maeso J, & Sealfon S C (2005) Method for Multiplex Cellular Detection of mRNAs Using Quantum Dot Fluorescent In Situ Hybridization. Nucleic Acids Res 33(18):e 161.
14. Raj A, van den Bogaard P, Rifkin S A, van Oudenaarden A, & Tyagi S (2008) Imaging Individual mRNA Molecules Using Multiple Singly Labeled Probes. Nat Methods 5(10):877-879.
15. Harland R M (1991) In Situ Hybridization: An Improved Whole-Mount Method for Xenopus Embryos. Methods Cell Biol 36:685-695.
16. Lehmann R & Tautz D (1994) In Situ Hybridization to RNA. Methods Cell Biol, (Academic Press), Vol 44, pp 575-598.
17. Kerstens H M J, Poddighe P J, & Hanselaar A G J M (1995) A Novel in-Situ Hybridization Signal Amplification Method Based on the Deposition of Biotinylated Tyramine. J Histochem Cytochem 43(4):347-352.
18. Wiedorn K H, Kuhl H, Galle J, Caselitz J, & Vollmer E (1999) Comparison of In-Situ Hybridization, Direct and Indirect In-Situ PCR as well as Tyramide Signal Amplification for the Detection of HPV. Histochem Cell Biol 111:89-95.
19. Player A N, Shen L P, Kenny D, Antao V P, & Kolberg J A (2001) Single-Copy Gene Detection Using Branched DNA (bDNA) In Situ Hybridization. J Histochem Cytochem 49(5):603-611.
20. Pernthaler A, Pernthaler J, & Amann R (2002) Fluorescence in situ hybridization and catalyzed reporter deposition for the identification of marine bacteria. Appl Environ Microbiol 68(6):3094-3101.
21. Thisse B, et al. (2004) Spatial and Temporal Expression of the Zebrafish Genome by Large-Scale In Situ Hybridization Screening. The Zebrafish: 2nd Edition Genetics Genomics and Informatics, Methods in Cell Biology, eds Detrich III H W D, Zon L I, & Westerfield M (Elsevier Academic Press, San Diego, Calif.), Vol 77, pp 505-519.

22. Denkers N, Garcia-Villalba P, Rodesch C K, Nielson K R, & Mauch T J (2004) FISHing for Chick Genes: Triple-Label Whole-Mount Fluorescence In Situ Hybridization Detects Simultaneous and Overlapping Gene Expression in Avian Embryos. Dev Dyn 229(3):651-657.
23. Zhou H, et al. (2004) Two-Color, Rolling-Circle Amplification on Antibody Microarrays for Sensitive, Multiplexed Serum-Protein Measurements. Genome Biol 5(4): R28.
24. Larsson C, et al. (2004) In Situ Genotyping Individual DNA Molecules by Target-Primed Rolling-Circle Amplification of Padlock Probes. Nat Methods 1(3):227-232.
25. Clay H & Ramakrishnan L (2005) Multiplex Fluorescent In Situ Hybridization in Zebrafish Embryos Using Tyramide Signal Amplification. ZebrafisH2(2):105-111.
26. Barroso-Chinea P, et al. (2007) Detection of Two Different mRNAs in a Single Section by Dual In Situ Hybridization: A Comparison Between Colorimetric and Fluorescent Detection. J Neurosci Methods 162(1-2):119-128.
27. Acloque H, Wilkinson D G, & Nieto M A (2008) In Situ Hybridization Analysis of Chick Embryos in Whole-Mount and Tissue Sections. Avian Embryology, 2nd Edition, Methods in Cell Biology, ed Bronner-Fraser M (Elsevier Academic Press, San Diego, Calif.), Vol 87, pp 169-185.
28. Piette D, Hendrickx M, Willems E, Kemp C R, & Leyns L (2008) An optimized procedure for whole-mount in situ hybridization on mouse embryos and embryoid bodies. Nat Protoc 3(7):1194-1201.
29. Weiszmann R, Hammonds A S, & Celniker S E (2009) Determination of gene expression patterns using high-throughput RNA in situ hybridization to whole-mount Drosophila embryos. Nat Protoc 4(5):605-618.
30. Larsson C, Grundberg I, Soderberg O, & Nilsson M (2010) In Situ Detection and Genotyping of Individual mRNA Molecules. Nat Methods 7(5):395-397.
31. Wang F, et al. (2012) RNAscope: A Novel in Situ RNA Analysis Platform for Formalin-Fixed, Paraffin-Embedded Tissues. J Mol Diagnostics 14(1):22-29.
32. Dirks R M & Pierce N A (2004) Triggered Amplification by Hybridization Chain Reaction. Proc Natl Acad Sci USA 101(43):15275-15278.
33. Choi H M T, et al. (2010) Programmable in situ amplification for multiplexed imaging of mRNA expression. Nat Biotechnol 28(11):1208-1212.
34. Choi H M T, Beck V A, & Pierce N A (2014) Next-generation in situ hybridization chain reaction: higher gain, lower cost, greater durability. ACS Nano 8(5):4284-4294.
35. Shah S, et al. (2016) Single-molecule RNA detection a t depth via hybridization chain reaction and tissue hydrogel embedding and clearing. Development.
36. Zhang H Q, Li F, Dever B, Li X F, & Le X C (2013) DNA-Media ted Homogeneous Binding Assays for Nucleic Acids and Proteins. Chem Rev 113(4):2812-2841.
37. Wang F, Lu C H, & Willner I (2014) From Cascaded Catalytic Nucleic Acids to Enzyme-DNA Nanostructures: Controlling Reactivity, Sensing, Logic Operations, and Assembly of Complex Structures. Chem Rev 114(5): 2881-2941.
38. Jung C & Ellington A D (2014) Diagnostic applications of nucleic acid circuits. Acc Chem Res 47(6):1825-1835.
39. Ikbal J, Lim G S, & Gao Z Q (2015) The hybridization chain reaction in the development of ultrasensitive nucleic acid assays. Trac-Trends in Analytical Chemistry 64:86-99.
40. McLennan R, et al. (2015) Neural crest migration is driven by a few trailblazer cells with a unique molecular signature narrowly confined to the invasive front. Development 142(11):2014-2025.
41. Huss D, et al. (2015) Combinatorial analysis of mRNA expression patterns in mouse embryos using hybridization chain reaction. Cold Spring Harbor Protocols.
42. Rosenthal A Z, et al. (2013) Localizing transcripts to single cells suggests an important role of uncultured deltaproteobacteria in the termite gut hydrogen economy. Proc Natl Acad Sci USA 110(40):16163-16168.
43. Yamaguchi T, et al. (2015) In situ DNA-hybridization chain reaction (HCR): a facilitated in situ HCR system for the detection of environmental microorganisms. Environmental Microbiology 17(7):2532-2541.
44. Nikolakakis K, Lehnert E, McFall-Ngai M J, & Ruby E G (2015) Use of Hybridization Chain Reaction-Fluorescent In Situ Hybridization To Track Gene Expression by Both Partners during Initiation of Symbiosis. Appl Environ Microbiol 81(14):4728-4735.

What is claimed is:

1. A composition, comprising:
a first hairpin monomer;
a second hairpin monomer;
a first fractional initiator probe comprising a first fractional initiator comprising a sequence capable of binding to the first or second hairpin monomer; and
a second fractional initiator probe comprising a second fractional initiator comprising a sequence capable of binding to the first or second hairpin monomer adjacent to the region where the first fractional initiator binds.

2. A composition, comprising:
a first hairpin monomer, comprising:
a first input domain, comprising a first toehold and a first stem section,
a first output domain, comprising a first hairpin loop and a complement to the first stem section, and
a first reporter molecule;
a second hairpin monomer, comprising:
a second input domain, comprising a second toehold and a second stem section,
a second output domain, comprising a second hairpin loop and a complement to the second stem section,
a second reporter molecule;
a first fractional initiator probe comprising a first fractional initiator comprising a sequence capable of binding to the first or second hairpin monomer; and
a second fractional initiator probe comprising a second fractional initiator comprising a sequence capable of binding to the first or second hairpin monomer adjacent to the region where the first fractional initiator binds.

3. The composition of claim 2, wherein the first stem section can have a same sequence as the second stem section.

4. The composition of claim 2, wherein the complement to the first stem section can have a same sequence as the complement to the second stem section.

5. The composition of claim 4, wherein the first stem section can have a same sequence as the second stem section.

6. The composition of claim 2, wherein the first toehold is complementary to the second hairpin loop.

7. The composition of claim 2, wherein the second toehold is complementary to the first hairpin loop.

8. The composition of claim 2, further comprising a target molecule comprising a first target section and a second target section.

9. The composition of claim 8, wherein the first fractional initiator probe further comprises a first target binding section and the second fractional initiator probe further comprises a second target binding section, wherein the first target binding section is configured to bind to the first target section and the second target binding section is configured to bind to the second target section.

* * * * *

UNITED STATES PATENT AND TRADEMARK OFFICE
CERTIFICATE OF CORRECTION

PATENT NO. : 10,450,599 B2  
APPLICATION NO. : 15/639100  
DATED : October 22, 2019  
INVENTOR(S) : Pierce et al.

Page 1 of 20

It is certified that error appears in the above-identified patent and that said Letters Patent is hereby corrected as shown below:

On the Title Page

The title page showing the illustrative figure should be deleted to be replaced with the attached title page.

In the Drawings

Figs. 1-16 should be replaced with the corrected Figs. 1-18 as shown on the attached pages.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

(12) United States Patent
Pierce et al.

(10) Patent No.: US 10,450,599 B2
(45) Date of Patent: Oct. 22, 2019

(54) FRACTIONAL INITIATOR HYBRIDIZATION CHAIN REACTION

(71) Applicant: California Institute of Technology, Pasadena, CA (US)

(72) Inventors: Niles A. Pierce, Pasadena, CA (US); Harry Ming Tak Choi, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 28 days.

(21) Appl. No.: 15/639,100

(22) Filed: Jun. 30, 2017

(65) Prior Publication Data
US 2018/0010166 A1    Jan. 11, 2018

Related U.S. Application Data

(60) Provisional application No. 62/358,462, filed on Jul. 5, 2016.

(51) Int. Cl.
*C12Q 1/68*    (2018.01)
*C07H 21/00*   (2006.01)
*C12Q 1/682*   (2018.01)

(52) U.S. Cl.
CPC .................. *C12Q 1/682* (2013.01)

(58) Field of Classification Search
CPC ...................... C12Q 1/68; C07H 21/00
See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,270,163 A | 12/1993 | Gold et al. |
| 5,312,728 A | 5/1994 | Lizardi et al. |
| 5,424,413 A | 6/1995 | Hogan et al. |
| 5,459,127 A | 10/1995 | Felgner et al. |
| 5,563,256 A | 10/1996 | Chakraborty et al. |
| 5,579,793 A | 12/1996 | Gajewski et al. |
| 5,635,352 A | 6/1997 | Urdea et al. |
| 5,643,741 A | 7/1997 | Tsukamoto et al. |
| 5,677,136 A | 10/1997 | Simmons et al. |
| 5,681,697 A | 10/1997 | Urdea et al. |
| 5,691,145 A | 11/1997 | Pitner et al. |
| 5,716,827 A | 2/1998 | Tsukamoto et al. |
| 5,750,397 A | 5/1998 | Tsukamoto et al. |
| 5,928,913 A | 7/1999 | Efstathiou et al. |
| 5,989,823 A | 11/1999 | Jayasena et al. |
| 6,128,587 A | 10/2000 | Sjolander |
| 6,130,047 A | 10/2000 | Nadeau et al. |
| 6,242,246 B1 | 6/2001 | Gold et al. |
| 6,255,469 B1 | 7/2001 | Seeman et al. |
| 6,261,783 B1 | 7/2001 | Jayasena et al. |
| 6,264,825 B1 | 7/2001 | Blackburn et al. |
| 6,361,944 B1 | 3/2002 | Mirkin et al. |
| 6,361,945 B1 | 3/2002 | Becker et al. |
| 6,485,965 B1 | 11/2002 | Klatzmann et al. |
| 6,506,559 B1 | 1/2003 | Fire et al. |
| 6,555,367 B1 | 4/2003 | Spence et al. |
| 6,696,285 B1 | 2/2004 | Mills et al. |
| 6,899,871 B2 | 5/2005 | Kasahara et al. |
| 7,033,834 B2 | 4/2006 | Valerio et al. |
| 7,632,641 B2 | 12/2009 | Dirks et al. |
| 7,709,198 B2 | 5/2010 | Luo et al. |
| 7,727,721 B2 | 6/2010 | Pierce et al. |
| 7,960,357 B2 | 6/2011 | Dirks et al. |
| 8,105,778 B2 | 1/2012 | Dirks et al. |
| 8,124,751 B2 | 2/2012 | Pierce et al. |
| 8,241,854 B2 | 8/2012 | Yin et al. |
| 8,318,921 B2 | 11/2012 | Pierce et al. |
| 8,478,543 B2 | 7/2013 | Pierce et al. |
| 8,497,364 B2 | 7/2013 | Pierce et al. |
| 8,507,204 B2 | 8/2013 | Pierce et al. |
| 8,604,182 B2 | 12/2013 | Luo et al. |
| 8,658,361 B2 | 2/2014 | Luo et al. |
| 8,658,780 B2 | 2/2014 | Pierce et al. |
| 8,877,438 B2 | 11/2014 | Yin |
| 8,951,726 B2 | 2/2015 | Luo et al. |
| 8,962,241 B2 | 2/2015 | Yin et al. |
| 8,962,582 B2 | 2/2015 | Dirks et al. |

(Continued)

FOREIGN PATENT DOCUMENTS

| | | |
|---|---|---|
| EP | 0 273 085 A1 | 7/1988 |
| EP | 0731848 B1 | 5/2003 |

(Continued)

OTHER PUBLICATIONS

Aagaard et al., "RNAi Therapeutics: Principles, Prospects and Challenges," Advanced Drug Delivery Reviews, vol. 59, pp. 75-86, 2007.

Acloque, H. et al., "In situ hybridization analysis of chick embryos in whole-mount and tissue sections," Methods in Cell Biology, vol. 87, pp. 169-185, 2008.

Allan et al., "A Concise Total Synthesis of (−)-Quinocarcin via Aryne Annulation," Journal of American Chemical Society, vol. 130, pp. 17270-17271, 2008.

Amarzguioui et al., "Rational design and in vitro and in vitro delivery of Dicer substrate siRNA," Nature Protocols, vol. 1, No. 2, pp. 508-617, 2006.

An, C. I. et al., "Artificial control of gene expression in mammalian cells by modulating RNA interference through aptamer-small molecule interaction," RNA, vol. 12, 710-716, 2006.

(Continued)

*Primary Examiner* — Ethan C Whisenant
(74) *Attorney, Agent, or Firm* — Knobbe, Martens, Olson & Bear, LLP

(57) ABSTRACT

The present disclosure relates to methods and compositions involving HCR reactions that involve initiators that are split into two or more parts. Effective HCR is dependent upon two or more of these split initiators being brought into proximity (e.g., via binding events mediated by a target) such that a full initiator is formed that is capable of triggering HCR signal amplification.

9 Claims, 18 Drawing Sheets